US012679804B2

(12) United States Patent
Christopher et al.

(10) Patent No.: US 12,679,804 B2
(45) Date of Patent: Jul. 14, 2026

(54) 2-(3-ETHYNYLBENZYL)-SUBSTITUTED HETEROCYCLE DERIVATIVES AND RELATED USES

(71) Applicant: CENTESSA PHARMACEUTICALS (UK) LIMITED, Altrincham (GB)

(72) Inventors: John Andrew Christopher, Cambridge (GB); Karl Gibson, Sandwich (GB); Paul Humphries, Santa Clara, CA (US); Gordon Saxty, Cambridge (GB); Matthew Spendiff, Cambridge (GB); Wojciech Zawodny, Cambridge (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 355 days.

(21) Appl. No.: 18/479,695

(22) Filed: Oct. 2, 2023

(65) Prior Publication Data

US 2024/0239744 A1 Jul. 18, 2024

Related U.S. Application Data

(63) Continuation of application No. PCT/EP2022/058817, filed on Apr. 1, 2022.

(60) Provisional application No. 63/170,099, filed on Apr. 2, 2021.

(51) Int. Cl.

| | |
|---|---|
| ***C07D 207/14*** | (2006.01) |
| ***A61K 31/40*** | (2006.01) |
| ***A61K 31/4025*** | (2006.01) |
| ***A61K 31/4439*** | (2006.01) |
| ***A61K 31/4523*** | (2006.01) |
| ***C07D 401/14*** | (2006.01) |
| ***C07D 403/06*** | (2006.01) |
| ***C07D 405/06*** | (2006.01) |
| ***C07D 405/10*** | (2006.01) |

(52) U.S. Cl.

CPC ............ *C07D 207/14* (2013.01); *A61K 31/40* (2013.01); *A61K 31/4025* (2013.01); *A61K 31/4439* (2013.01); *A61K 31/4523* (2013.01); *C07D 401/14* (2013.01); *C07D 403/06* (2013.01); *C07D 405/06* (2013.01); *C07D 405/10* (2013.01)

(58) Field of Classification Search

CPC .. C07D 207/14; C07D 401/14; C07D 403/06; C07D 405/06; C07D 405/10; A61K 31/40; A61K 31/4025; A61K 31/4439; A61K 31/4523

See application file for complete search history.

(56) References Cited

U.S. PATENT DOCUMENTS

| | | | |
|---|---|---|---|
| 4,522,811 | A | 6/1985 | Eppstein et al. |
| 5,763,263 | A | 6/1998 | Dehlinger |
| 8,871,794 | B2 | 10/2014 | Yanagisawa |
| 2010/0074863 | A1 | 3/2010 | Or et al. |
| 2017/0226137 | A1 | 8/2017 | Fujimoto et al. |
| 2020/0255403 | A1 | 8/2020 | Bogen et al. |
| 2021/0155636 | A1 | 5/2021 | Pennington et al. |
| 2023/0271973 | A1 | 8/2023 | Lefker et al. |
| 2023/0331720 | A1 | 10/2023 | Lefker et al. |
| 2024/0239744 | A1 | 7/2024 | Christopher |
| 2024/0360175 | A1 | 10/2024 | O'Boyle et al. |
| 2025/0100968 | A1 | 3/2025 | Ott et al. |
| 2025/0236629 | A1 | 7/2025 | Ott et al. |

FOREIGN PATENT DOCUMENTS

| | | | |
|---|---|---|---|
| CN | 101880276 | A | 11/2010 |
| CN | 102471314 | A | 5/2012 |
| CN | 111051295 | A | 4/2020 |
| CN | 113395993 | A | 9/2021 |

(Continued)

OTHER PUBLICATIONS

Chemical Abstracts Service. CAS Registry: 70693-62-8, PubChem SID: 117687804. Abblis Chemicals: pp. 1-5. STN Entry Date Apr. 12, 2011. Retrieved Nov. 7, 2024. Retrieved from: https://pubchem.ncbi.nlm.nih.gov/substance/117687804.

Li, Kangnan. et al. Diastereoselective and Enantiospecific Synthesis of 1,3-Diamines via 2-Azaallyl Anion Benzylic Ring-Opening of Aziridines. Organic Letters 19(16):4239-4242 (2017).

Tanaka, Kouichi. et al. Reductive Amination of Ketonic Compounds Catalyzed by Cp*Ir(III) Complexes Bearing a Picolinamidato Ligand. The Journal of Organic Chemistry 84(17):10962-10977 (2019).

(Continued)

*Primary Examiner* — Brandon J Fetterolf

(74) *Attorney, Agent, or Firm* — WILSON SONSINI GOODRICH & ROSATI

(57) ABSTRACT

The present disclosure relates to compounds of Formula (I):

(I)

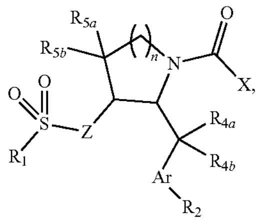

and to their prodrugs, pharmaceutically acceptable salts, pharmaceutical compositions, methods of use, and methods for their preparation. The compounds disclosed herein are useful for modulating orexin-2 receptor activity and may be used in the treatment of disorders in which orexin-2 receptor activity is implicated, such as a neurodegenerative disorder, a symptom of a rare genetic disorder, a mental health disorder, a metabolic syndrome, osteoporosis, cardiac failure, coma, or a complication in emergence from anaesthesia.

20 Claims, No Drawings

(56) References Cited

FOREIGN PATENT DOCUMENTS

| | | | |
|---|---|---|---|
| WO | WO-2008076415 A1 | | 6/2008 |
| WO | WO-2008128121 A1 | | 10/2008 |
| WO | WO-2009070689 A1 | | 6/2009 |
| WO | WO-2011006960 A1 | | 1/2011 |
| WO | WO-2011073376 A1 | | 6/2011 |
| WO | WO-2012117219 A1 | | 9/2012 |
| WO | WO-2012137982 A2 | | 10/2012 |
| WO | WO-2013052845 A1 | | 4/2013 |
| WO | WO-2013092893 A1 | | 6/2013 |
| WO | WO-2015078949 A1 | | 6/2015 |
| WO | WO-2016021629 A1 | | 2/2016 |
| WO | WO-2016022464 A1 | | 2/2016 |
| WO | WO-2017135306 A1 | | 8/2017 |
| WO | WO-2017139603 A1 | | 8/2017 |
| WO | WO-2018164191 A1 | | 9/2018 |
| WO | WO-2018164192 A1 | | 9/2018 |
| WO | WO2019027058 A1 | * | 2/2019 |
| WO | WO-2019027069 A1 | | 2/2019 |
| WO | WO-2020004536 A1 | | 1/2020 |
| WO | WO-2020122092 A1 | | 6/2020 |
| WO | WO-2020122093 A1 | | 6/2020 |
| WO | WO2020158958 A1 | * | 8/2020 |
| WO | WO-2020167706 A1 | | 8/2020 |
| WO | WO-2021048821 A1 | | 3/2021 |
| WO | WO-2021048822 A1 | | 3/2021 |
| WO | WO-2021065893 A1 | | 4/2021 |
| WO | WO-2021107023 A1 | | 6/2021 |
| WO | WO-2021108628 A1 | | 6/2021 |
| WO | WO-2021137982 A1 | | 7/2021 |
| WO | WO-2022051583 A1 | | 3/2022 |
| WO | WO-2022051596 A1 | | 3/2022 |
| WO | WO-2022140316 A1 | | 6/2022 |
| WO | WO-2022207935 A1 | | 10/2022 |
| WO | WO-2023017180 A1 | | 2/2023 |
| WO | WO-2023167865 A1 | | 9/2023 |
| WO | WO-2023167925 A1 | | 9/2023 |
| WO | WO-2024152973 A1 | | 7/2024 |

OTHER PUBLICATIONS

Baykal, Saliha, et al., Decreased Serum Orexin A Levels in Drug-Naive Children With Attention Deficit and Hyperactivity Disorder. Neurological Sciences 40(3):593-602 (2019).
Black, Sarah Wurts, et al., Challenges in the Development of Therapeutics for Narcolepsy. Progress in Neurobiology 152:89-113 (2017).
Boss, Christoph, et al., Orexin Research: Patent News From 2016. Expert Opinion on Therapeutic Patents 27(10):1123-1133 (2017).
Calva, Coleman B, et al., Intranasal Administration of Orexin Peptides: Mechanisms and Therapeutic Potential for Age-Related Cognitive Dysfunction. Brain Research 1731: 24 Pages (2020).
Cheong, Rachel Y, et al., The Role of Hypothalamic Pathology for Non-Motor Features of Huntington's Disease. Journal of Huntington's Disease 8(4):375-391 (2019).
Database STN, CAS, File Registry, RN 1422063-50-0, "Methanesulfonamide, N-[(2R,3S)-2-(phenylmethyl)-3-pyrrolidinyl]-, rei-," (CA Index Name) Supplier WuXi AppTec Corporate Limited American Chemical Society CAS; Entered STN: 3 Printed Pages (Feb. 28, 2013).
De Lecea, L, et al., The Hypocretins: Hypothalamus-specific Peptides With Neuroexcitatory Activity. Proceedings of the National Academy of Sciences of the United States of America 95(1):322-327 (1998).
Funato, Hiromasa, et al., Enhanced Orexin Receptor-2 Signaling Prevents Diet-induced Obesity and Improves Leptin Sensitivity. Cell Metabolism 9(1):64-76 (2009).
Hara, J, et al., Genetic Ablation oOf Orexin Neurons in Mice Results in Narcolepsy, Hypophagia, and Obesity. Neuron 30(2):345-354 (2001).
Hasegawa, Emi, et al., Orexin Neurons Suppress Narcolepsy Via 2 Distinct Efferent Pathways. Journal of Clinical Investigation 124(2):604-616 (2014).
Irukayama-Tomobe, Yoko, et al., Nonpeptide Orexin Type-2 Receptor Agonist Ameliorates Narcolepsy-cataplexy Symptoms In Mouse Models. Proceedings of the National Academy of Sciences of the United States of America 114(22):5731-5736 (2017).
Kelz, Max B, et al., An Essential Role for Orexins in Emergence From General Anesthesia. Proceedings of the National Academy of Sciences of the United States of America 105(4):1309-1314 (2008).
Liu, Mei-Fang, et al., Orexin-A Exerts Neuroprotective Effects via OX1R in Parkinson's Disease. Frontiers in Neuroscience 12: 18 Pages (2018).
Mahoney, Carrie E, et al., The Neurobiological Basis of Narcolepsy. Nature Reviews Neuroscience 20(2):83-93 (2019).
Mieda, Michihiro, et al., Orexin Peptides Prevent Cataplexy and Improve Wakefulness in an Orexin Neuron-Ablated Model of Narcolepsy in Mice. Proceedings of the National Academy of Sciences of the United States of America 101(13):4649-4654 (2004).
Mignot, Emmanuel, et al., Narcolepsy: Genetics, Immunology, and Pathophysiology. Principles and Practice of Sleep Medicine, 6th Edition, Philadelphia, PA, Elsevier Chapter 89:855-872 (2017).
Mignot, Emmanuel, et al., Sleeping With The Hypothalamus: Emerging Therapeutic Targets for Sleep Disorders. Nature Neuroscience 5:1071-1075 (2002).
Mochizuki, Takatoshi, et al., Orexin Receptor 2 Expression in the Posterior Hypothalamus Rescues Sleepiness in Narcoleptic Mice. Proceedings of the National Academy of Sciences of the United States of America 108(11):4471-4476 (2011).
Modi, Hiren R, et al., Intranasal Post-Cardiac Arrest Treatment With Orexin-A Facilitates Arousal From Coma and Ameliorates Neuroinflammation. PLoS One 12(9): 20 Pages (2017).
Nishino, S, et al., Hypocretin (Orexin) Deficiency In Human Narcolepsy. The Lancet 355(9197):39-40 (2000).
Pallais, Jean Pierre, et al., Orexin/Hypocretinin in Multiple Sclerosis and Experimental Autoimmune Encephalomyelitis. Neural Regeneration Research 15(6):1039-1040 (2020).
Patel, Vanlata H, et al., Functional Cardiac Orexin Receptors: Role of Orexin-b/orexin 2 Receptor in Myocardial Protection. Clinical Science 132(24):2547-2564 (2018).
PCT/EP2022/058817 International Search Report and Written Opinion dated Aug. 3, 2022.
PCT/US2021/049003 International Search Report and Written Opinion dated Nov. 11, 2021.
PCT/US2021/049021 International Search Report and Written Opinion dated Nov. 11, 2021.
PCT/US2023/014139 International Search Report and Written Opinion dated May 30, 2023.
PCT/US2023/014275 International Search Report and Written Opinion dated Jun. 15, 2023.
Peyron, R, et al., Functional Imaging of Brain Responses to Pain. A Review and Meta-analysis (2000). Neurophysiologie Clinique 30(5):263-288 (2000).
Sakurai, Takeshi, et al., Orexins and Orexin Receptors: A Family of Hypothalamic Neuropeptides and G Protein-coupled Receptors That Regulate Feeding Behavior. Cell 92(4):573-585 (1998).
Tabuchi, Sawako, et al., Conditional Ablation of Orexin/hypocretin Neurons: A New Mouse Model for the Study of Narcolepsy and Orexin System Function. The Journal of Neuroscience 34(19):6495-6509 (2014).
Thannickal, T C, et al., Reduced Number of Hypocretin Neurons in Human Narcolepsy. Neuron 27(3):469-474 (2000).
Thomasy, Hannah E, et al., Hypocretin Mediates Sleep and Wake Disturbances in a Mouse Model of Traumatic Brain Injury. Journal of Neurotrauma 36(5):802-814 (2019).
Um, Yoo Hyun, et al., Orexin and Alzheimer's Disease: A New Perspective. Psychiatry Investigation 17(7):621-626 (2020).
Wei, Wei, et al., Orexin Regulates Bone Remodeling Via a Dominant Positive Central Action and a Subordinate Negative Peripheral Action. Cell Metabolism 19(6):927-940 (2014).
Yukitake, Hiroshi, et al., TAK-925, An Orexin 2 Receptor-selective Agonist, Shows Robust Wake-promoting Effects in Mice. Pharmacology Biochemistry and Behavior 187: 56 Pages (2019).
Dorwald, F. Zaragoza. Side Reactions in Organic Synthesis: A Guide to Successful Synthesis Design. Weinheim: WILEY-VCH Verlag GmbH & Co. KGaA (2005).

(56) References Cited

OTHER PUBLICATIONS

Jordan, Craig V. Tamoxifen: a most unlikely pioneering medicine. Nature Reviews: Drug Discovery 2(1):205-213 (2003).

* cited by examiner

2-(3-ETHYNYLBENZYL)-SUBSTITUTED HETEROCYCLE DERIVATIVES AND RELATED USES

RELATED APPLICATION

This application is a continuation of International Application No. PCT/EP2022/058817, filed on Apr. 1, 2022, which claims priority to U.S. Provisional Application No. 63/170,099, filed Apr. 2, 2021, each of which is incorporated herein by reference in their entirety.

BACKGROUND

The present disclosure relates to small molecule, potent, and agonists of the orexin-2 receptor (OX2R), designed for the treatment of narcolepsy and other disorders associated with orexin insufficiency. Narcolepsy afflicts 1 in 2000 individuals worldwide. Onset may occur during adolescence for a lifelong duration and debilitating impact on quality of life. There is no known cure, and currently approved treatments are symptomatic. Thus, development of pharmacotherapeutics to replace lost orexin signaling is critically important for treatment of the root cause of narcolepsy.

In narcolepsy Type 1 (NT1), the sole population of neurons that produce orexin (also known as hypocretin) peptides degenerate to cause arousal state boundary dysfunction. Mouse models of narcolepsy have further shown the orexin neurodegeneration and narcoleptic symptoms observed in NT1 patients. Symptoms of narcolepsy may include excessive daytime sleepiness, disturbed nighttime sleep, and inappropriately timed rapid-eye-movement (REM) sleep. Cataplexy is the intrusion of sudden, reversible loss of muscle tone (the atonia of REM sleep) into wakefulness in response to emotional stimuli and is pathognomonic of NT1.

Symptoms of narcolepsy are primarily caused by the loss of orexin neurotransmission at OX2R. Reversal of cataplexy and sleep/wake fragmentation has been achieved by genetic, focal restoration of OX2R signaling in the dorsal raphe nucleus of the pons and the tuberomammillary nucleus of the hypothalamus, respectively, in mice that otherwise lack orexin receptors in those regions. Intracerebroventricular (ICV) administration of orexin A (OXA, 3 nmol) may increase time spent awake and decreases cataplexy-like behavior in orexin-neuron ablated mice. Selective OX2R agonist, YNT-185 administered intraperitoneally or ICV, modestly increases wakefulness in wild type (WT) and orexin ligand-deficient mice, and decrease sleep-onset REM periods and cataplexy-like events in narcoleptic mice. Subcutaneous administration of TAK-925 modestly increases wakefulness in WT mice, but not in OX2R-knockout mice. Brain penetrant and stable OX2R agonists that are bioavailable after alternative routes of administration (including but not limited to oral and intranasal) and that bind with high affinity for potent excitation of arousal-state regulating neurons will provide an improvement to current therapeutics for patients with NT1.

Orexin receptor agonists may also be useful in other indications marked by some degree of orexin neurodegeneration and excessive daytime sleepiness, such as Parkinson's disease, Alzheimer's disease, Huntington's disease, multiple sclerosis, and traumatic brain injury. Because stimulation of OX2R promotes wakefulness in orexin-intact animals, orexin receptor agonists may treat excessive daytime sleepiness in patients with normal levels of OXA, including narcolepsy type 2, idiopathic hypersomnia, sleep apnea, or insomnia. Similarly, orexin receptor agonists may confer wake-promoting benefits in disorders of recurrent hypersomnia, such as Klein-Levin syndrome, or inappropriately timed sleep (i.e., circadian rhythm sleep disorders), such as delayed- or advanced-sleep phase disorder, shift work disorder, and jet lag disorder. The abnormal daytime sleepiness, sleep onset REM periods, and cataplexy-like symptoms of rare genetic disorders (e.g., ADCA-DN, Coffin-Lowry syndrome, Moebius syndrome, Norrie disease, Niemann-Pick disease type C, and Prader-Willi syndrome) could be alleviated with orexin receptor agonists. Other indications in which orexin receptor agonists have been suggested to confer benefits include attention deficit hyperactivity disorder, age-related cognitive dysfunction, metabolic syndrome and obesity, osteoporosis, cardiac failure, coma, and complications in emergence from anesthesia.

The disclosure arises from a need to provide further compounds for the specific modulation of the orexin-2 receptor. In particular, compounds with improved physicochemical, pharmacological and pharmaceutical properties to existing compounds are desirable.

SUMMARY

In some aspects, the present disclosure provides a compound of Formula (I):

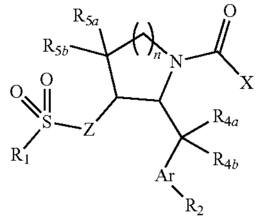

(I)

or a pharmaceutically acceptable salt thereof, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is oxo, halogen, —CN, —OH, —O($C_1$-$C_6$ alkyl), —$NH_2$, —NH($C_1$-$C_6$ alkyl), or —N($C_1$-$C_6$ alkyl)$_2$;

Z is —O— or —$NR_Z$—;

$R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —O($C_1$-$C_6$ alkyl), —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—

($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{15}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_3$-$C_7$ cycloalkyl, or 3- to 7-membered heterocycloalkyl;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_2$ is $C_2$-$C_6$ alkynyl optionally substituted with one or more $R_{2S}$;

each $R_{2S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$;

each $R_{2SS}$ independently is oxo, halogen, —CN, —OH, —$NH_2$, $C_1$-$C_6$ alkyl, $C_2$-$C_6$ alkenyl, or $C_2$-$C_6$ alkynyl, or $C_1$-$C_6$ haloalkyl;

$R_{4a}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{4b}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{5a}$ and $R_{5b}$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_{5S}$; or $R_{5a}$ and $R_{5a}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$;

each $R_{5S}$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl; and n is 0, 1, 2, or 3.

In some aspects, the present disclosure provides a compound obtainable by, or obtained by, a method described herein.

In some aspects, the present disclosure provides a pharmaceutical composition comprising the compound disclosed herein or a pharmaceutically acceptable salt thereof, and a pharmaceutically acceptable diluent or carrier.

In some aspects, the present disclosure provides a method of modulating orexin-2 receptor activity, comprising contacting a cell with an effective amount of the compound disclosed herein.

In some aspects, the present disclosure provides a method of treating or preventing a disease or disorder in a subject in need thereof, comprising administering to the subject a therapeutically effective amount of the compound or pharmaceutical composition disclosed herein.

In some aspects, the present disclosure provides a compound or pharmaceutical composition disclosed herein for use in modulating orexin-2 receptor activity; optionally, the activity is in vitro or in vivo.

In some aspects, the present disclosure provides a compound or pharmaceutical composition disclosed herein for use in treating or preventing a disease or disorder.

In some aspects, the present disclosure provides a use of the compound disclosed herein in the manufacture of a medicament for modulating orexin-2 receptor activity.

In some aspects, the present disclosure provides a use of the compound disclosed herein in the manufacture of a medicament for treating or preventing a disease or disorder.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

The present disclosure relates to 2-(3-ethynylbenzyl)-substituted heterocycle derivatives, prodrugs, and pharmaceutically acceptable salts thereof, which may modulate orexin-2 receptor activity and are accordingly useful in methods of treatment of the human or animal body. The present disclosure also relates to processes for the preparation of these compounds, to pharmaceutical compositions comprising them and to their use in the treatment of disorders in which the orexin-2 receptor is implicated, such as a neurodegenerative disorder, a symptom of a rare genetic disorder, a mental health disorder, a metabolic syndrome, osteoporosis, cardiac failure, coma, or a complication in emergence from anesthesia.

Definitions

Unless otherwise stated, the following terms used in the specification and claims have the following meanings set out below.

Without wishing to be limited by this statement, it is understood that, while various options for variables are described herein, the disclosure intends to encompass operable embodiments having combinations of the options. The disclosure may be interpreted as excluding the non-operable embodiments caused by certain combinations of the options. For example, while various options for variables X, L, and Y are described herein, the disclosure may be interpreted as excluding structures for non-operable compounds caused by certain combinations of variables X, L, and Y (e.g., when each of X, L, and Y is —O—).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1] heptanyl, 2-oxa-6-azaspiro[3.3]heptanyl, 2,6-diazaspiro [3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5] decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo [3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d] pyrimidinyl, 2-azaspiro[3.3]heptanyl, 2-methyl-2-azaspiro [3.3]heptanyl, 2-azaspiro[3.5]nonanyl, 2-methyl-2-azaspiro [3.5]nonanyl, 2-azaspiro[4.5]decanyl, 2-methyl-2-azaspiro [4.5]decanyl, 2-oxa-azaspiro[3.4]octanyl, 2-oxa-azaspiro [3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term “aryl” includes groups with aromaticity, including “conjugated,” or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term “heteroaryl” is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl). In some embodiments, the heteroaryl is thiophenyl or benzothiophenyl. In some embodiments, the heteroaryl is thiophenyl. In some embodiments, the heteroaryl benzothiophenyl.

Furthermore, the terms “aryl” and “heteroaryl” include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl-ringcanbe substituted atone or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term “substituted,” means that any one or more hydrogen atoms on the designated atom is replaced with a selection from the indicated groups, provided that the designated atom’s normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). “Stable compound” and “stable structure” are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term “hydroxy” or “hydroxyl” includes groups with an —OH or —O—.

As used herein, the term “halo” or “halogen” refers to fluoro, chloro, bromo and iodo.

The term “haloalkyl” or “haloalkoxyl” refers to an alkyl or alkoxyl substituted with one or more halogen atoms.

As used herein, the term “optionally substituted haloalkyl” refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl group s covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, itis contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; Greene, T. W., Wuts, P. G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for organic Synthesis*, John Wiley and Sons (1994); and L. Paquette, ed., *Encyclopedia of Reagents for organic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional group sin molecules. A list of protecting groups and how to introduce and remove these groups can be found in Greene, T. W., Wuts, P. G. M., *Protective Groups in Organic Synthesis,* $3^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. Itis to be further understood, unless otherwise stated, any description of a method of treatment includes use of the compounds to prepare a medicament to treat such condition. The treatment includes treatment of human or non-human animals including rodents and other disease models. As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CremophorEL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

For administration by inhalation, the compounds are delivered in the form of an aerosol spray from pressured container or dispenser, which contains a suitable propellant, e.g., a gas such as carbon dioxide, or a nebuliser.

For intranasal administration, the compounds are delivered in solution or solid formulation. In some embodiments, the compounds are delivered in solution as a mist, a drip, or a swab. In some embodiments, the compounds are delivered as a powder. In some embodiments, the compound is included in a kit which further includes an intranasal applicator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, poly orthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral organic acid salts of basic residues such as amines, alkali organic salts of acidic residues such as carboxylic acids, and the like. The pharmaceutically acceptable salts include the conventional non-toxic salts or the quaternary ammonium salts of the parent compound formed, for example, from non-toxic inorganic organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy*, 19th edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described byway of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In some aspects, the present disclosure provides a compound of Formula (I):

(I)

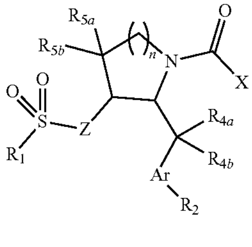

or a pharmaceutically acceptable salt thereof, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is oxo, halogen, —CN, —OH, —O($C_1$-$C_6$ alkyl), —$NH_2$, —NH($C_1$-$C_6$ alkyl), or —N($C_1$-$C_6$ alkyl)$_2$;

Z is —O— or —$NR_Z$—;

$R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —O($C_1$-$C_6$ alkyl), —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_3$-$C_7$ cycloalkyl, or 3- to 7-membered heterocycloalkyl;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_2$ is $C_2$-$C_6$ alkynyl optionally substituted with one or more $R_{2S}$;

each $R_{2S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$;

each $R_{2SS}$ independently is oxo, halogen, —CN, —OH, —$NH_2$, $C_1$-$C_6$ alkyl, $C_2$-$C_6$ alkenyl, or $C_2$-$C_6$ alkynyl, or $C_1$-$C_6$ haloalkyl;

$R_{4a}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{4b}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{5a}$ and $R_{5b}$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_{5S}$; or $R_{5a}$ and $R_{5a}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$;

each $R_{5S}$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl; and n is 0, 1, 2, or 3.

In some aspects, the present disclosure provides a compound of Formula (I):

(I)

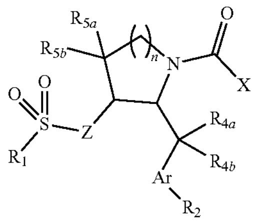

or a pharmaceutically acceptable salt thereof, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is halogen, —OH, or —O($C_1$-$C_6$ alkyl);

Z is —NH—;

$R_1$ is —NH($C_1$-$C_6$ alkyl), —N($C_1$-$C_6$ alkyl)$_2$, $C_1$-$C_6$ alkyl, or 3- to 7-membered heterocycloalkyl, wherein the —NH($C_1$-$C_6$ alkyl), —N($C_1$-$C_6$ alkyl)$_2$, $C_1$-$C_6$ alkyl, or 3- to 7-membered heterocycloalkyl is optionally substituted with one or more $R_{1S}$;

each $R_{1S}$ independently is halogen;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen or —O($C_1$-$C_6$ alkyl);

$R_2$ is $C_2$-$C_6$ alkynyl optionally substituted with one or more $R_{2S}$;

each $R_{2S}$ independently is —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl, wherein the —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl is optionally substituted with one or more $R_{2SS}$;

each $R_{2SS}$ independently is halogen, $C_1$-$C_6$ alkyl, or $C_1$-$C_6$ haloalkyl;

$R_{4a}$ is H;

$R_{4b}$ is H;

$R_{5a}$ and $R_{5b}$ each independently are H or halogen; or $R_{5a}$ and $R_{5a}$, together with the atom they attach to, form $C_3$-$C_7$ cycloalkyl; and n is 1 or 2.

It is understood that, for a compound of the present disclosure, variables X, $R_{X1}$, Z, $R_Z$, $R_1$, $R_{1S}$, Ar, $R_A$, $R_2$, $R_{2S}$, $R_{2SS}$, $R_{4a}$, $R_{4b}$, $R_{5a}$, $R_{5b}$, $R_{5S}$, and n can each be, where applicable, selected from the groups described herein, and any group described herein for any of variables X, $R_{X1}$, Z, $R_Z$, $R_1$, $R_{1S}$, Ar, $R_A$, $R_2$, $R_{2S}$, $R_{2SS}$, $R_{4a}$, $R_{4b}$, $R_{5a}$, $R_{5b}$, $R_{5S}$, and n can be combined, where applicable, with any group described herein for one or more of the remainder of variables X, $R_{X1}$, Z, $R_Z$, $R_1$, $R_{1S}$, Ar, $R_A$, $R_2$, $R_{2S}$, $R_{2SS}$, $R_{4a}$, $R_{4b}$, $R_{5a}$, $R_{5b}$, $R_{5S}$, and n.

Variable X and $R_{X1}$

In some embodiments, X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$.

In some embodiments, X is —O($C_1$-$C_6$ alkyl) optionally substituted with one or more $R_{X1}$.

In some embodiments, X is —O($C_1$-$C_6$ alkyl).

In some embodiments, X is —O($C_1$-$C_6$ alkyl) substituted with one or more $R_{X1}$.

In some embodiments, X is —NH($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is optionally substituted with one or more $R_{X1}$.

In some embodiments, X is —NH($C_1$-$C_6$ alkyl) or —N($C_1$-$C_6$ alkyl)$_2$.

In some embodiments, X is —NH($C_1$-$C_6$ alkyl) or

In some embodiments, X is —$NHCH_3$.

In some embodiments, X is —$NHCH_2CH_3$.

In some embodiments, X is —N($C_1$-$C_6$ alkyl)$_2$.

In some embodiments, X is —N($CH_3$)$_2$.

In some embodiments, X is —N($CH_2CH_3$)$_2$.

In some embodiments, X is —NH($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is substituted with one or more $R_{X1}$.

In some embodiments, X is $C_1$-$C_6$ alkyl optionally substituted with one or more $R_{X1}$.

In some embodiments, X is $C_1$-$C_6$ alkyl.

In some embodiments, X is $C_1$-$C_6$ alkyl substituted with one or more $R_{X1}$.

In some embodiments, X is $C_1$-$C_6$ alkyl substituted with one or more —OH.

In some embodiments, X is $C_3$-$C_7$ cycloalkyl optionally substituted with one or more $R_{X1}$.

In some embodiments, X is $C_3$-$C_7$ cycloalkyl.

In some embodiments, X is $C_3$-$C_7$ cycloalkyl substituted with one or more $R_{X1}$.

In some embodiments, X is 3- to 7-membered heterocycloalkyl optionally substituted with one or more $R_{X1}$.

In some embodiments, X is 3- to 7-membered heterocycloalkyl optionally substituted with one or more $R_{X1}$.

In some embodiments, X is 3- to 7-membered heterocycloalkyl optionally substituted with one or more $R_{X1}$.

In some embodiments, X is oxetanyl or azetidinyl, wherein the oxetanyl or azetidinyl is optionally substituted with one or more $R_{X1}$.

In some embodiments, X is oxetanyl or azetidinyl.

In some embodiments, X is oxetanyl or azetidinyl, wherein the oxetanyl or azetidinyl is substituted with one or more $R_{X1}$.

In some embodiments, at least one $R_{X1}$ is oxo, halogen, —CN, —OH, —O($C_1$-$C_6$ alkyl), —$NH_2$, —NH($C_1$-$C_6$ alkyl), or —N($C_1$-$C_6$ alkyl)$_2$.

In some embodiments, at least one $R_{X1}$ halogen, or —OH, —O($C_1$-$C_6$ alkyl).

In some embodiments, at least one $R_{X1}$ is oxo.

In some embodiments, at least one $R_{X1}$ is halogen.

In some embodiments, at least one $R_{X1}$ is F or Cl.

In some embodiments, at least one $R_{X1}$ is —CN.

In some embodiments, at least one $R_{X1}$ is —OH.

In some embodiments, at least one $R_{X1}$ is —O($C_1$-$C_6$ alkyl).

In some embodiments, at least one $R_{X1}$ is —$NH_2$, —NH ($C_1$-$C_6$ alkyl), or —N($C_1$-$C_6$ alkyl)$_2$.

In some embodiments, at least one $R_{X1}$ is —$NH_2$.

In some embodiments, at least one $R_{X1}$ is —NH($C_1$-$C_6$ alkyl) or —N($C_1$-$C_6$ alkyl)$_2$.

Variable Z and $R_Z$

In some embodiments, Z is —O—.

In some embodiments, Z is —$NR_Z$—.

In some embodiments, Z is —NH—.

In some embodiments, $R_Z$ is H.

In some embodiments, $R_Z$ is $C_1$-$C_6$ alkyl, $C_2$-$C_6$ alkenyl, $C_2$-$C_6$ alkynyl, or $C_1$-$C_6$ haloalkyl.

In some embodiments, $R_Z$ is $C_1$-$C_6$ alkyl.

In some embodiments, $R_Z$ is $C_2$-$C_6$ alkenyl.

In some embodiments, $R_Z$ is $C_2$-$C_6$ alkynyl.

In some embodiments, $R_Z$ is $C_1$-$C_6$ haloalkyl.

Variable $R_1$ and $R_{1S}$

In some embodiments, $R_1$ is —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —O($C_1$-$C_6$ alkyl), —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$.

In some embodiments, $R_1$ is —NH($C_1$-$C_6$ alkyl), —N($C_1$-$C_6$ alkyl)$_2$, $C_1$-$C_6$ alkyl, or 3- to 7-membered heterocycloalkyl, wherein the —NH($C_1$-$C_6$ alkyl), —N($C_1$-$C_6$ alkyl)$_2$, $C_1$-$C_6$ alkyl, or 3- to 7-membered heterocycloalkyl is optionally substituted with one or more $R_{1S}$.

In some embodiments, $R_1$ is —OH or —O($C_1$-$C_6$ alkyl) optionally substituted with one or more $R_{1S}$.

In some embodiments, $R_1$ is —OH.

In some embodiments, $R_1$ is —O($C_1$-$C_6$ alkyl) optionally substituted with one or more $R_{1S}$.

In some embodiments, $R_1$ is —$NH_2$, —NH($C_1$-$C_6$ alkyl), or —N($C_1$-$C_6$ alkyl)$_2$, wherein the —NH($C_1$-$C_6$ alkyl) or —N($C_1$-$C_6$ alkyl)$_2$ is optionally substituted with one or more $R_{1S}$.

In some embodiments, $R_1$ is —$NH_2$.

In some embodiments, $R_1$ is —NH($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is optionally substituted with one or more $R_{1S}$.

In some embodiments, $R_1$ is —NH($C_1$-$C_6$ alkyl) optionally substituted with one or more $R_{1S}$.

In some embodiments, $R_1$ is —N($C_1$-$C_6$ alkyl)$_2$ optionally substituted with one or more RIS.

In some embodiments, $R_1$ is —S($C_1$-$C_6$ alkyl) or —S($C_6$-$C_{10}$ aryl), wherein the —S($C_1$-$C_6$ alkyl) or —S($C_6$-$C_{10}$ aryl) is optionally substituted with one or more $R_{1S}$.

In some embodiments, $R_1$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more $R_{1S}$.

In some embodiments, $R_1$ is $C_1$-$C_6$ alkyl, $C_2$-$C_6$ alkenyl, or $C_2$-$C_6$ alkynyl.

In some embodiments, $R_1$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is substituted with one or more $R_{1S}$.

In some embodiments, $R_1$ is $C_1$-$C_6$ alkyl optionally substituted with one or more $R_{1S}$.

In some embodiments, $R_1$ is $C_1$-$C_6$ alkyl.

In some embodiments, $R_1$ is $CH_3$ or $CH_2CH_3$.

In some embodiments, $R_1$ is $CH_3$.

In some embodiments, $R_1$ is $CH_2CH_3$.

In some embodiments, $R_1$ is $C_1$-$C_6$ alkyl substituted with one or more $R_{1S}$.

In some embodiments, $R_1$ is $C_2$-$C_6$ alkenyl optionally substituted with one or more $R_{1S}$.

In some embodiments, $R_1$ is $C_2$-$C_6$ alkenyl.

In some embodiments, $R_1$ is $C_2$-$C_6$ alkenyl substituted with one or more $R_{1S}$.

In some embodiments, $R_1$ is $C_2$-$C_6$ alkynyl optionally substituted with one or more $R_{1S}$.

In some embodiments, $R_1$ is $C_2$-$C_6$ alkynyl.

In some embodiments, $R_1$ is $C_2$-$C_6$ alkynyl substituted with one or more $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the $C_6$-$C_{10}$ aryl, 5- to 10-membered heteroaryl, $C_3$-$C_7$ cycloalkyl, or 3- to 7-membered heterocycloalkyl is optionally substituted with one or more $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the $C_6$-$C_{10}$ aryl, 5- to 10-membered heteroaryl, $C_3$-$C_7$ cycloalkyl, or 3- to 7-membered heterocycloalkyl is substituted with one or more $R_{1S}$.

In some embodiments, $R_1$ is 3- to 7-membered heterocycloalkyl optionally substituted with one or more $R_{1S}$.

In some embodiments, $R_1$ is 3- to 7-membered heterocycloalkyl.

In some embodiments, $R_1$ is 3- to 7-membered heterocycloalkyl substituted with one or more $R_{1S}$.

In some embodiments, $R_1$ is oxetanyl or azetidinyl, wherein the oxetanyl or azetidinyl is optionally substituted with one or more $R_{1S}$.

In some embodiments, $R_1$ is oxetanyl or azetidinyl.

In some embodiments, $R_1$ is oxetanyl or azetidinyl, wherein the oxetanyl or azetidinyl is substituted with one or more $R_{1S}$.

In some embodiments, $R_1$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl), wherein the —O—($C_6$-$C_{10}$ aryl), —O-(5- to 10-membered heteroaryl), —O—($C_3$-$C_{10}$ cycloalkyl), or —O-(3- to 7-membered heterocycloalkyl) is optionally substituted with one or more $R_{1S}$.

In some embodiments, $R_1$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl).

In some embodiments, $R_1$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl), wherein the —O—($C_6$-$C_{10}$ aryl), —O-(5- to 10-membered heteroaryl), —O—($C_3$-$C_{10}$ cycloalkyl), or —O-(3- to 7-membered heterocycloalkyl) is substituted with one or more $R_{1S}$.

In some embodiments, $R_1$ is —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$.

In some embodiments, $R_1$ is —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_1$ is —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is substituted with one or more $R_{1S}$.

In some embodiments, at least one $R_{1S}$ is oxo, halogen, or —CN.

In some embodiments, at least one $R_{1S}$ is oxo.

In some embodiments, at least one $R_{15}$ is halogen.

In some embodiments, at least one $R_{15}$ is F or Cl.

In some embodiments, at least one $R_{15}$ is —CN.

In some embodiments, at least one $R_{15}$ is —OH or —O($C_1$-$C_6$ alkyl).

In some embodiments, at least one $R_{15}$ is —OH.

In some embodiments, at least one $R_{15}$ is —O($C_1$-$C_6$ alkyl).

In some embodiments, at least one $R_{15}$ is —$NH_2$, —NH($C_1$-$C_6$ alkyl), or —N($C_1$-$C_6$ alkyl)$_2$.

In some embodiments, at least one $R_{15}$ is —$NH_2$.

In some embodiments, at least one $R_{15}$ is —NH($C_1$-$C_6$ alkyl).

In some embodiments, at least one $R_{15}$ is —N($C_1$-$C_6$ alkyl)$_2$.

In some embodiments, at least one $R_{15}$ is —S($C_1$-$C_6$ alkyl) or —$SO_2$($C_1$-$C_6$ alkyl).

In some embodiments, at least one $R_{15}$ is —S($C_1$-$C_6$ alkyl).

In some embodiments, at least one $R_{15}$ is —$SO_2$($C_1$-$C_6$ alkyl).

In some embodiments, at least one $R_{15}$ is $C_1$-$C_6$ alkyl, $C_2$-$C_6$ alkenyl, or $C_2$-$C_6$ alkynyl.

In some embodiments, at least one $R_{15}$ is $C_1$-$C_6$ alkyl.

In some embodiments, at least one $R_{15}$ is $C_2$-$C_6$ alkenyl.

In some embodiments, at least one $R_{1S}$ is $C_2$-$C_6$ alkynyl.

In some embodiments, at least one $R_{15}$ is $C_3$-$C_7$ cycloalkyl or 3- to 7-membered heterocycloalkyl.

In some embodiments, at least one $R_{15}$ is $C_3$-$C_7$ cycloalkyl.

In some embodiments, at least one $R_{15}$ is 3- to 7-membered heterocycloalkyl.

Variables Ar and $R_A$

In some embodiments, Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$.

In some embodiments, Ar is $C_6$-$C_{10}$ aryl or 5- to 10-membered heteroaryl.

In some embodiments, Ar is $C_6$-$C_{10}$ aryl or 5- to 10-membered heteroaryl, wherein the $C_6$-$C_{10}$ aryl or 5- to 10-membered heteroaryl is substituted with one or more $R_A$.

In some embodiments, Ar is $C_6$-$C_{10}$ aryl optionally substituted with one or more $R_A$.

In some embodiments, Ar is $C_6$-$C_{10}$ aryl.

In some embodiments, Ar is $C_6$-$C_{10}$ aryl substituted with one or more $R_A$.

In some embodiments, Ar is phenyl optionally substituted with one or more $R_A$.

In some embodiments, Ar is phenyl.

In some embodiments, Ar is phenyl substituted with one or more $R_A$.

In some embodiments, Ar is 5- to 10-membered heteroaryl optionally substituted with one or more $R_A$.

In some embodiments, Ar is 5- to 10-membered heteroaryl.

In some embodiments, Ar is 5- to 10-membered heteroaryl substituted with one or more $R_A$.

In some embodiments, Ar is pyridinyl optionally substituted with one or more $R_A$.

In some embodiments, Ar is pyridinyl.

In some embodiments, Ar is pyridinyl substituted with one or more $R_A$.

In some embodiments, at least one $R_A$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

In some embodiments, at least one $R_A$ is halogen or —O($C_1$-$C_6$ alkyl).

In some embodiments, at least one $R_A$ is halogen or —CN.

In some embodiments, at least one $R_A$ is halogen.

In some embodiments, at least one $R_A$ is F or Cl.

In some embodiments, at least one $R_A$ is —CN.

In some embodiments, at least one $R_A$ is —OH or —O($C_1$-$C_6$ alkyl).

In some embodiments, at least one $R_A$ is —OH.

In some embodiments, at least one $R_A$ is —O($C_1$-$C_6$ alkyl).

In some embodiments, at least one $R_A$ is —$NH_2$, —NH($C_1$-$C_6$ alkyl), or —N($C_1$-$C_6$ alkyl)$_2$.

In some embodiments, at least one $R_A$ is —$NH_2$.

In some embodiments, at least one $R_A$ is —NH($C_1$-$C_6$ alkyl) or —N($C_1$-$C_6$ alkyl)$_2$.

In some embodiments, at least one $R_A$ is —NH($C_1$-$C_6$ alkyl).

In some embodiments, at least one $R_A$ is —N($C_1$-$C_6$ alkyl)$_2$.

In some embodiments, at least one $R_A$ is $C_1$-$C_6$ alkyl, $C_2$-$C_6$ alkenyl, $C_2$-$C_6$ alkynyl, or $C_1$-$C_6$ haloalkyl.

In some embodiments, at least one $R_A$ is $C_1$-$C_6$ alkyl.

In some embodiments, at least one $R_A$ is $C_2$-$C_6$ alkenyl.

In some embodiments, at least one $R_A$ is $C_2$-$C_6$ alkynyl.

In some embodiments, at least one $R_A$ is $C_1$-$C_6$ haloalkyl.

In some embodiments, at least one $R_A$ is $CF_3$.

Variables $R_2$, $R_{2S}$, and $R_{2SS}$

In some embodiments, $R_2$ is $C_2$-$C_6$ alkynyl optionally substituted with one or more $R_{2S}$.

In some embodiments, $R_2$ is $C_2$-$C_6$ alkynyl.

In some embodiments, $R_2$ is $C_2$-$C_6$ alkynyl substituted with one or more $R_{2S}$.

In some embodiments, $R_2$ is ethynyl optionally substituted with one or more $R_{2S}$.

In some embodiments, $R_2$ is ethynyl.

In some embodiments, $R_2$ is ethynyl substituted with one or more $R_{2S}$.

In some embodiments, at least one $R_{2S}$ is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$.

In some embodiments, at least one $R_{2S}$ is —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl, wherein the —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl is optionally substituted with one or more $R_{2SS}$.

In some embodiments, at least one $R_{2S}$ is oxo, halogen, or —CN.

In some embodiments, at least one $R_{2S}$ is oxo.

In some embodiments, at least one $R_{2S}$ is halogen.

In some embodiments, at least one $R_{2S}$ is —CN.

In some embodiments, at least one $R_{2S}$ is —OH or —O($C_1$-$C_6$ alkyl) optionally substituted with one or more $R_{2SS}$.

In some embodiments, at least one $R_{2S}$ is —OH.

In some embodiments, at least one $R_{2S}$ is —O($C_1$-$C_6$ alkyl) optionally substituted with one or more $R_{2SS}$.

In some embodiments, at least one $R_{2S}$ is —O($C_1$-$C_6$ alkyl).

In some embodiments, at least one $R_{2S}$ is —O($C_1$-$C_6$ alkyl) substituted with one or more $R_{2SS}$.

In some embodiments, at least one $R_{2S}$ is —$NH_2$, —NH ($C_1$-$C_6$ alkyl), or —N($C_1$-$C_6$ alkyl)$_2$, wherein the —NH($C_1$-$C_6$ alkyl) or —N($C_1$-$C_6$ alkyl)$_2$ is optionally substituted with one or more $R_{2SS}$.

In some embodiments, at least one $R_{2S}$ is —$NH_2$.

In some embodiments, at least one $R_{2S}$—NH($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is optionally substituted with one or more $R_{2SS}$.

In some embodiments, at least one $R_{2S}$ is —S($C_1$-$C_6$ alkyl) or —$SO_2$($C_1$-$C_6$ alkyl), wherein the —S($C_1$-$C_6$ alkyl) or —$SO_2$($C_1$-$C_6$ alkyl) is optionally substituted with one or more $R_{2SS}$.

In some embodiments, at least one $R_{2S}$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more $R_{2SS}$.

In some embodiments, at least one $R_{2S}$ is $C_1$-$C_6$ alkyl, $C_2$-$C_6$ alkenyl, or $C_2$-$C_6$ alkynyl.

In some embodiments, at least one $R_{2S}$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is substituted with one or more $R_{2SS}$.

In some embodiments, at least one $R_{2S}$ is $C_1$-$C_6$ alkyl optionally substituted with one or more $R_{2SS}$.

In some embodiments, at least one $R_{2S}$ is $C_1$-$C_6$ alkyl.

In some embodiments, at least one $R_{2S}$ is $C_1$-$C_6$ alkyl substituted with one or more $R_{2SS}$.

In some embodiments, at least one $R_{2S}$ is $C_6$-$C_{10}$ aryl, 5- to 10-membered heteroaryl, $C_3$-$C_7$ cycloalkyl, or 3- to 7-membered heterocycloalkyl, wherein the $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$.

In some embodiments, at least one $R_{2S}$ is $C_6$-$C_{10}$ aryl, 5- to 10-membered heteroaryl, $C_3$-$C_7$ cycloalkyl, or 3- to 7-membered heterocycloalkyl.

In some embodiments, at least one $R_{2S}$ is $C_6$-$C_{10}$ aryl, 5- to 10-membered heteroaryl, $C_3$-$C_7$ cycloalkyl, or 3- to 7-membered heterocycloalkyl, wherein the $C_6$-$C_{10}$ aryl, 5- to 10-membered heteroaryl, $C_3$-$C_7$ cycloalkyl, or 3- to 7-membered heterocycloalkyl is substituted with one or more $R_{2SS}$.

In some embodiments, at least one $R_{2S}$ is $C_6$-$C_{10}$ aryl optionally substituted with one or more $R_{2SS}$.

In some embodiments, at least one $R_{2S}$ is $C_6$-$C_{10}$ aryl.

In some embodiments, at least one $R_{2S}$ is $C_6$-$C_{10}$ aryl substituted with one or more $R_{2SS}$.

In some embodiments, at least one $R_{2S}$ is 5- to 10-membered heteroaryl optionally substituted with one or more $R_{2SS}$.

In some embodiments, at least one $R_{2S}$ is 5- to 10-membered heteroaryl.

In some embodiments, at least one $R_{2S}$ is 5- to 10-membered heteroaryl substituted with one or more $R_{2SS}$.

In some embodiments, at least one $R_{2S}$ is $C_3$-$C_7$ cycloalkyl optionally substituted with one or more $R_{2SS}$.

In some embodiments, at least one $R_{2S}$ is $C_3$-$C_7$ cycloalkyl.

In some embodiments, at least one $R_{2S}$ is $C_3$-$C_7$ cycloalkyl substituted with one or more $R_{2SS}$.

In some embodiments, at least one $R_{2S}$ is 3- to 7-membered heterocycloalkyl optionally substituted with one or more $R_{2SS}$.

In some embodiments, at least one $R_{2S}$ is 3- to 7-membered heterocycloalkyl.

In some embodiments, at least one $R_{2S}$ is 3- to 7-membered heterocycloalkyl substituted with one or more $R_{2SS}$.

In some embodiments, at least one each $R_{2SS}$ is oxo, halogen, —CN, —OH, —$NH_2$, $C_1$-$C_6$ alkyl, $C_2$-$C_6$ alkenyl, or $C_2$-$C_6$ alkynyl, or $C_1$-$C_6$ haloalkyl.

In some embodiments, at least one each $R_{2SS}$ is halogen, $C_1$-$C_6$ alkyl, or $C_1$-$C_6$ haloalkyl.

In some embodiments, at least one each $R_{2SS}$ is oxo, halogen, —CN, —OH, or —$NH_2$.

In some embodiments, at least one each $R_{2SS}$ is oxo.

In some embodiments, at least one each $R_{2SS}$ is halogen.

In some embodiments, at least one each $R_{2SS}$ is F or Cl.

In some embodiments, at least one each $R_{2SS}$ is —CN.

In some embodiments, at least one each $R_{2SS}$ is —OH.

In some embodiments, at least one each $R_{2SS}$ is —$NH_2$.

In some embodiments, at least one each $R_{2SS}$ is $C_1$-$C_6$ alkyl, $C_2$-$C_6$ alkenyl, or $C_2$-$C_6$ alkynyl, or $C_1$-$C_6$ haloalkyl.

In some embodiments, at least one each $R_{2SS}$ is $C_1$-$C_6$ alkyl.

In some embodiments, at least one each $R_{2SS}$ is $C_2$-$C_6$ alkenyl.

In some embodiments, at least one each $R_{2SS}$ is $C_2$-$C_6$ alkynyl.

In some embodiments, at least one each $R_{2SS}$ is $C_1$-$C_6$ haloalkyl.

In some embodiments, at least one each $R_{2SS}$ is $CF_3$.

Variables $R_{4a}$ and $R_{4b}$

In some embodiments, $R_{4a}$ is H.

In some embodiments, $R_{4a}$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

In some embodiments, $R_{4a}$ is halogen.

In some embodiments, $R_{4a}$ is —CN.

In some embodiments, $R_{4a}$ is —OH.

In some embodiments, $R_{4a}$ is —O($C_1$-$C_6$ alkyl).

In some embodiments, $R_{4a}$ is —$NH_2$, —NH($C_1$-$C_6$ alkyl), or —N($C_1$-$C_6$ alkyl)$_2$.

In some embodiments, $R_{4a}$ is $C_1$-$C_6$ alkyl, $C_2$-$C_6$ alkenyl, $C_2$-$C_6$ alkynyl, or $C_1$-$C_6$ haloalkyl.

In some embodiments, $R_{4b}$ is H.

In some embodiments, $R_{4b}$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

In some embodiments, $R_{4b}$ is halogen.

In some embodiments, $R_{4b}$ is —CN.

In some embodiments, $R_{4b}$ is —OH.

In some embodiments, $R_{4b}$ is —O($C_1$-$C_6$ alkyl).

In some embodiments, $R_{4b}$ is —$NH_2$, —NH($C_1$-$C_6$ alkyl), or —N($C_1$-$C_6$ alkyl)$_2$.

In some embodiments, $R_{4b}$ is $C_1$-$C_6$ alkyl, $C_2$-$C_6$ alkenyl, $C_2$-$C_6$ alkynyl, or $C_1$-$C_6$ haloalkyl.

In some embodiments, both $R_{4a}$ and $R_{4b}$ are H.

Variables $R_{5a}$, $R_{5b}$, and $R_{5S}$

In some embodiments, $R_{5a}$ and $R_{5b}$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_{5S}$; or $R_{5a}$ and $R_{5a'}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$.

In some embodiments, $R_{5a}$ and $R_{5b}$ each independently are H or halogen; or $R_{5a}$ and $R_{5a'}$, together with the atom they attach to, form $C_3$-$C_7$ cycloalkyl optionally substituted with one or more $R_{5S}$.

In some embodiments, $R_{5a}$ and $R_{5b}$ each independently are H or halogen; or $R_{5a}$ and $R_{5a'}$, together with the atom they attach to, form $C_3$-$C_7$ cycloalkyl.

In some embodiments, $R_{5a}$ and $R_{5b}$ each independently are H or halogen.

In some embodiments, at least one of $R_{5a}$ and $R_{5b}$ is H.

In some embodiments, $R_{5a}$ and $R_{5b}$ each are H.

In some embodiments, $R_{5a}$ and $R_{5b}$ each independently are halogen.

In some embodiments, $R_{5a}$ and $R_{5b}$ each independently are F or Cl.

In some embodiments, at least one of $R_{5a}$ and $R_{5b}$ is halogen.

In some embodiments, at least one of $R_{5a}$ and $R_{5b}$ is F or Cl.

In some embodiments, at least one of $R_{5a}$ and $R_{5b}$ is —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_{5S}$.

In some embodiments, at least one of $R_{5a}$ and $R_{5b}$ is —CN.

In some embodiments, at least one of $R_{5a}$ and $R_{5b}$ is —OH or —O($C_1$-$C_6$ alkyl), wherein the —O($C_1$-$C_6$ alkyl) is optionally substituted with one or more $R_{5S}$.

In some embodiments, at least one of $R_{5a}$ and $R_{5b}$ is —$NH_2$, —NH($C_1$-$C_6$ alkyl), or —N($C_1$-$C_6$ alkyl)$_2$, wherein the —NH($C_1$-$C_6$ alkyl) or —N($C_1$-$C_6$ alkyl)$_2$ is optionally substituted with one or more $R_{5S}$.

In some embodiments, at least one of $R_{5a}$ and $R_{5b}$ is $C_1$-$C_6$ alkyl, $C_2$-$C_6$ alkenyl, or $C_2$-$C_6$, wherein the $C_1$-$C_6$ alkyl, $C_2$-$C_6$ alkenyl, or $C_2$-$C_6$ alkynyl is optionally substituted with one or more $R_{5S}$.

In some embodiments, $R_{5a}$ and $R_{5a'}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$.

In some embodiments, $R_{5a}$ and $R_{5a'}$, together with the atom they attach to, form $C_3$-$C_7$ cycloalkyl or 3- to 7-membered heterocycloalkyl.

In some embodiments, $R_{5a}$ and $R_{5a'}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is substituted with one or more $R_{5S}$.

In some embodiments, $R_{5a}$ and $R_{5a'}$, together with the atom they attach to, form $C_3$-$C_7$ cycloalkyl optionally substituted with one or more $R_{5S}$.

In some embodiments, $R_{5a}$ and $R_{5a'}$, together with the atom they attach to, form $C_3$-$C_7$ cycloalkyl.

In some embodiments, $R_{5a}$ and $R_{5a'}$, together with the atom they attach to, form $C_3$-$C_7$ cycloalkyl substituted with one or more $R_{5S}$.

In some embodiments, $R_{5a}$ and $R_{5a'}$, together with the atom they attach to, form 3- to 7-membered heterocycloalkyl optionally substituted with one or more $R_{5S}$.

In some embodiments, $R_{5a}$ and $R_{5a'}$, together with the atom they attach to, form 3- to 7-membered heterocycloalkyl.

In some embodiments, $R_{5a}$ and $R_{5a'}$, together with the atom they attach to, form 3- to 7-membered heterocycloalkyl substituted with one or more $R_{5S}$.

In some embodiments, at least one $R_{5S}$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

In some embodiments, at least one $R_{5S}$ is halogen or —CN

In some embodiments, at least one $R_{5S}$ is —OH or —O($C_1$-$C_6$ alkyl).

In some embodiments, at least one $R_{5S}$ is —$NH_2$, —NH ($C_1$-$C_6$ alkyl), or —N($C_1$-$C_6$ alkyl)$_2$.

In some embodiments, at least one $R_{5S}$ is $C_1$-$C_6$ alkyl, $C_2$-$C_6$ alkenyl, $C_2$-$C_6$ alkynyl, or $C_1$-$C_6$ haloalkyl.

Variable n

In some embodiments, n is 0, 1, 2, or 3.

In some embodiments, n is 0.

In some embodiments, n is 1, 2, or 3.

In some embodiments, n is 1 or 2.

In some embodiments, n is 1.

In some embodiments, n is 2

In some embodiments, n is 3.

Exemplary Embodiments of the Compounds

In some embodiments, the compound is of Formula (I-1), (I-2), (I-3), or (I-4):

(I-1)

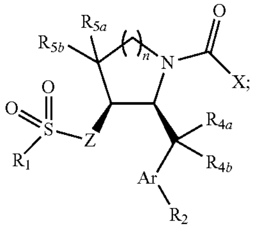

(I-2)

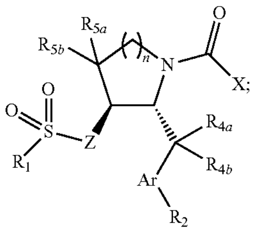

(I-3)

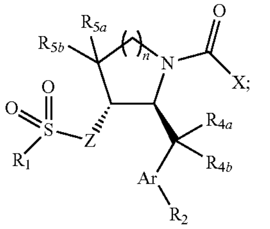

(I-4)

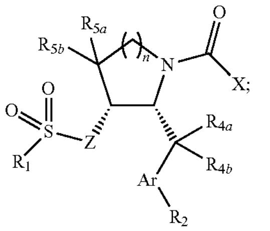

or a pharmaceutically acceptable salt thereof.

In some embodiments, the compound is of Formula (II):

(II)

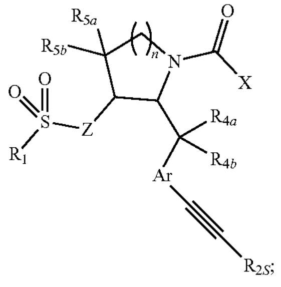

or a pharmaceutically acceptable salt thereof.

In some embodiments, the compound is of Formula (II-1), (II-2), (II-3), or (II-4):

(II-1)

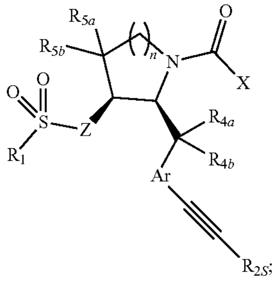

(II-2)

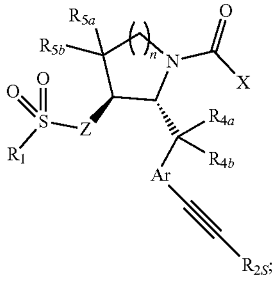

(II-3)

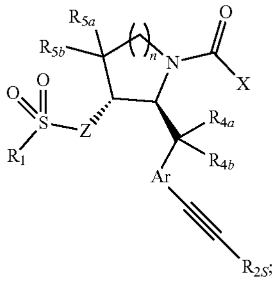

(II-4)

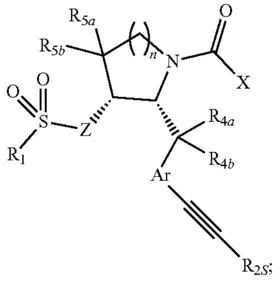

or a pharmaceutically acceptable salt thereof.

In some embodiments, the compound is of Formula (III-a) or (III-b):

(III-a)

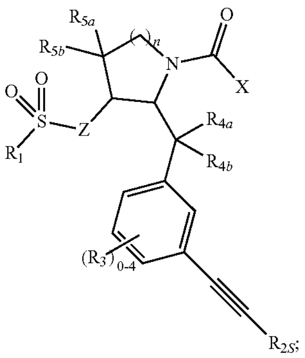

(III-b)

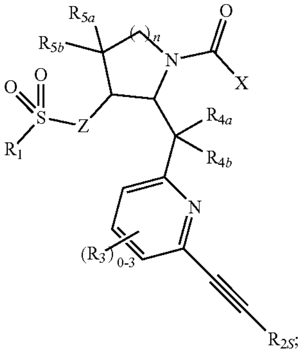

or a pharmaceutically acceptable salt thereof.

In some embodiments, the compound is of Formula (IV-a) or (IV-b):

(IV-a)

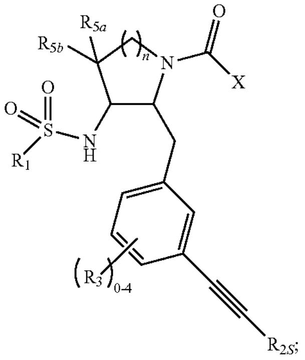

-continued (IV-b)

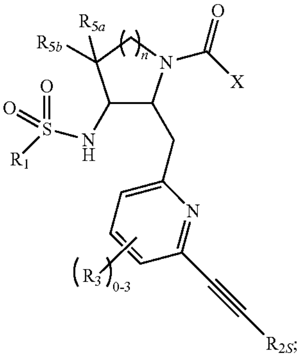

or a pharmaceutically acceptable salt thereof.

In some embodiments, the compound is selected from the compounds described in Table 1 and pharmaceutically acceptable salts thereof.

In some embodiments, the compound is selected from the compounds described in Table 2 and pharmaceutically acceptable salts thereof.

TABLE 1

| Compound No. | Structure |
| --- | --- |
| 1-1 | 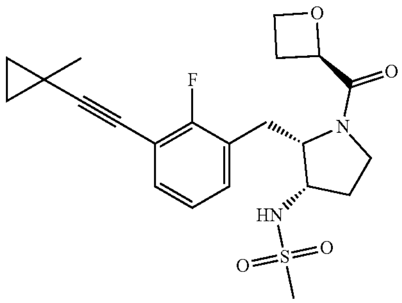 [SMILES: CC1(C#Cc2cccc(C[C@H]3[C@@H](NS(C)(=O)=O)CCN3C(=O)[C@H]3CCO3)c2F)CC1] |
| 1-2 | 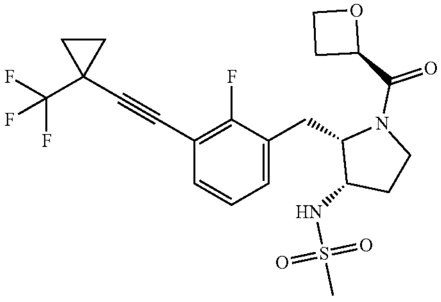 [SMILES: CS(=O)(=O)N[C@H]1CCN(C(=O)[C@H]2CCO2)[C@H]1Cc1cccc(C#CC2(C(F)(F)F)CC2)c1F] |
| 1-3 | 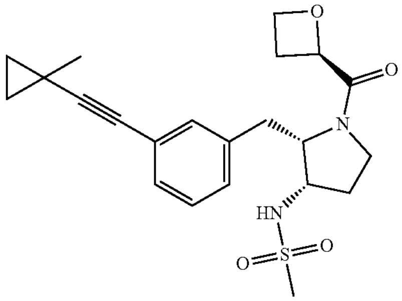 [SMILES: CC1(C#Cc2cccc(C[C@H]3[C@@H](NS(C)(=O)=O)CCN3C(=O)[C@H]3CCO3)c2)CC1] |

TABLE 1-continued
| Compound No. | Structure |
|---|---|
| 1-4 | 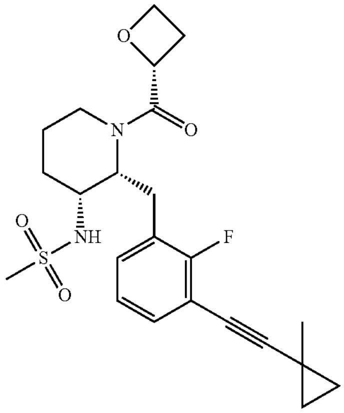 [SMILES: CC1(C#Cc2cccc(C[C@@H]3[C@H](NS(C)(=O)=O)CCCN3C(=O)[C@H]3CCO3)c2F)CC1] |
| 1-5 | 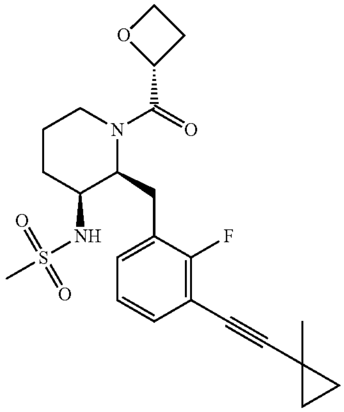 [SMILES: CC1(C#Cc2cccc(C[C@H]3[C@@H](NS(C)(=O)=O)CCCN3C(=O)[C@H]3CCO3)c2F)CC1] |
| 1-6 | 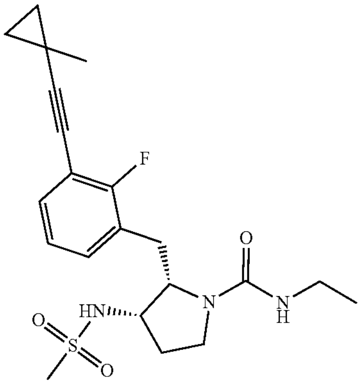 [SMILES: CCNC(=O)N1CC[C@H](NS(C)(=O)=O)[C@@H]1Cc1cccc(C#CC2(C)CC2)c1F] |
| 1-7 | 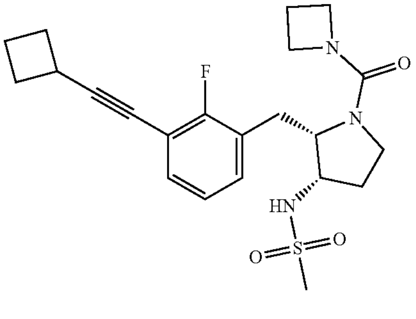 [SMILES: CS(=O)(=O)N[C@H]1CCN(C(=O)N2CCC2)[C@H]1Cc1cccc(C#CC2CCC2)c1F] |
TABLE 1-continued
| Compound No. | Structure |
|---|---|
| 1-8 | 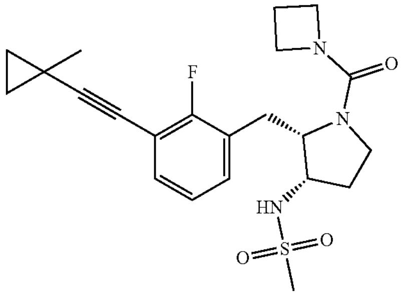 [SMILES: CC1(C#Cc2cccc(C[C@H]3[C@@H](NS(C)(=O)=O)CCN3C(=O)N3CCC3)c2F)CC1] |
| 1-9 | 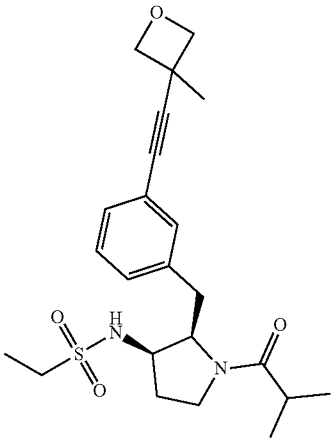 [SMILES: CCS(=O)(=O)N[C@@H]1CCN(C(=O)C(C)C)[C@@H]1Cc1cccc(C#CC2(C)COC2)c1] |
| 1-10 | 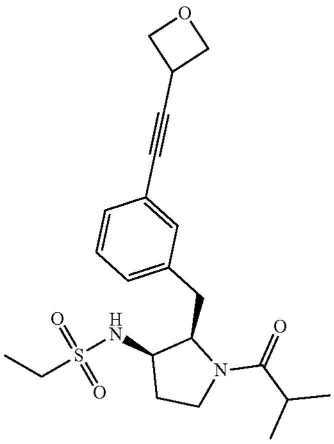 [SMILES: CCS(=O)(=O)N[C@@H]1CCN(C(=O)C(C)C)[C@@H]1Cc1cccc(C#CC2COC2)c1] |
| 1-11 | 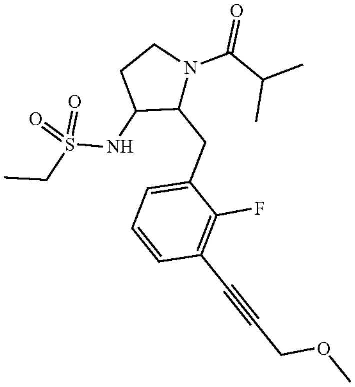 [SMILES: CCS(=O)(=O)NC1CCN(C(=O)C(C)C)C1Cc1cccc(C#CCOC)c1F] |

TABLE 1-continued
| Compound No. | Structure |
| --- | --- |
| 1-12 | 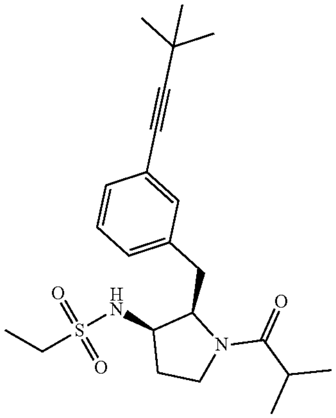 [SMILES: CCS(=O)(=O)N[C@@H]1CCN(C(=O)C(C)C)[C@@H]1Cc1cccc(C#CC(C)(C)C)c1] |
| 1-13 | 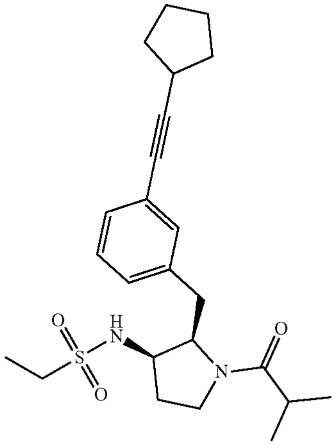 [SMILES: CCS(=O)(=O)N[C@@H]1CCN(C(=O)C(C)C)[C@@H]1Cc1cccc(C#CC2CCCC2)c1] |
| 1-14 | 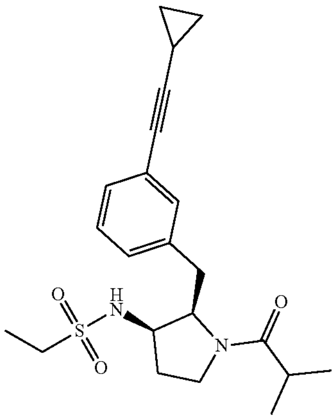 [SMILES: CCS(=O)(=O)N[C@@H]1CCN(C(=O)C(C)C)[C@@H]1Cc1cccc(C#CC2CC2)c1] |
| 1-15 | 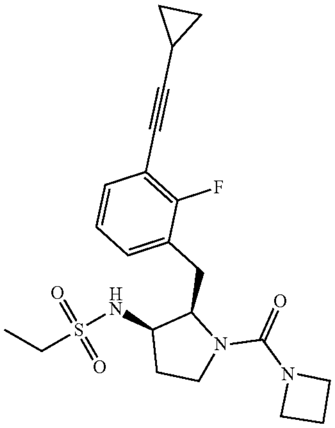 [SMILES: CCS(=O)(=O)N[C@@H]1CCN(C(=O)N2CCC2)[C@@H]1Cc1cccc(C#CC2CC2)c1F] |
| 1-16 | 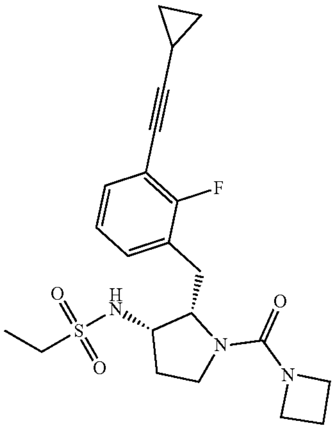 [SMILES: CCS(=O)(=O)N[C@H]1CCN(C(=O)N2CCC2)[C@H]1Cc1cccc(C#CC2CC2)c1F] |
| 1-17 | 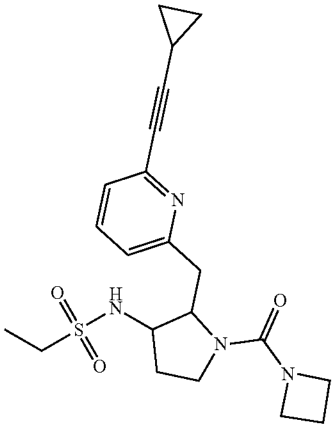 [SMILES: CCS(=O)(=O)NC1CCN(C(=O)N2CCC2)C1Cc1cccc(C#CC2CC2)n1] |

TABLE 1-continued
| Compound No. | Structure |
|---|---|
| 1-18 | 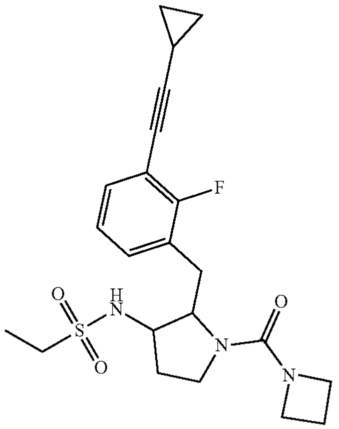 [SMILES: CCS(=O)(=O)NC1CCN(C(=O)N2CCC2)C1Cc1cccc(C#CC2CC2)c1F] |
| 1-19 | 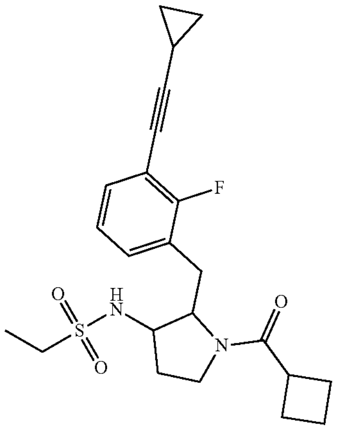 [SMILES: CCS(=O)(=O)NC1CCN(C(=O)C2CCC2)C1Cc1cccc(C#CC2CC2)c1F] |
| 1-20 | 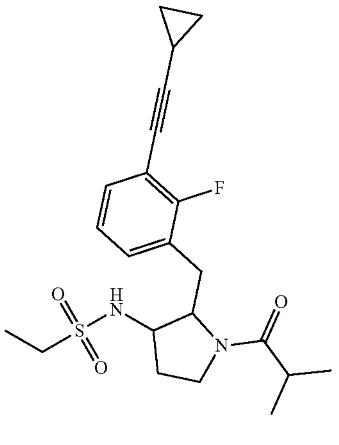 [SMILES: CCS(=O)(=O)NC1CCN(C(=O)C(C)C)C1Cc1cccc(C#CC2CC2)c1F] |
TABLE 1-continued
| Compound No. | Structure |
|---|---|
| 1-21 | 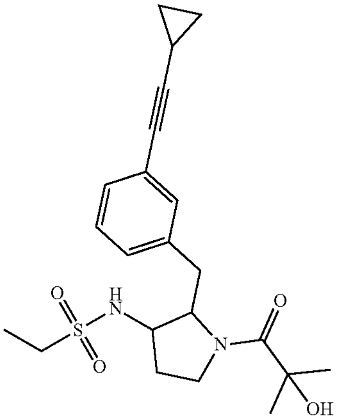 [SMILES: CCS(=O)(=O)NC1CCN(C(=O)C(C)(C)O)C1Cc1cccc(C#CC2CC2)c1] |
| 1-22 | 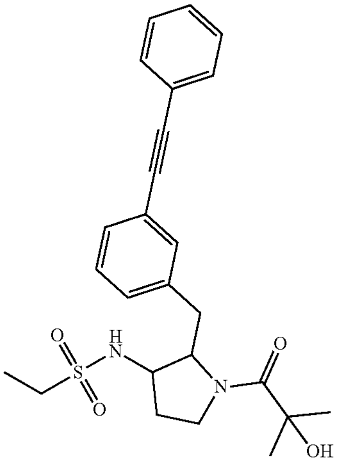 [SMILES: CCS(=O)(=O)NC1CCN(C(=O)C(C)(C)O)C1Cc1cccc(C#Cc2ccccc2)c1] |
TABLE 2
| Compound No. | Structure |
|---|---|
| 2-1 | 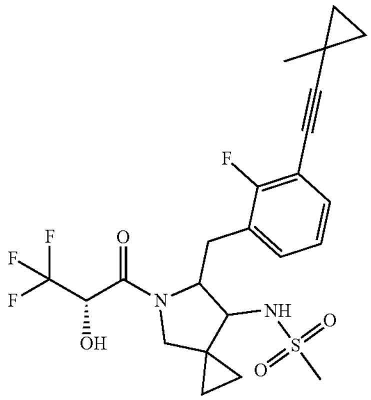 [SMILES: CC1(C#Cc2cccc(CC3C(NS(C)(=O)=O)C4(CC4)CN3C(=O)[C@H](O)C(F)(F)F)c2F)CC1] |

TABLE 2-continued
| Compound No. | Structure |
|---|---|
| 2-2 | 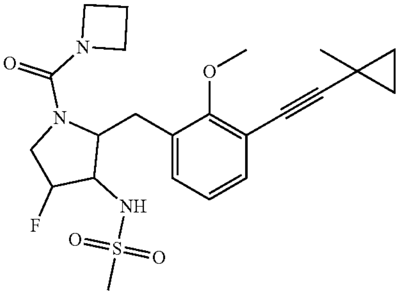 [SMILES: COc1c(C#CC2(C)CC2)cccc1CC1C(NS(C)(=O)=O)C(F)CN1C(=O)N1CCC1] |
| 2-3 | 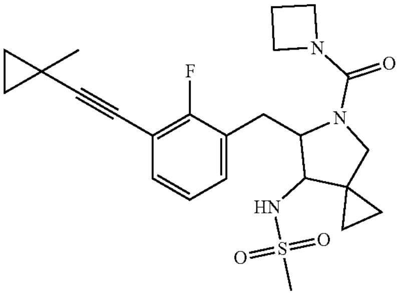 [SMILES: CC1(C#Cc2cccc(CC3C(NS(C)(=O)=O)C4(CC4)CN3C(=O)N3CCC3)c2F)CC1] |
| 2-4 | 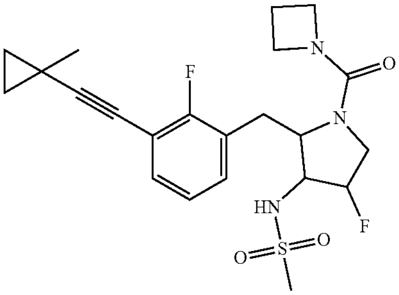 [SMILES: CC1(C#Cc2cccc(CC3C(NS(C)(=O)=O)C(F)CN3C(=O)N3CCC3)c2F)CC1] |
| 2-5 | 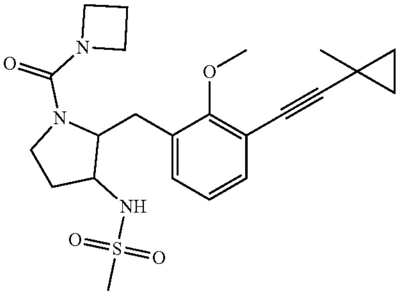 [SMILES: COc1c(C#CC2(C)CC2)cccc1CC1C(NS(C)(=O)=O)CCN1C(=O)N1CCC1] |
| 2-6 | 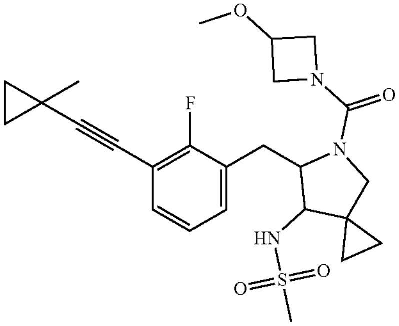 [SMILES: COC1CN(C(=O)N2CC3(CC3)C(NS(C)(=O)=O)C2Cc2cccc(C#CC3(C)CC3)c2F)C1] |
TABLE 2-continued
| Compound No. | Structure |
|---|---|
| 2-7 | 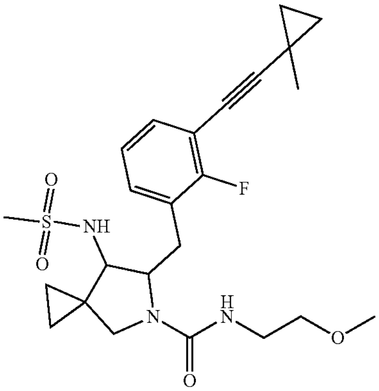 |
| 2-8 | 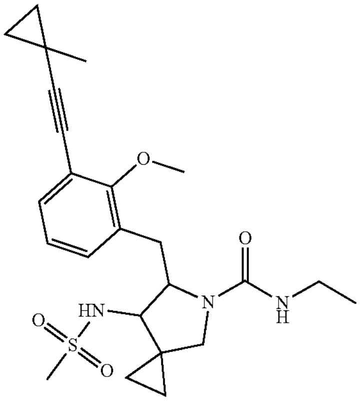 [SMILES: CCNC(=O)N1CC2(CC2)C(NS(C)(=O)=O)C1Cc1cccc(C#CC2(C)CC2)c1OC] |
| 2-9 | 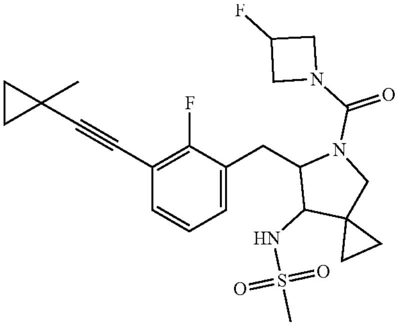 [SMILES: CC1(C#Cc2cccc(CC3C(NS(C)(=O)=O)C4(CC4)CN3C(=O)N3CC(F)C3)c2F)CC1] |
| 2-10 | 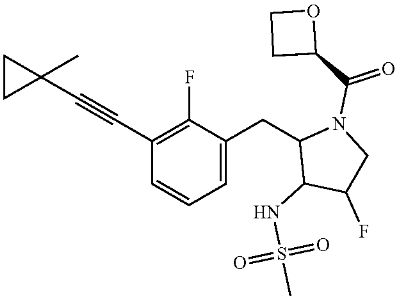 [SMILES: CC1(C#Cc2cccc(CC3C(NS(C)(=O)=O)C(F)CN3C(=O)[C@H]3CCO3)c2F)CC1] |

TABLE 2-continued
| Compound No. | Structure |
|---|---|
| 2-11 | 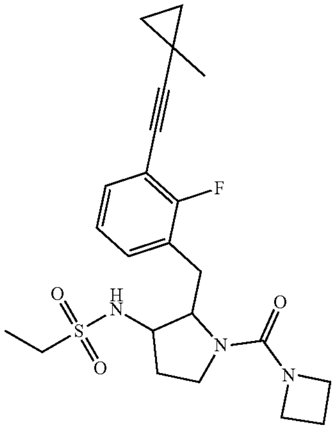 [SMILES: CCS(=O)(=O)NC1CCN(C(=O)N2CCC2)C1Cc1cccc(C#CC2(C)CC2)c1F] |
| 2-12 | 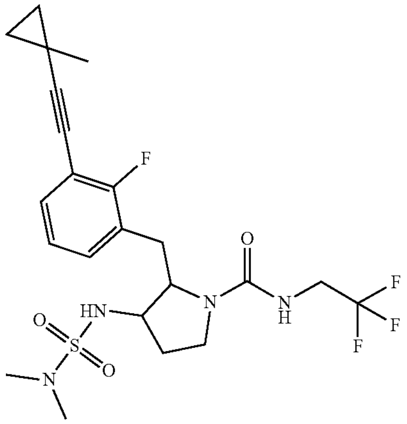 [SMILES: CN(C)S(=O)(=O)NC1CCN(C(=O)NCC(F)(F)F)C1Cc1cccc(C#CC2(C)CC2)c1F] |
| 2-13 | 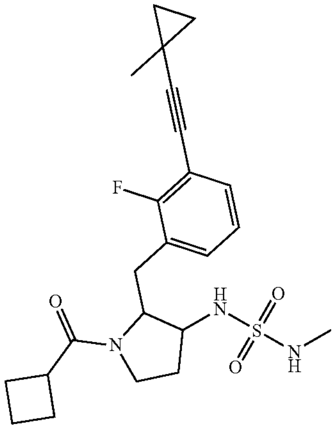 [SMILES: CNS(=O)(=O)NC1CCN(C(=O)C2CCC2)C1Cc1cccc(C#CC2(C)CC2)c1F] |
TABLE 2-continued
| Compound No. | Structure |
|---|---|
| 2-14 | 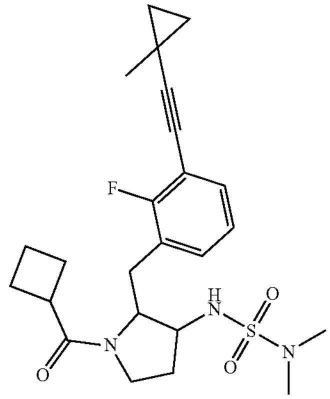 [SMILES: CN(C)S(=O)(=O)NC1CCN(C(=O)C2CCC2)C1Cc1cccc(C#CC2(C)CC2)c1F] |
| 2-15 | 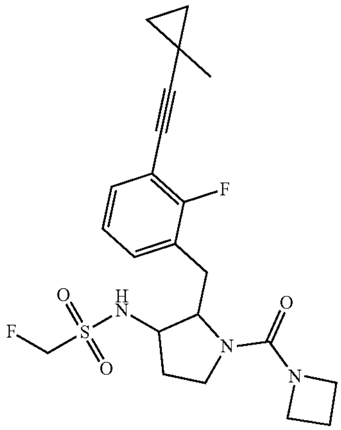 [SMILES: CC1(C#Cc2cccc(CC3C(NS(=O)(=O)CF)CCN3C(=O)N3CCC3)c2F)CC1] |
| 2-16 | 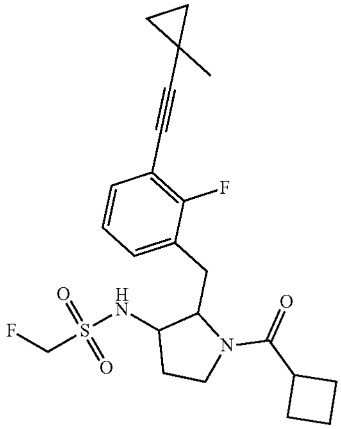 [SMILES: CC1(C#Cc2cccc(CC3C(NS(=O)(=O)CF)CCN3C(=O)C3CCC3)c2F)CC1] |

TABLE 2-continued
| Compound No. | Structure |
|---|---|
| 2-17 | 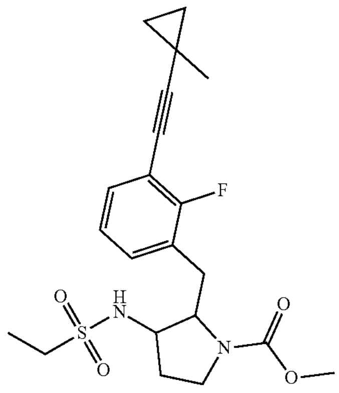 [SMILES: CCS(=O)(=O)NC1CCN(C(=O)OC)C1Cc1cccc(C#CC2(C)CC2)c1F] |
| 2-18 | 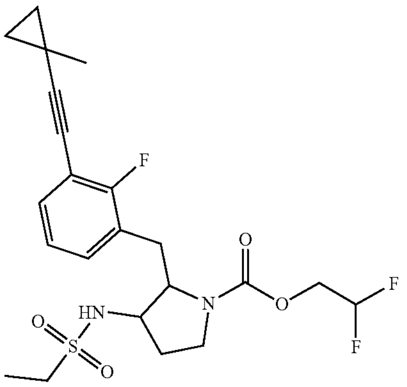 [SMILES: CCS(=O)(=O)NC1CCN(C(=O)OCC(F)F)C1Cc1cccc(C#CC2(C)CC2)c1F] |
| 2-19 | 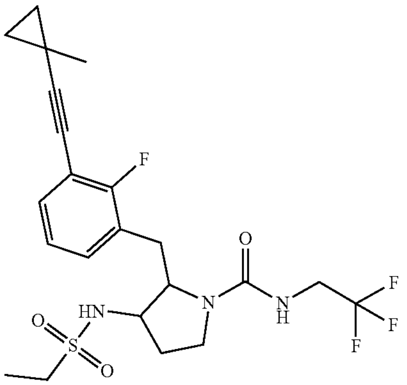 [SMILES: CCS(=O)(=O)NC1CCN(C(=O)NCC(F)(F)F)C1Cc1cccc(C#CC2(C)CC2)c1F] |
| 2-20 | 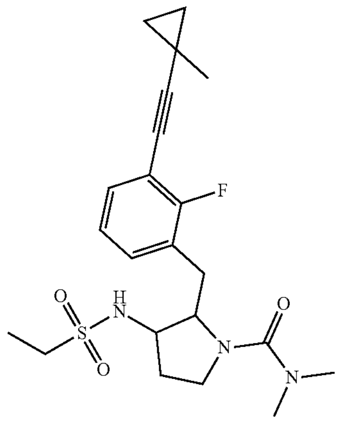 [SMILES: CCS(=O)(=O)NC1CCN(C(=O)N(C)C)C1Cc1cccc(C#CC2(C)CC2)c1F] |
TABLE 2-continued
| Compound No. | Structure |
|---|---|
| 2-21 | 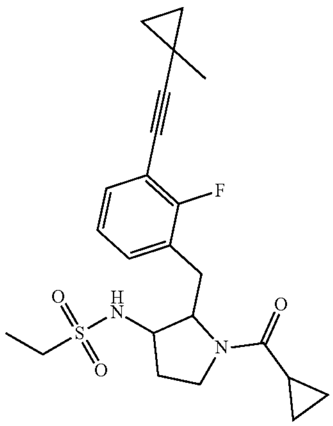 [SMILES: CCS(=O)(=O)NC1CCN(C(=O)C2CC2)C1Cc1cccc(C#CC2(C)CC2)c1F] |
| 2-22 | 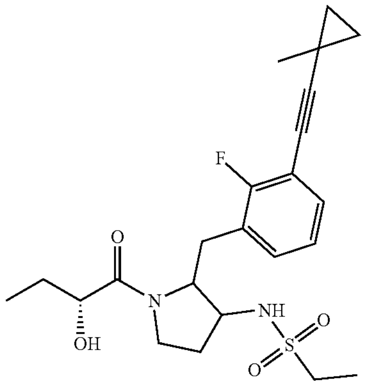 [SMILES: CC[C@@H](O)C(=O)N1CCC(NS(=O)(=O)CC)C1Cc1cccc(C#CC2(C)CC2)c1F] |
| 2-23 | 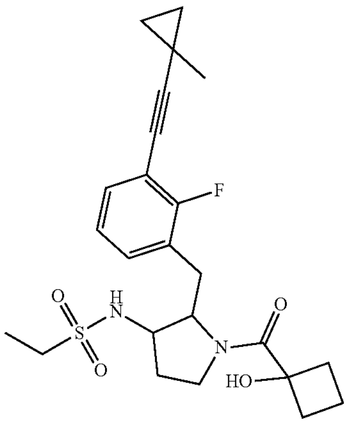 [SMILES: CCS(=O)(=O)NC1CCN(C(=O)C2(O)CCC2)C1Cc1cccc(C#CC2(C)CC2)c1F] |

TABLE 2-continued

| Compound No. | Structure |
| --- | --- |
| 2-24 | 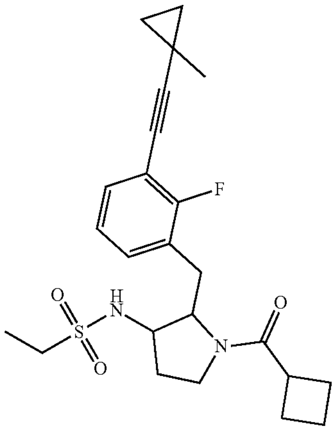 |
| 2-25 | 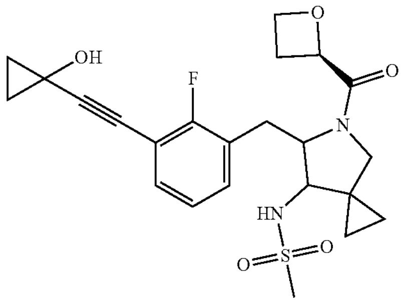 [SMILES: CS(=O)(=O)NC1C(Cc2cccc(C#CC3(O)CC3)c2F)N(C(=O)[C@H]2CCO2)CC12CC2] |
| 2-26 | 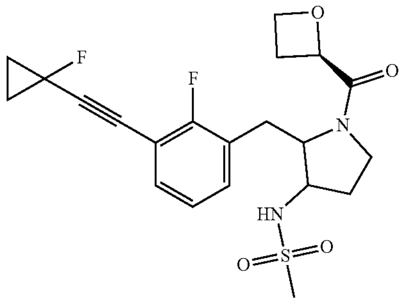 [SMILES: CS(=O)(=O)NC1CCN(C(=O)[C@H]2CCO2)C1Cc1cccc(C#CC2(F)CC2)c1F] |
| 2-27 | 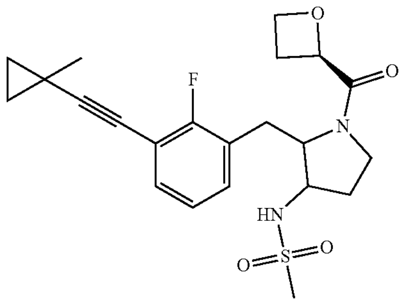 [SMILES: CC1(C#Cc2cccc(CC3C(NS(C)(=O)=O)CCN3C(=O)[C@H]3CCO3)c2F)CC1] |
| 2-28 | 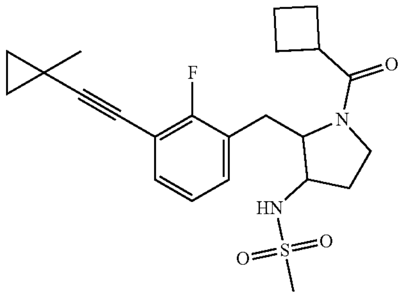 [SMILES: CC1(C#Cc2cccc(CC3C(NS(C)(=O)=O)CCN3C(=O)C3CCC3)c2F)CC1] |
| 2-29 | 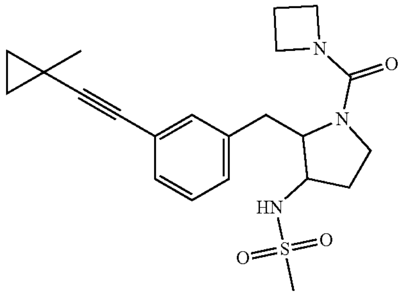 [SMILES: CC1(C#Cc2cccc(CC3C(NS(C)(=O)=O)CCN3C(=O)N3CCC3)c2)CC1] |
| 2-30 | 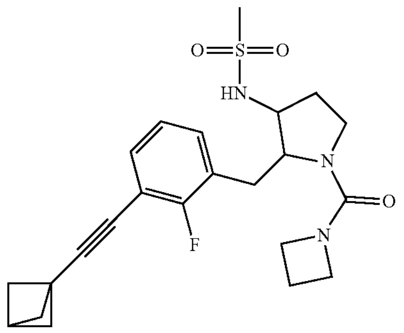 [SMILES: CS(=O)(=O)NC1CCN(C(=O)N2CCC2)C1Cc1cccc(C#CC23CC(C2)C3)c1F] |

In some embodiments, the compound is a pharmaceutically acceptable salt of any one of the compounds described in Tables 1 and 2.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Tables 1 and 2 and prodrugs and pharmaceutically acceptable salts thereof.

In some embodiments, the compound is an isotopic derivative of any one of the compounds described in Tables 1 and 2 and pharmaceutically acceptable salts thereof.

In some embodiments, the compound is an isotopic derivative of any one of prodrugs of the compounds described in Tables 1 and 2 and pharmaceutically acceptable salts thereof.

In some embodiments, the compound is an isotopic derivative of any one of the compounds described in Tables 1 and 2.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) is isotopically enriched with regard to, or labelled with, one or more isotopes as compared to the corresponding compound of Formula (I). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof). In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof. In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognised techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{32}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt itis to be understood that, where in this specification a group is qualified by "described herein", the said group encompasses the first occurring and broadest definition as well as each and all of the particular definitions for that group.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof, while the presentation further intends to refer to the specific configuration of the compound. For example, when a compound is presented with a moiety of

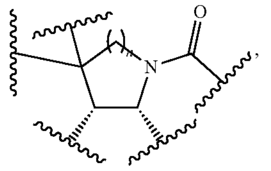

the presentation may intend to encompass, and to refer to, the compound with cis-configuration, e.g.,

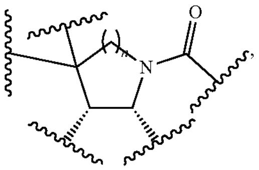

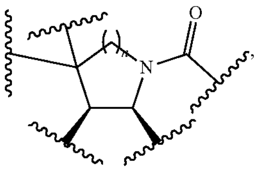

or a mixture thereof. In some embodiments, when the compound structure is described as "cis racemic", the presentation intends to refer to a mixture of the compound with cis-configuration of the moiety, e.g., the mixture of

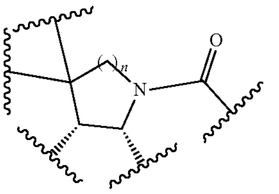

and

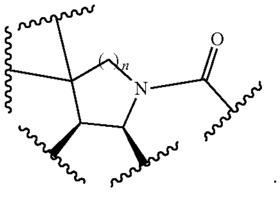

.

It will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof. For example, when a compound is presented with a moiety of

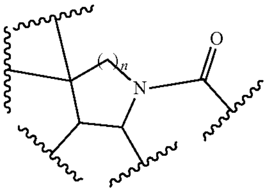

, the presentation may intend to encompass, and to refer to, the compound with the moiety of

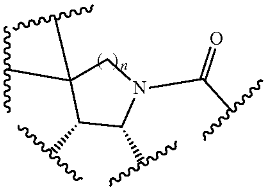

,

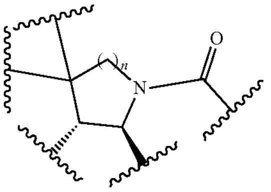

,

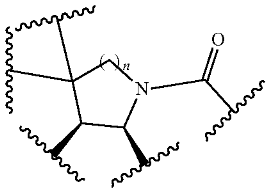

, or

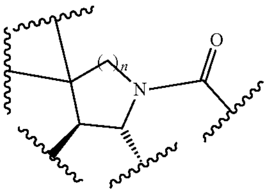

, or any mixture thereof. Further, the presentation may intend to encompass, and to refer to, the compound with cis-configuration, e.g.,

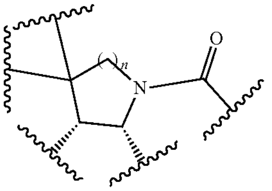

,

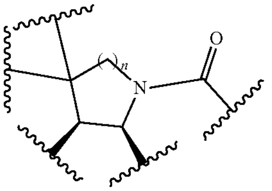

, or a mixture thereof. In some embodiments, when the compound structure is described as "cis racemic", the presentation intends to refer to a mixture of the compound with cis-configuration of the moiety, e.g., the mixture of

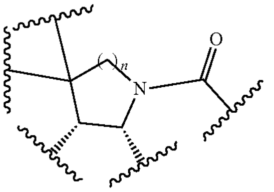

and

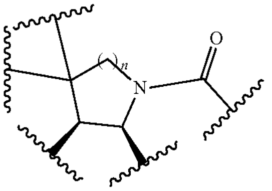

.

As used herein, the term "isomerism" means compounds that have identical molecular formulae but differ in the sequence of bonding of their atoms or in the arrangement of their atoms in space. Isomers that differ in the arrangement of their atoms in space are termed"stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew.* Chem. 1966, 78,413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of anyone of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

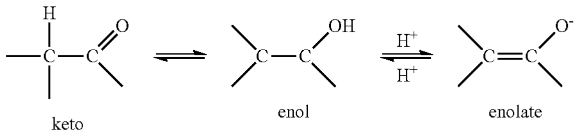

Compounds of any one of the Formulae disclosed herein containing an amine function may also form N-oxides. A reference herein to a compound of Formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

Accordingly, the present disclosure includes those compounds of any one of the Formulae disclosed herein as defined herein before when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of anyone of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Prodrugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77,285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of anyone of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of anyone of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of anyone of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a persons killed in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesised by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof, and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Scheme 1 herein.

Scheme 1

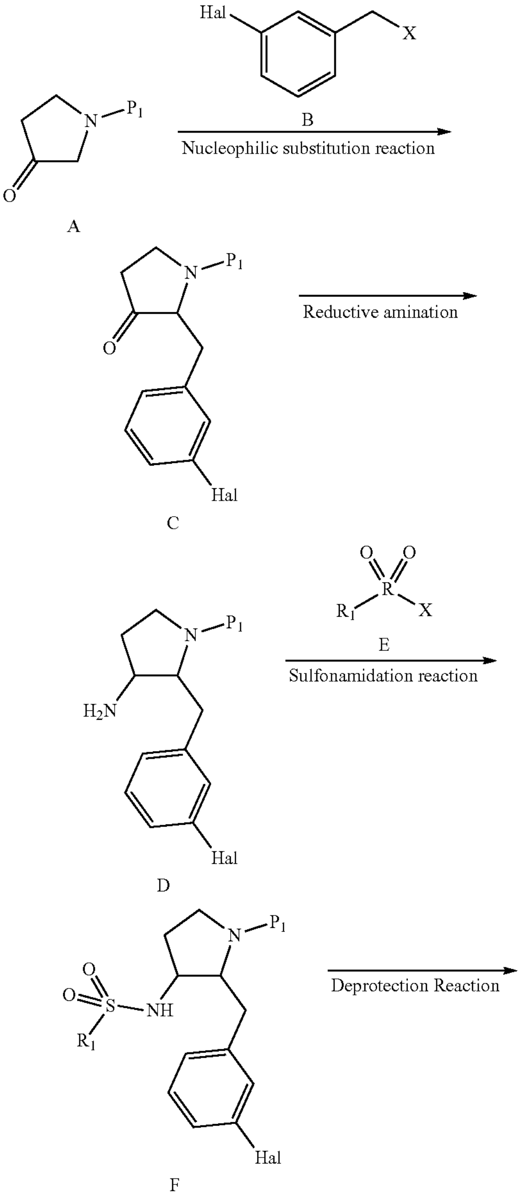

-continued

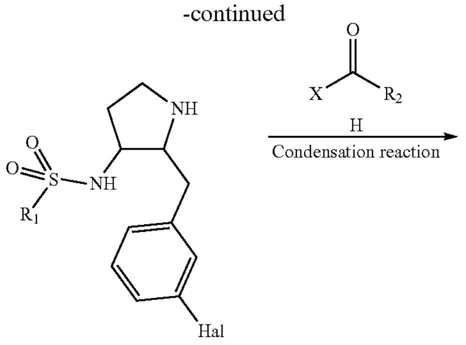

G

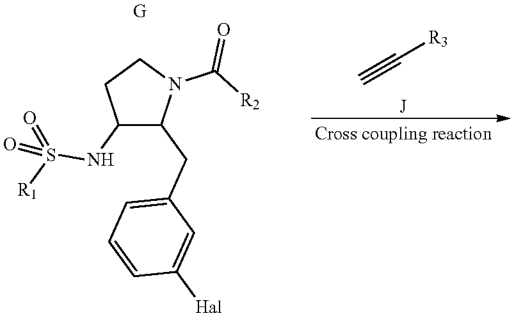

I

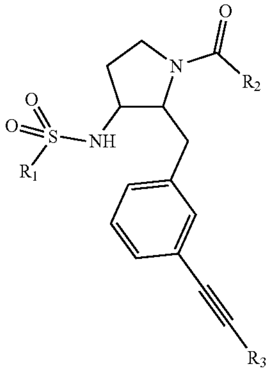

K

Examples of the protecting group $P_1$ for an amino group include, but are not limited to, carbamate-type protecting groups such as tert-butyl carbamate and the like. Examples of the leaving group X include halogens, in particular bromine or iodine, or sulfonate esters such as methyl sulfonate.

Compound C can be produced by subjecting compound A to a nucleophilic substitution reaction with Compound B in the presence of abase. Examples of the base include lithium amides and the like. Alternatively, compound C can also be produced by conversion of compound A to the corresponding enamine, and then reacting the enamine with compound B. Examples of the amine that can be used for the enamine formation include, but are not limited to, pyrrolidine.

Compound D can be produced by subjecting Compound C to a reductive amination reaction. Examples of the amine used include ammonium salts such as ammonium formate and the like. Examples of the reducing agent include sodium triacetoxyborohydride, sodium cyanoborohydride, hydrogen and formic acid and the like. In addition, a metal catalyst may be added to the reaction system. Examples of the catalyst to be used include iridium catalysts and the like.

Compound F can be produced by subjecting Compound D to a sulfonamidation reaction with Compound E in the presence of a base. Compound E may be commercially available or can be produced from known methods. Examples of the base to be used include organic bases such as tertiary alkyl amines such as N,N-diisopropylethylamine and the like.

Compound G can be prepared by subjecting Compound F to a deprotection reaction to remove protecting group $P_1$. The specific deprotection reaction will depend on the choice of protecting group. In the case where $P_1$ is tert-butyl carbamate the deprotection can be achieved by treatment with an acid such as hydrochloric acid or trifluoroacetic acid and the like.

Compound I can be prepared by subjecting Compound G and Compound H to a condensation reaction. Examples of Compound H include acyl halides such as acid chlorides, alkyl chloroformates, carbamoyl chlorides and the like; activated carboxylic acids such as acid anhydrides, activated esters and the like. Examples of the activating agent for carboxylic acids include carbodiimide condensing agents, carbonate ester condensing agents such as 1,1-carbonyldiimidazole (CDI) and the like; benzotriazole-1-yloxy-tris-dimethylaminophosphonium salt (BOP reagent), alkyl chloroformates; O-(7-azabenzotriazol-1-yl)-N,N,N',N'-tetramethyluronium hexafluorophosphate (HATU) and the like). When a condensing agent is used, an additive such as 1-hydroxybenzotriazole (HOBt) or dimethylaminopyridine (DMAP) may be added to the reaction system.

Compound K can be prepared by subjecting compound I and an appropriate acetylene (J), available commercially or according to a known method, to Sonogashira type cross-coupling reaction using a metal catalyst. Examples of the metal catalyst to be used include palladium compounds such as palladium(II) acetate, tetrakis(triphenylphosphine)palladium(O), dichlorobis(triphenylphosphine)palladium(II), Bis (acetonitrile)dichloropalladium(II) and the like. A phosphine ligand can also be added to the reaction system such as 2-Dicyclohexylphosphino-2',4',6'triisopropylbiphenyl (XPhos), 2-Dicyclohexylphosphino-2',6'-dimethoxybiphenyl (SPhos) and the like. In addition, a base can be added to the reaction system, and examples thereof include inorganic bases and the like.

Compound K obtained by the above-mentioned method can be isolated and purified by a known means, such as solvent extraction, phase transfer, crystallization, chromatography and the like.

When Compound K contains optical isomers, stereoisomers and rotamers, these compounds are also included in Compound K, and each can be obtained by a synthesis method or a separation method. For example, when an optical isomer exists in Compound K, an optical isomer resolved from the compound is also encompassed in Compound K.

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Despite orexin cell loss and decreased orexin peptides in cerebrospinal fluid in NT1, orexin receptors on postsynaptic neurons remain intact as suitable targets for pharmacotherapeutic intervention. The orexin peptides A and B (OXA and OXB) may be cleaved from a single precursor molecule (prepro-orexin) that is produced exclusively in the lateral hypothalamus. Both orexin peptides bind with similar high affinity to OX2R, but the orexin-1 receptor (OX1R) may be preferentially bound by OXA. Postsynaptic excitation of these G-protein coupled orexin receptors may stimulate the release of monoaminergic and cholinergic neurotransmitters that promote wakefulness and inhibitory neurotransmitters that suppress REM sleep atonia.

In some embodiments, the assay uses cells stably expressing either human orexin type 2 or human orexin type 1 receptor. In some embodiments, the cells are obtained by inserting the Orexin receptor cDNA into pcDNA3.1(+) plasmid vector, identifying clones by G418 drug resistance selection, and/or growing a single clone for OX2R-CHO and OX1R-CHO in bulk. In some embodiments, the assay was detected using Fluorescent Imaging Plate Reader TETRA (FLIPR TETRA: manufactured by Molecular Devices). In some embodiments, the agonist activity of the test compound was calculated assuming that the fluorescence value of the well added with only the dilution buffer was 0% and the fluorescence value of the well added with 10 nM human orexin A (Tocris) buffer was 100%.

In some embodiments, the biological assay is described in the Examples herein.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Tables 1 and 2.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of modulating orexin-2 receptor activity (e.g., in vitro or in vivo), comprising contacting a cell with an effective amount of a compound of the present disclosure or a pharmaceutically acceptable salt thereof.

In some aspects, the present disclosure provides a method of modulating orexin-2 receptor activity (e.g., in vitro or in vivo), comprising contacting a cell with a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a disease or disorder disclosed herein in a subject in need thereof, comprising administering to the subject a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a compound of the present disclosure or a pharmaceutically acceptable salt thereof, or a pharmaceutical composition of the present disclosure.

In some embodiments, the disease or disorder is associated with an implicated orexin-2 receptor activity. In some embodiments, the disease or disorder is a disease or disorder in which orexin-2 receptor activity is implicated.

In some embodiments, the disease or disorder is a neurodegenerative disorder, a symptom of a rare genetic disorder, a mental health disorder, a metabolic syndrome, osteoporosis, cardiac failure, coma, or a complication in emergence from anesthesia.

In some aspects, the present disclosure provides a method of treating or preventing a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a symptom of a rare genetic disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a mental health disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a metabolic syndrome in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing osteoporosis in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cardiac failure in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing coma in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a neurodegenerative disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a symptom of a rare genetic disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a mental health disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a metabolic syndrome in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating osteoporosis in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating cardiac failure in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating coma in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a compound of the present disclosure or a pharmaceutically acceptable salt thereof, or a pharmaceutical composition of the present disclosure.

In some aspects, the present disclosure provides a method of treating a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing a neurodegenerative disorder in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing a symptom of a rare genetic disorder in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing a mental health disorder in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing a metabolic syndrome in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing osteoporosis in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing cardiac failure in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing coma in a subject in need thereof, comprising administering to the subject a compound of the present disclosure or a pharmaceutically acceptable salt thereof, or a pharmaceutical composition of the present disclosure.

In some aspects, the present disclosure provides a method of treating or preventing a complication in emergence from anesthesia in a subject in need thereof, comprising administering to the subject a compound of the present disclosure or a pharmaceutically acceptable salt thereof, or a pharmaceutical composition of the present disclosure.

In some aspects, the present disclosure provides a method of treating a neurodegenerative disorder in a subject in need thereof, comprising administering to the subject a compound of the present disclosure or a pharmaceutically acceptable salt thereof, or a pharmaceutical composition of the present disclosure.

In some aspects, the present disclosure provides a method of treating a symptom of a rare genetic disorder in a subject in need thereof, comprising administering to the subject a compound of the present disclosure or a pharmaceutically acceptable salt thereof, or a pharmaceutical composition of the present disclosure.

In some aspects, the present disclosure provides a method of treating a mental health disorder in a subject in need thereof, comprising administering to the subject a compound of the present disclosure or a pharmaceutically acceptable salt thereof, or a pharmaceutical composition of the present disclosure.

In some aspects, the present disclosure provides a method of treating a metabolic syndrome in a subject in need thereof, comprising administering to the subject a compound of the present disclosure or a pharmaceutically acceptable salt thereof, or a pharmaceutical composition of the present disclosure.

In some aspects, the present disclosure provides a method of treating osteoporosis in a subject in need thereof, comprising administering to the subject a compound of the present disclosure or a pharmaceutically acceptable salt thereof, or a pharmaceutical composition of the present disclosure.

In some aspects, the present disclosure provides a method of treating cardiac failure in a subject in need thereof, comprising administering to the subject a compound of the present disclosure or a pharmaceutically acceptable salt thereof, or a pharmaceutical composition of the present disclosure.

In some aspects, the present disclosure provides a method of treating coma in a subject in need thereof, comprising administering to the subject a compound of the present disclosure or a pharmaceutically acceptable salt thereof, or a pharmaceutical composition of the present disclosure.

In some aspects, the present disclosure provides a method of treating a complication in emergence from anesthesia in a subject in need thereof, comprising administering to the subject a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating orexin-2 receptor activity (e.g, in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides a compound of the present disclosure or a pharmaceutically acceptable salt thereof for use in treating or preventing a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides a compound of the present disclosure or a pharmaceutically acceptable salt thereof for use in treating or preventing a neurodegenerative disorder in a subject in need thereof.

In some aspects, the present disclosure provides a compound of the present disclosure or a pharmaceutically acceptable salt thereof for use in treating or preventing a symptom of a rare genetic disorder in a subject in need thereof.

In some aspects, the present disclosure provides a compound of the present disclosure or a pharmaceutically acceptable salt thereof for use in treating or preventing a mental health disorder in a subject in need thereof.

In some aspects, the present disclosure provides a compound of the present disclosure or a pharmaceutically acceptable salt thereof for use in treating or preventing a metabolic syndrome in a subject in need thereof.

In some aspects, the present disclosure provides a compound of the present disclosure or a pharmaceutically acceptable salt thereof for use in treating or preventing osteoporosis in a subject in need thereof.

In some aspects, the present disclosure provides a compound of the present disclosure or a pharmaceutically acceptable salt thereof for use in treating or preventing cardiac failure in a subject in need thereof.

In some aspects, the present disclosure provides a compound of the present disclosure or a pharmaceutically acceptable salt thereof for use in treating or preventing coma in a subject in need thereof.

In some aspects, the present disclosure provides a compound of the present disclosure or a pharmaceutically acceptable salt thereof for use in treating or preventing a complication in emergence from anesthesia in a subject in need thereof.

In some aspects, the present disclosure provides a compound of the present disclosure or a pharmaceutically acceptable salt thereof for use in treating a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides a compound of the present disclosure or a pharmaceutically acceptable salt thereof for use in treating a neurodegenerative disorder in a subject in need thereof.

In some aspects, the present disclosure provides a compound of the present disclosure or a pharmaceutically acceptable salt thereof for use in treating a symptom of a rare genetic disorder in a subject in need thereof.

In some aspects, the present disclosure provides a compound of the present disclosure or a pharmaceutically acceptable salt thereof for use in treating a mental health disorder in a subject in need thereof.

In some aspects, the present disclosure provides a compound of the present disclosure or a pharmaceutically acceptable salt thereof for use in treating a metabolic syndrome in a subject in need thereof.

In some aspects, the present disclosure provides a compound of the present disclosure or a pharmaceutically acceptable salt thereof for use in treating osteoporosis in a subject in need thereof.

In some aspects, the present disclosure provides a compound of the present disclosure or a pharmaceutically acceptable salt thereof for use in treating cardiac failure in a subject in need thereof.

In some aspects, the present disclosure provides a compound of the present disclosure or a pharmaceutically acceptable salt thereof for use in treating coma in a subject in need thereof.

In some aspects, the present disclosure provides a compound of the present disclosure or a pharmaceutically acceptable salt thereof for use in treating a complication in emergence from anesthesia in a subject in need thereof.

In some aspects, the present disclosure provides use of a compound of the present disclosure or a pharmaceutically acceptable salt thereof in the manufacture of a medicament for modulating orexin-2 activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof in the manufacture of a medicament for treating or preventing a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides use of a compound of the present disclosure or a pharmaceutically acceptable salt thereof in the manufacture of a medicament for treating or preventing a neurodegenerative disorder in a subject in need thereof.

In some aspects, the present disclosure provides use of a compound of the present disclosure or a pharmaceutically acceptable salt thereof in the manufacture of a medicament for treating or preventing a symptom of a rare genetic disorder in a subject in need thereof.

In some aspects, the present disclosure provides use of a compound of the present disclosure or a pharmaceutically acceptable salt thereof in the manufacture of a medicament for treating or preventing a mental health disorder in a subject in need thereof.

In some aspects, the present disclosure provides use of a compound of the present disclosure or a pharmaceutically acceptable salt thereof in the manufacture of a medicament for treating or preventing a metabolic syndrome in a subject in need thereof.

In some aspects, the present disclosure provides use of a compound of the present disclosure or a pharmaceutically acceptable salt thereof in the manufacture of a medicament for treating or preventing osteoporosis in a subject in need thereof.

In some aspects, the present disclosure provides use of a compound of the present disclosure or a pharmaceutically acceptable salt thereof in the manufacture of a medicament for treating or preventing cardiac failure in a subject in need thereof.

In some aspects, the present disclosure provides use of a compound of the present disclosure or a pharmaceutically acceptable salt thereof in the manufacture of a medicament for treating or preventing coma in a subject in need thereof.

In some aspects, the present disclosure provides use of a compound of the present disclosure or a pharmaceutically acceptable salt thereof in the manufacture of a medicament for treating or preventing a complication in emergence from anesthesia in a subject in need thereof.

In some aspects, the present disclosure provides use of a compound of the present disclosure or a pharmaceutically acceptable salt thereof in the manufacture of a medicament for treating a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides use of a compound of the present disclosure or a pharmaceutically acceptable salt thereof in the manufacture of a medicament for treating a neurodegenerative disorder in a subject in need thereof.

In some aspects, the present disclosure provides use of a compound of the present disclosure or a pharmaceutically acceptable salt thereof in the manufacture of a medicament for treating a symptom of a rare genetic disorder in a subject in need thereof.

In some aspects, the present disclosure provides use of a compound of the present disclosure or a pharmaceutically acceptable salt thereof in the manufacture of a medicament for treating a mental health disorder in a subject in need thereof.

In some aspects, the present disclosure provides use of a compound of the present disclosure or a pharmaceutically acceptable salt thereof in the manufacture of a medicament for treating a metabolic syndrome in a subject in need thereof.

In some aspects, the present disclosure provides use of a compound of the present disclosure or a pharmaceutically acceptable salt thereof in the manufacture of a medicament for treating osteoporosis in a subject in need thereof.

In some aspects, the present disclosure provides use of a compound of the present disclosure or a pharmaceutically acceptable salt thereof in the manufacture of a medicament for treating cardiac failure in a subject in need thereof.

In some aspects, the present disclosure provides use of a compound of the present disclosure or a pharmaceutically acceptable salt thereof in the manufacture of a medicament for treating coma in a subject in need thereof.

In some aspects, the present disclosure provides use of a compound of the present disclosure or a pharmaceutically acceptable salt thereof in the manufacture of a medicament for treating a complication in emergence from anesthesia in a subject in need thereof.

The present disclosure provides compounds that function as modulators of orexin-2 receptor activity.

In some embodiments, the compounds of the present disclosure are agonists of the orexin-2 receptor.

Effectiveness of compounds of the disclosure can be determined by industry-accepted assays/disease models according to standard practices of elucidating the same as described in the art and are found in the current general knowledge.

The present disclosure also provides a method of treating a disease or disorder in which orexin-2 receptor activity is implicated in a patient in need of such treatment, said method comprising administering to said patient a therapeutically effective amount of a compound, or a pharmaceutically acceptable salt thereof, or a pharmaceutical composition as defined herein.

The present disclosure also provides a method of treating a disease or disorder in which orexin-2 receptor activity is implicated in a patient in need of such treatment, said method comprising administering to said patient a compound, or a pharmaceutically acceptable salt thereof, or a pharmaceutical composition as defined herein.

In some embodiments, the disease or disorder is a neurodegenerative disorder, a symptom of a rare genetic disorder, a mental health disorder, a metabolic syndrome, osteoporosis, cardiac failure, coma, or a complication in emergence from anesthesia.

In some embodiments, the neurodegenerative disorder is narcolepsy, cataplexy, excessive daytime sleepiness, Parkinson's disease, Alzheimer's disease, Huntington's disease, multiple sclerosis, traumatic brain injury, idiopathic hypersomnia, sleep apnea, insomnia, age-related cognitive dysfunction, or a disorder of recurrent hypersomnia.

In some embodiments, the neurodegenerative disorder is narcolepsy. In some embodiments, the narcolepsy is narcolepsy type 1. In some embodiments, the narcolepsy is narcolepsy type 2.

In some embodiments, the neurodegenerative disorder is a symptom of narcolepsy.

In some embodiments, a symptom of narcolepsy is excessive daytime sleepiness, disturbed nighttime sleep, or inappropriately timed rapid-eye-movement (REM) sleep.

In some embodiments, the neurodegenerative disorder is cataplexy. In some embodiments, cataplexy is pathognomonic of narcolepsy (e.g., narcolepsy type 1)

In some embodiments, the neurodegenerative disorder is excessive daytime sleepiness.

In some embodiments, the neurodegenerative disorder is Parkinson's disease.

In some embodiments, the neurodegenerative disorder is Alzheimer's disease.

In some embodiments, the neurodegenerative disorder is Huntington's disease.

In some embodiments, the neurodegenerative disorder is multiple sclerosis.

In some embodiments, the neurodegenerative disorder is a traumatic brain injury.

In some embodiments, the neurodegenerative disorder is idiopathic hypersomnia.

In some embodiments, the neurodegenerative disorder is sleep apnea.

In some embodiments, the neurodegenerative disorder is insomnia.

In some embodiments, the neurodegenerative disorder is age-related cognitive dysfunction.

In some embodiments, the neurodegenerative disorder is a disorder of recurrent hypersomnia.

In some embodiments, a disorder of recurrent hypersomnia is Klein-Levin syndrome, inappropriately timed sleep, (e.g., delayed- or advanced-sleep phase disorder), shift work disorder, or jet lag disorder.

In some embodiments, the disease or disorder is a symptom of a rare genetic disorder.

In some embodiments, a symptom of a rare genetic disorder is abnormal daytime sleepiness.

In some embodiments, a symptom of a rare genetic disorder is sleep onset REM periods.

In some embodiments, a symptom of a rare genetic disorder is cataplexy-like symptoms.

In some embodiments, a rare genetic disorder is ADCA-DN, Coffin-Lowry syndrome, Moebius syndrome, Norrie disease, Niemann-Pick disease type C, or Prader-Willi syndrome.

In some embodiments, the disease or disorder is a mental health disorder.

In some embodiments, the mental health disorder is attention deficit hyperactivity disorder.

In some embodiments, the mental health disorder is attention deficit disorder.

In some embodiments, the disease or disorder is a metabolic syndrome.

In some embodiments, the metabolic syndrome is obesity.

In some embodiments, the disease or disorder is osteoporosis.

In some embodiments, the disease or disorder is cardiac failure.

In some embodiments, the disease or disorder is a coma.

In some embodiments, the disease or disorder is a complication in emergence from anesthesia.

In some embodiments, the disease or disorder is a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia.

In some embodiments, the disease or disorder is narcolepsy, idiopathic hypersomnia, sleep apnea, or insomnia.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardisation of in vitro and in vivo test systems for the evaluation of the effects of modulators of orexin-2 receptor activity in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of molecules of the present disclosure described herein also apply.

The compounds of the disclosure or pharmaceutical compositions comprising these compounds may be administered to a subject by any convenient route of administration, whether systemically, peripherally, or topically (i.e., at the site of desired action).

Routes of administration include, but are not limited to, oral (e.g. by ingestion); buccal; sublingual; transdermal (including, e.g., by a patch, plaster, etc.); transmucosal (including, e.g, by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Exemplary Embodiments

Exemplary Embodiment 1. A compound of Formula (I):

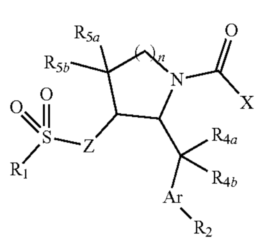

(I)

or a pharmaceutically acceptable salt thereof, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is oxo, halogen, —CN, —OH, —O($C_1$-$C_6$ alkyl), —$NH_2$, —NH($C_1$-$C_6$ alkyl), or —N($C_1$-$C_6$ alkyl)$_2$;

Z is —O— or —$NR_Z$—;

$R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —O($C_1$-$C_6$ alkyl), —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_3$-$C_7$ cycloalkyl, or 3- to 7-membered heterocycloalkyl;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_2$ is $C_2$-$C_6$ alkynyl optionally substituted with one or more $R_{2S}$;

each $R_{2S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$;

each $R_{2SS}$ independently is oxo, halogen, —CN, —OH, —$NH_2$, $C_1$-$C_6$ alkyl, $C_2$-$C_6$ alkenyl, or $C_2$-$C_6$ alkynyl, or $C_1$-$C_6$ haloalkyl;

$R_{4a}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{4b}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{5a}$ and $R_{5b}$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_{5S}$; or $R_{5a}$ and $R_{5a}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$;

each $R_{5S}$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl; and n is 0, 1, 2, or 3.

Exemplary Embodiment 2. The compound of Exemplary Embodiment 1, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is halogen, —OH, or —O($C_1$-$C_6$ alkyl);

Z is —NH—;

$R_1$ is —NH($C_1$-$C_6$ alkyl), —N($C_1$-$C_6$ alkyl)$_2$, $C_1$-$C_6$ alkyl, or 3- to 7-membered heterocycloalkyl, wherein the —NH($C_1$-$C_6$ alkyl), —N($C_1$-$C_6$ alkyl)$_2$, $C_1$-$C_6$ alkyl, or 3- to 7-membered heterocycloalkyl is optionally substituted with one or more $R_{1S}$;

each $R_{1S}$ independently is halogen;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen or —O($C_1$-$C_6$ alkyl);

$R_2$ is $C_2$-$C_6$ alkynyl optionally substituted with one or more $R_{2S}$;

each $R_{2S}$ independently is —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl, wherein the —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl is optionally substituted with one or more $R_{2SS}$;

each $R_{2SS}$ independently is halogen, $C_1$-$C_6$ alkyl, or $C_1$-$C_6$ haloalkyl;

$R_{4a}$ is H;

$R_{4b}$ is H;

$R_{5a}$ and $R_{5b}$ each independently are H or halogen; or $R_{5a}$ and $R_{5a}$, together with the atom they attach to, form $C_3$-$C_7$ cycloalkyl; and n is 1 or 2.

Exemplary Embodiment 3. The compound of any one of the preceding Exemplary Embodiments, wherein X is —O($C_1$-$C_6$ alkyl) optionally substituted with one or more $R_{X1}$.

Exemplary Embodiment 4. The compound of any one of the preceding Exemplary Embodiments, wherein X is —NH ($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is optionally substituted with one or more $R_{X1}$.

Exemplary Embodiment 5. The compound of any one of the preceding Exemplary Embodiments, wherein X is $C_1$-$C_6$ alkyl optionally substituted with one or more $R_{X1}$.

Exemplary Embodiment 6. The compound of any one of the preceding Exemplary Embodiments, wherein X is $C_3$-$C_7$ cycloalkyl optionally substituted with one or more $R_{X1}$.

Exemplary Embodiment 7. The compound of any one of the preceding Exemplary Embodiments, wherein X is 3- to 7-membered heterocycloalkyl optionally substituted with one or more $R_{X1}$.

Exemplary Embodiment 8. The compound of any one of the preceding Exemplary Embodiments, wherein X is oxetanyl or azetidinyl, wherein the oxetanyl or azetidinyl is optionally substituted with one or more $R_{X1}$.

Exemplary Embodiment 9. The compound of any one of the preceding Exemplary Embodiments, wherein at least one $R_{X1}$ is oxo, halogen, —CN, —OH, —O($C_1$-$C_6$ alkyl), —$NH_2$, —NH($C_1$-$C_6$ alkyl), or —N($C_1$-$C_6$ alkyl)$_2$.

Exemplary Embodiment 10. The compound of any one of the preceding Exemplary Embodiments, wherein Z is —$NR_Z$—.

Exemplary Embodiment 11. The compound of any one of the preceding Exemplary Embodiments, wherein Z is —NH—.

Exemplary Embodiment 12. The compound of any one of the preceding Exemplary Embodiments, wherein $R_1$ is —NH($C_1$-$C_6$ alkyl), —N($C_1$-$C_6$ alkyl)$_2$, $C_1$-$C_6$ alkyl, or 3- to 7-membered heterocycloalkyl, wherein the —NH($C_1$-$C_6$ alkyl), —N($C_1$-$C_6$ alkyl)$_2$, $C_1$-$C_6$ alkyl, or 3- to 7-membered heterocycloalkyl is optionally substituted with one or more $R_{1S}$ Exemplary Embodiment 13. The compound of any one of the preceding Exemplary Embodiments, wherein $R_1$ is —$NH_2$, —NH($C_1$-$C_6$ alkyl), or —N($C_1$-$C_6$ alkyl)$_2$, wherein the —NH($C_1$-$C_6$ alkyl) or —N($C_1$-$C_6$ alkyl)$_2$ is optionally substituted with one or more $R_{1S}$.

Exemplary Embodiment 14. The compound of any one of the preceding Exemplary Embodiments, wherein $R_1$ is —$NH_2$.

Exemplary Embodiment 15. The compound of any one of the preceding Exemplary Embodiments, wherein $R_1$ is $C_1$-$C_6$ alkyl optionally substituted with one or more $R_{1S}$.

Exemplary Embodiment 16. The compound of any one of the preceding Exemplary Embodiments, wherein $R_1$ is $C_1$-$C_6$ alkyl.

Exemplary Embodiment 17. The compound of any one of the preceding Exemplary Embodiments, wherein $R_1$ is $CH_3$.

Exemplary Embodiment 18. The compound of any one of the preceding Exemplary Embodiments, wherein $R_1$ is $CH_2CH_3$.

Exemplary Embodiment 19. The compound of any one of the preceding Exemplary Embodiments, wherein Ar is $C_6$-$C_{10}$ aryl optionally substituted with one or more $R_A$.

Exemplary Embodiment 20. The compound of any one of the preceding Exemplary Embodiments, wherein Ar is phenyl optionally substituted with one or more $R_A$.

Exemplary Embodiment 21. The compound of any one of the preceding Exemplary Embodiments, wherein Ar is 5- to 10-membered heteroaryl optionally substituted with one or more $R_A$.

Exemplary Embodiment 22. The compound of any one of the preceding Exemplary Embodiments, wherein Ar is pyridinyl optionally substituted with one or more $R_A$.

Exemplary Embodiment 23. The compound of any one of the preceding Exemplary Embodiments, wherein at least one $R_A$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

Exemplary Embodiment 24. The compound of any one of the preceding Exemplary Embodiments, wherein at least one $R_A$ is halogen.

Exemplary Embodiment 25. The compound of any one of the preceding Exemplary Embodiments, wherein at least one $R_A$ is F or Cl.

Exemplary Embodiment 26. The compound of any one of the preceding Exemplary Embodiments, wherein $R_2$ is ethynyl optionally substituted with one or more $R_{2S}$.

Exemplary Embodiment 27. The compound of any one of the preceding Exemplary Embodiments, wherein at least one $R_{2S}$ is —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl, wherein the —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl is optionally substituted with one or more $R_{2SS}$.

Exemplary Embodiment 28. The compound of any one of the preceding Exemplary Embodiments, wherein at least one $R_{2S}$ is oxo, halogen, or —CN.

Exemplary Embodiment 29. The compound of any one of the preceding Exemplary Embodiments, wherein at least one $R_{2S}$ is —OH or —O($C_1$-$C_6$ alkyl) optionally substituted with one or more $R_{2SS}$.

Exemplary Embodiment 30. The compound of any one of the preceding Exemplary Embodiments, wherein at least one $R_{2S}$ is —$NH_2$, —NH($C_1$-$C_6$ alkyl), or —N($C_1$-$C_6$ alkyl)$_2$, wherein the —NH($C_1$-$C_6$ alkyl) or —N($C_1$-$C_6$ alkyl)$_2$ is optionally substituted with one or more $R_{2SS}$.

Exemplary Embodiment 31. The compound of any one of the preceding Exemplary Embodiments, wherein at least one $R_{2S}$ is —S($C_1$-$C_6$ alkyl) or —$SO_2$($C_1$-$C_6$ alkyl), wherein the —S($C_1$-$C_6$ alkyl) or —$SO_2$($C_1$-$C_6$ alkyl) is optionally substituted with one or more $R_{2SS}$.

Exemplary Embodiment 32. The compound of any one of the preceding Exemplary Embodiments, wherein at least one $R_{2S}$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more $R_{2SS}$.

Exemplary Embodiment 33. The compound of any one of the preceding Exemplary Embodiments, wherein at least one $R_{2S}$ is $C_6$-$C_{10}$ aryl, 5- to 10-membered heteroaryl, $C_3$-$C_7$ cycloalkyl, or 3- to 7-membered heterocycloalkyl, wherein the $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$.

Exemplary Embodiment 34. The compound of any one of the preceding Exemplary Embodiments, wherein at least one $R_{2S}$ is $C_3$-$C_7$ cycloalkyl optionally substituted with one or more $R_{2SS}$.

Exemplary Embodiment 35. The compound of any one of the preceding Exemplary Embodiments, wherein at least one $R_{2S}$ is 3- to 7-membered heterocycloalkyl optionally substituted with one or more $R_{2SS}$.

Exemplary Embodiment 36. The compound of any one of the preceding Exemplary Embodiments, wherein at least one each $R_{2SS}$ is halogen, $C_1$-$C_6$ alkyl, or $C_1$-$C_6$ haloalkyl.

Exemplary Embodiment 37. The compound of any one of the preceding Exemplary Embodiments, wherein at least one each $R_{2SS}$ is oxo, halogen, —CN, —OH, or —$NH_2$.

Exemplary Embodiment 38. The compound of any one of the preceding Exemplary Embodiments, wherein at least one each $R_{2SS}$ is $C_1$-$C_6$ alkyl, $C_2$-$C_6$ alkenyl, or $C_2$-$C_6$ alkynyl, or $C_1$-$C_6$ haloalkyl.

Exemplary Embodiment 39. The compound of any one of the preceding Exemplary Embodiments, wherein $R_{4a}$ is H.

Exemplary Embodiment 40. The compound of any one of the preceding Exemplary Embodiments, wherein $R_{4a}$ is halogen, —CN, —OH, —O($C_1$-$C_6$ alkyl), —$NH_2$, —NH ($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

Exemplary Embodiment 41. The compound of any one of the preceding Exemplary Embodiments, wherein $R_{4b}$ is H.

Exemplary Embodiment 42. The compound of any one of the preceding Exemplary Embodiments, wherein $R_{4b}$ is halogen, —CN, —OH, —O($C_1$-$C_6$ alkyl), —$NH_2$, —NH ($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

Exemplary Embodiment 43. The compound of any one of the preceding Exemplary Embodiments, wherein both $R_{4a}$ and $R_{4b}$ are H.

Exemplary Embodiment 44. The compound of any one of the preceding Exemplary Embodiments, wherein $R_{5a}$ and $R_{5b}$ each independently are H or halogen; or $R_{5a}$ and $R_{5a}$, together with the atom they attach to, form $C_3$-$C_7$ cycloalkyl optionally substituted with one or more $R_{5S}$.

Exemplary Embodiment 45. The compound of any one of the preceding Exemplary Embodiments, wherein $R_{5a}$ and $R_{5b}$ each independently are H or halogen.

Exemplary Embodiment 46. The compound of any one of the preceding Exemplary Embodiments, wherein $R_{5a}$ and $R_{5b}$ each are H.

Exemplary Embodiment 47. The compound of any one of the preceding Exemplary Embodiments, wherein $R_{5a}$ and $R_{5b}$ each independently are halogen.

Exemplary Embodiment 48. The compound of any one of the preceding Exemplary Embodiments, wherein $R_{5a}$ and $R_{5a}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$.

Exemplary Embodiment 49. The compound of any one of the preceding Exemplary Embodiments, wherein n is 1 or 2.

Exemplary Embodiment 50. The compound of any one of the preceding Exemplary Embodiments, wherein n is 1.

Exemplary Embodiment 51. The compound of any one of the preceding Exemplary Embodiments, being of Formula (II):

(II)

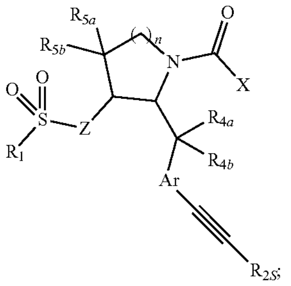

a pharmaceutically acceptable salt thereof.

Exemplary Embodiment 52. The compound of any one of the preceding Exemplary Embodiments, being of Formula (III-a) or (III-b):

(III-a)

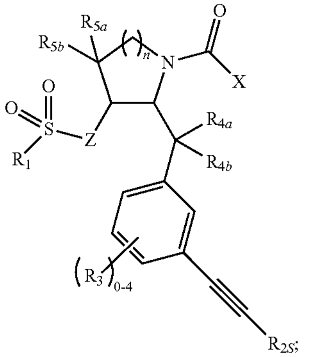

(III-b)

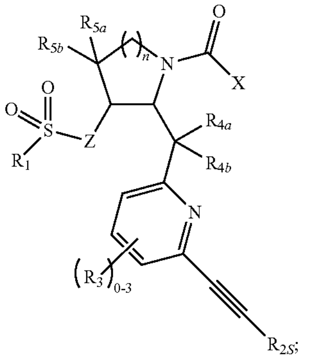

or a pharmaceutically acceptable salt thereof.

Exemplary Embodiment 53. The compound of any one of the preceding Exemplary Embodiments, being of Formula (IV-a) or (IV-b):

(IV-a)

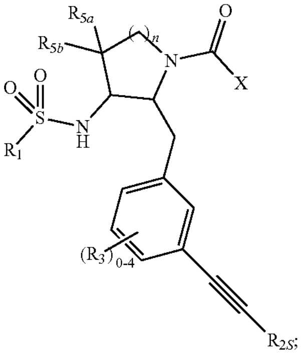

(IV-b)

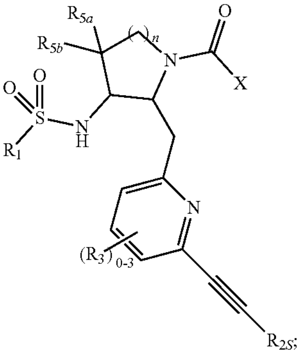

or a pharmaceutically acceptable salt thereof.

Exemplary Embodiment 54. The compound of any one of the preceding Exemplary Embodiments, wherein the compound is selected from the compounds described in Table 1 and pharmaceutically acceptable salts thereof.

Exemplary Embodiment 55. The compound of any one of the preceding Exemplary Embodiments, wherein the compound is selected from the compounds described in Table 2 and pharmaceutically acceptable salts thereof.

Exemplary Embodiment 56. A compound obtainable by, or obtained by, a method described herein;

optionally, the method comprises one or more steps described in Scheme 1.

Exemplary Embodiment 57. A pharmaceutical composition comprising the compound of any one of the preceding Exemplary Embodiments or a pharmaceutically acceptable salt thereof, and a pharmaceutically acceptable diluent or carrier.

Exemplary Embodiment 58. The pharmaceutical composition of any one of the preceding Exemplary Embodiments, wherein the compound is selected from the compounds described in Tables 1 and 2.

Exemplary Embodiment 59. A method of modulating orexin-2 receptor activity, comprising contacting a cell with an effective amount of the compound of anyone of the preceding Exemplary Embodiments; optionally the activity is in vitro or in vivo.

Exemplary Embodiment 60. A method of treating or preventing a disease or disorder in a subject in need thereof, comprising administering to the subject a therapeutically effective amount of the compound or pharmaceutical composition of any one of the preceding Exemplary Embodiments.

Exemplary Embodiment 61. The compound or pharmaceutical composition of any one of the preceding Exemplary Embodiments for use in modulating orexin-2 receptor activity; optionally, the activity is in vitro or in vivo.

Exemplary Embodiment 62. The compound or pharmaceutical composition of any one of the preceding Exemplary Embodiments for use in treating or preventing a disease or disorder.

Exemplary Embodiment 63. Use of the compound of any one of the preceding Exemplary Embodiments in the manufacture of a medicament for modulating orexin-2 receptor activity; optionally, the activity is in vitro or in vivo.

Exemplary Embodiment 64. Use of the compound of any one of the preceding Exemplary Embodiments in the manufacture of a medicament for treating or preventing a disease or disorder.

Exemplary Embodiment 65. The method, compound, pharmaceutical composition, or use of any one of the preceding Exemplary Embodiments, wherein the disease or disorder is associated with an implicated orexin-2 receptor.

Exemplary Embodiment 66. The method, compound, pharmaceutical composition, or use of any one of the preceding Exemplary Embodiments, wherein the disease or disorder is a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia.

Exemplary Embodiment 67. The method, compound, pharmaceutical composition, or use of any one of the preceding Exemplary Embodiments, wherein the disease or disorder is narcolepsy, idiopathic hypersomnia, sleep apnea, or insomnia.

EXAMPLES

Abbreviations

ACN Acetonitrile
AIBN Azobisisobutyronitrile
BOC tert-butyl carbamate
BOP (benzotriazol-1-yloxy)tris(dimethylamino)phosphonium hexafluorophosphate
BTC bis(trichloromethyl) carbonate
CDI carbonyl diimidazole
DAD diode array detector
DCM Dichloromethane
DIEA/DIPEA N,N-diisopropylethylamine
DMF N,N-dimethylformamide
DMSO Dimethylsulfoxide
EA ethyl acetate
EDCI 1-ethyl-3-(3-dimethylaminopropyl) carbodiimide
ELSD evaporative light scattering detector
ES/ESI electrospray ionisation
HATU 1-[Bis(dimethylamino)methylene]-1H-1,2,3-triazolo[4,5-b]pyridinium 3-oxid hexafluorophosphate
HOAT 1-hydroxy-7-azabenzotriazole
HOBT hydroxy benzotriazole
HPLC high-performance liquid chromatography
IPA Isopropylalcohol
LC liquid chromatography
LiHMDS lithium hexamethyl disilazide
MS mass spectrometry
NMR nuclear magnetic resonance
Py Pyridine
RT retention time
SFC supercritical fluid chromatography
TBAI tetrabutyl ammonium iodide
TEA Triethylamine
TFA trifluoroacetic acid
TFAA trifluoroacetic anhydride
THF Tetrahydrofuran
TLC thin layer chromatography
TMS tetramethyl silane
UV Ultraviolet NMR Conditions NMR spectra were recorded on Bruker Avance III HD Ultra Shield 400 MHz with a 5 mm PABBO probe, Bruker AVANCE NEO 400 MHz equipped with a 5 mm Iprobe, Bruker AVANCE III HD 400 MHz with a 5 mm BBO proble, Varian 400 MR equipped with a 5 mm 4NUC PFG. The samples were recorded at 25° C. using DMSO-$d_6$, MeOH-$d_4$ or MeCN-$d_3$ as a solvent.

LCMS Conditions

Condition A: LC/MS Agilent Technologies 1260 Infinity LC with Chemstation software, Aqueous (A2): Water (2.5 L) with 2.5 mL of 28% Ammonia in water solution Organic (B2): Acetonitrile (2.5 L) with 125 mL Water and 2.5 mL of 28% Ammonia in water solution, System runs at a flow rate of 1.5 mL/min, Injection volume of 0.5 μL, Phenomenex Gemini-NX, 5 μm, C18, 30×2 mm. Column oven temp of 40° C. Diode Array Detector with UV detection from 190 to 400 nm and Agilent Mass Spectrometer 6120 Single Quadrupole with API-ES source. Gradients written in the following format: [Time (min)/% A2: % B2], Short Run: [0.00/95:5], [2.0/5:95], [2.5/5:95], [2.6/95:5], [3.0/95:5].

Condition B: LC/MS Agilent Technologies 1260 Infinity LC with Chemstation software, Aqueous (A2): Water (2.5 L) with 2.5 mL of 28% Ammonia in water solution Organic (B2): Acetonitrile (2.5 L) with 125 mL Water and 2.5 mL of 28% Ammonia in water solution, System runs at a flow rate of 1.5 mL/min, Injection volume of 0.5 μL, Phenomenex Gemini-NX, 5 m, C18, 30×2 mm. Column oven temp of 40° C. Diode Array Detector with UV detection from 190 to 400 nm and Agilent Mass Spectrometer 6120 Single Quadrupole with API-ES source. Gradients written in the following format: [Time (min)/% A2: % B2], Long Run: [0.00/98:2], [0.1/98:2], [8.4/5:95], [10.0/5:95], [10.1/98:2], [12.0/98:2].

Condition C: Hewlett Packard 1100 series with Masslynx software, Aqueous (C): Water (2.5 L) with 2.5 mL of 28% Ammonia in water solution Organic (D): Acetonitrile (2.5 L) with 125 mL Water and 2.5 mL of 28% Ammonia in water solution, System runs at a flow rate of 1.5 mL/min, Injection volume of 1 μL, Phenomenex Gemini-NX, 5 m, C18, 30×2 mm. Column oven temp of 45° C. Hewlett Packard G1315A Diode Array Detector with UV detection from 230 to 400 nm and Waters micromass ZQ mass spectrometer. Gradients written in the following format: [Time (min)/% C: % D], Short Run: [0.00/98:2], [0.1/98:2], [2.5/5:95], [3.5/5:95].

Condition D: Hewlett Packard 1100 series with Masslynx software, Aqueous (C): Water (2.5 L) with 2.5 mL of 28% Ammonia in water solution Organic (D): Acetonitrile (2.5 L) with 125 mL Water and 2.5 mL of 28% Ammonia in water solution, System runs at a flow rate of 1.5 mL/min, Injection volume of 1 μL, Phenomenex Gemini-NX, 5 m, C18, 30×2 mm. Column oven temp of 45° C. Hewlett Packard G1315A Diode Array Detector with UV detection from 230 to 400 nm and Waters micromass ZQ mass spectrometer. Gradients written in the following format: [Time (min)/% C: % D], Long Run: [0.00/98:2], [0.1/98:2], [8.4/5:95], [10.0/5:95].

Condition E:

| LC Parameter | |
|---|---|
| Instrument: | AQUITY with PDA detector and QDA Performance |
| Column | C18, 50*2.1 mm, 1.6 μm |
| Mobile Phase | (A) 0.1% Formic acid inMilli Q water (pH = 2.70)<br>(B) 0.1% Formic acid in water:Acetonitrile (10:90) |
| Column Temperature | 35° C. |
| Auto sampler Temperature | 5° C. |
| Run Time: | 4 min |

Gradient:

| TIME (Minute) | (%)A | (%)B | Flow (mL/min) |
|---|---|---|---|
| 0.00 | 97 | 03 | 0.8 |
| 0.20 | 97 | 03 | 0.8 |
| 2.70 | 02 | 98 | 0.8 |
| 3.00 | 00 | 100 | 1.0 |
| 3.50 | 00 | 100 | 1.0 |
| 3.51 | 97 | 03 | 0.8 |
| 4.00 | 97 | 03 | 0.8 |

Mass Parameter

Probe ESI capillary

Source Temperature: 120° C.

Probe Temperature: 600° C.

Capillary Voltage: 0.8 KV (+Ve and −Ve)

Cone Voltage: 10 & 30 V

Mode of Ionization: +Ve and −Ve

Condition F: LC/MS (The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.037% trifluoroacetic acid in water, mobile phase B was 0.018% trifluoroacetic acid in acetonitrile. The column used for chromatography was a Kinetex C18 50×2.1 mm column (5 μm particles). Detection methods are diode array (DAD) and evaporative light scattering (ELSD) detection as well as positive electrospray ionization. MS range was 100-1000.

Condition G: LC/MS (The column used for chromatography was a Chormolith Flash RP-18e 25-2 mm. Detection methods are diode array (DAD). MS mode was positive electrospray ionization. MS range was 100-1000. Mobile phase A was 0.04% $CF_3CO_2H$ in water, and mobile phase B was 0.02% $CF_3CO_2H$ in HPLC grade acetonitrile. The gradient was 5-95% B in 1.50 min 0.5% B in 0.01 min, 5-95% B (0.01-0.70 min) with a hold at 95% B for 0.45 min, 95-5% B (1.15-1.16 min) with a hold at 5% B for 0.34 min. The flow rate was 1.5 mL/min.

Condition H: LC/MS (The column used for chromatography was a Kinetex 5 μm EVO C18 100A. Detection methods are diode array (DAD). MS mode was positive electrospray ionization. MS range was 100-1000. Mobile phase A was 0.04% $CF_3CO_2H$ in water, and mobile phase B was 0.02% $CF_3CO_2H$ in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min with a hold at 5% B for 0.39 min. The flow rate was 1.0 mL/min(0.01-1.80) 1.2 mL (1.81-2.20).

Condition I: LC/MS (The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was $H_2O$+10 mM $NH_4HCO_3$, mobile phase B was ACN. The column used for chromatography was a Xbridge Shield RP18 2.1*50 mm column (5 μm particles). Detection methods are diode array (DAD) and evaporative light scattering (ELSD) detection as well as positive electrospray ionization. MS range was 100-1000.

Synthesis of Intermediate 1

Step 1: tert-butyl 2-(3-bromobenzyl)-3-oxopyrrolidine-1-carboxylate

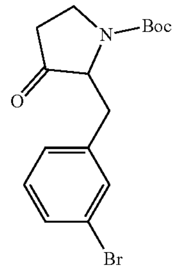 [SMILES: CC(C)(C)OC(=O)N1CCC(=O)C1Cc1cccc(Br)c1]

2-methyl-2-((3-oxopyrrolidine-1-carbonyl)oxy)propan-1-ylium (50.00 g, 270 mmol) was dissolved in toluene (500 mL) at room temperature. Pyrrolidine (33.25 mL, 405 mmol) was added at room temperature and reaction mixture stirred at 120° C. for 5 h using Dean-Stark apparatus. Reaction mixture was concentrated in vacuo to afford a red sticky residue. This residue was re-dissolved in acetonitrile (500 mL) and 1-bromo-3-(bromomethyl)benzene (66.9 g, 270 mmol) and tetrabutylammonium iodide (19.94 g, 54 mmol) were added at room temperature and reaction mixture was subsequently heated and allowed to stir at 80° C. for 2 h. The reaction mixture was diluted with water (1 L) and extracted with dichloromethane (4×250 mL). The organic layers were combined and dried ($Na_2SO_4$). Solvent was removed in vacuo to afford crude compound which was purified by normal phase gradient column chromatography (Normal phase, Silica), product eluted at 0% to 2% EtOAc in Hexane to afford the title compound (24.00 g, 26% yield) as a yellow gum. LCMS (method E) m/z 298 (ES+, M-56) at 2.43 min.

Step 2: tert-butyl 3-amino-2-(3-bromobenzyl)pyrrolidine-1-carboxylate_cis Racemic (Intermediate 1)

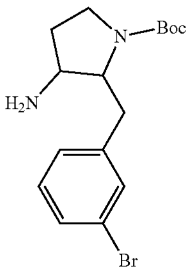

Tert-butyl 2-(3-bromobenzyl)-3-oxopyrrolidine-1-carboxylate (20.00 g, 56.67 mmol) was dissolved in methanol (100 mL). Ammonium formate (28.58 g, 453 mmol) and chloro[N-[4(dimethylamino)phenyl]-2-pyridinecarboxamidato](pentamethylcyclopentadienyl) iridium(III) (0.68 g, 1.13 mmol) were added at room temperature. The reaction mixture was subsequently heated and stirred at 80° C. for 2 h. The reaction mixture was diluted with water (500 mL) and extracted with EtOAc (250 mL). The aqueous layer was further extracted with EtOAc (3×150 mL). The organic layers were combined and dried ($Na_2SO_4$) and the solvent was removed in vacuo. Crude product was purified by reverse phase gradient flash column chromatography (reverse phase, C18 silica), product eluted at 0% to 30% acetonitrile in water with 0.10% formic acid and 5 mmol ammonium acetate as a modifier to afford a yellow solid. The solid was dissolved in saturated aqueous $NaHCO_3$ solution (500 mL) and extracted with dichloromethane (3×250 mL). The organic layers were combined and dried ($Na_2SO_4$). Solvent was evaporated in vacuo to afford the title compound (6.50 g, 26% yield) as an orange gum. LCMS (method E) m/z 299 (ES+, M-$^{t}$Bu) at 1.38 min.

Synthesis of Intermediate 3 tert-butyl 2-(3-bromobenzyl)-3-(ethylsulfonamido) pyrrolidine-1-carboxylate_cis Racemic (Intermediate 3)

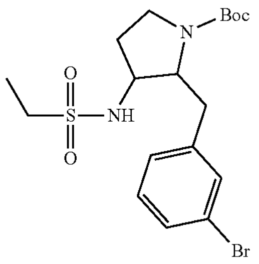 [SMILES: CCS(=O)(=O)NC1CCN(C(=O)OC(C)(C)C)C1Cc1cccc(Br)c1]

To a cooled (<5° C.) solution of tert-butyl 3-amino-2-(3-bromobenzyl)pyrrolidine-1-carboxylate_cis racemic (5.7 g, 16 mmol) and $Et_3N$ (4.52 mL, 32 mmol) in dichloromethane (80 mL) was added ethanesulfonyl chloride (2.09 mL, 24.07 mmol) and the reaction stirred at RT for 1 h. The crude reaction was diluted with dichloromethane (50 mL), washed with 10% citric acid (50 mL), brine (50 mL), the organic layer separated, dried over $MgSO_4$, filtered and concentrated in vacuo to afford the title compound (6.85 g, 15.3 mmol) as a light brown waxy solid. LCMS (method C) m/z 447 (ES+, M+H) at 2.22 min.

Synthesis of Intermediate 4 tert-butyl 2-(3-bromo-2-fluorobenzyl)-3-oxopyrrolidine-1-carboxylate

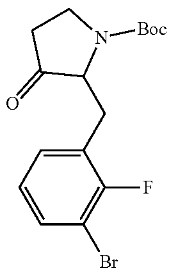 [SMILES: CC(C)(C)OC(=O)N1CCC(=O)C1Cc1cccc(Br)c1F]

Tert-butyl 3-oxopyrrolidine-1-carboxylate (100 g, 541 mmol) was dissolved in toluene (1 L) at room temperature. Pyrrolidine (111 mL, 1350 mmol) was added at room temperature and reaction mixture was allowed to stir at room temperature for 16 h. The reaction mixture was concentrated in vacuo to afford a red sticky residue. The residue was re-dissolved in acetonitrile (1 L). 1-bromo-3-(bromomethyl)-2-fluorobenzene (72 g, 270 mmol) and tetrabutylammonium iodide (40 g, 108 mmol) were added at room temperature and the reaction mixture was stirred at 70° C. for 2 h. The reaction mixture was diluted with water (1 L) and extracted with dichloromethane (4×500 mL) and the organic layers combined and dried ($Na_2SO4$). The solvent was removed in vacuo to afford crude compound which was purified by normal phase gradient column chromatography (Normal phase, Silica), product eluted at 0% to 5% EtOAc in Hexane to afford pure the title compound (96 g, 48% yield) as yellow sticky material. LCMS (method E) m/z 272 (ES+, M-100) at 2.44 min.

tert-butyl 3-amino-2-(3-bromo-2-fluorobenzyl)pyrrolidine-1-carboxylate_cis Racemic (Intermediate 4)

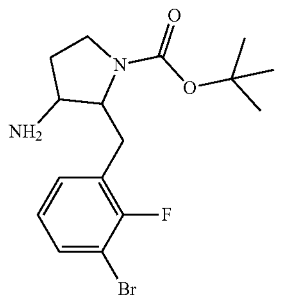 [SMILES: CC(C)(C)OC(=O)N1CCC(N)C1Cc1cccc(Br)c1F]

Tert-butyl 2-(3-bromo-2-fluorobenzyl)-3-oxopyrrolidine-1-carboxylate (40 g, 108 mmol) was dissolved in Methanol (400 mL). Ammonium formate (54.3 g, 862 mmol) and Chloro[N-[4(dimethylamino)phenyl]-2-pyridinecarboxamidato] (pentamethyl cyclopentadienyl)iridium(II) (3.25 g, 5.39 mmol) were added at room temperature. The reaction mixture was stirred at 70° C. for 2 h, diluted with water (500 mL) and extracted with dichloromethane (4×150 mL). The solvent was removed in vacuo to afford crude compound which was purified by reverse phase gradient flash column chromatography (Reverse phase, C18 silica), product eluted at 0% to 30% ACN in water with 0.1% TFA and 5 mM Ammonium acetate as a modifier to afford compound as yellow solid. The obtained solid was dissolved in saturated aqueous $NaHCO_3$ solution (100 mL) and extracted with dichloromethane (4×50 mL) and the organic layers combined and dried ($Na2SO_4$). The solvent was removed in vacuo to afford the title compound (11.8 g, 29.4% yield) as yellow sticky solid. LCMS (method E) m/z 317 (ES+, M-56) at 1.50 min.

Synthesis of Intermediate 5

Step 1: tert-butyl (2S,3S)-2-(3-bromo-2-fluorobenzyl)-3-(methylsulfonamido) pyrrolidine-1-carboxylate (Intermediate 5)

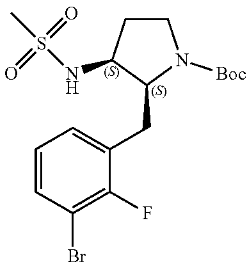

Tert-butyl 2-(3-bromo-2-fluorobenzyl)-3-oxopyrrolidine-1-carboxylate_cis racemic (intermediate 3) was resolved by SFC Prep using a Chiralpak AD-3 column and isocratic conditions of $CO_2$:(MeOH+0.05% DEA) 60:40. Isomer 1: 99% e.e. retention time=1.58 mins (tert-butyl (2S,3S)-3-amino-2-(3-bromo-2-fluorobenzyl)pyrrolidine-1-carboxylate_isomer 1). Isomer 2: 99% e.e. retention time=1.81 mins (tert-butyl (2R,3R)-3-amino-2-(3-bromo-2-fluorobenzyl) pyrrolidine-1-carboxylate_isomer 2).

To a solution of tert-butyl (2S,3S)-3-amino-2-(3-bromo-2-fluorobenzyl)pyrrolidine-1-carboxylate_isomer 1 (1.0 g, 2.68 mmol) in dichloromethane (30 mL) was added triethylamine (1.12 mL, 8.04 mmol) and MsCl (286 μL, 4.02 mmol) at 0° C. The mixture was stirred at 25° C. for 12 h, poured into saturated aqueous $NH_4Cl$ solution (15 mL) and extracted with dichloromethane (3×25 mL). The organic layer was washed with brine (5 mL), dried over $MgSO_4$ and concentrated under reduced pressure. The residue was purified by column chromatography ($SiO_2$, Petroleum ether/Ethyl acetate=3/1) to afford the title compound (700 mg 55% yield) as a white solid. $^1H$ NMR (400 MHz, chloroform-d) δ 7.43 (br t, 1H), 7.12 (br s, 1H), 6.96 (t, 1H), 4.09-3.96 (m, 1H), 3.55-3.27 (m, 2H), 2.87 (br s, 2H), 2.67-2.19 (m, 2H), 1.85-1.75 (m, 1H), 1.02-1.33 (m, 9H).

Synthesis of Intermediate 6

N-((2S,3S)-2-(3-bromo-2-fluorobenzyl)pyrrolidin-3-yl)methanesulfonamide (Intermediate 6)

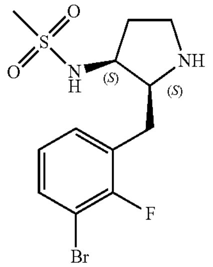

To a solution of tert-butyl (2S,3S)-2-(3-bromo-2-fluorobenzyl)-3-(methylsulfonamido)pyrrolidine-1-carboxylate (700 mg, 1.55 mmol) in dichloromethane (3 mL) was added trifluoroacetic acid (1.50 mL, 20.21 mmol) at 0° C. The mixture was stirred at 25° C. for 12 h, poured into saturated aqueous $NaHCO_3$ solution (10 mL) and extracted with dichloromethane (3×10 mL). The organic layer was washed with brine (10 mL), and dried over $MgSO_4$, concentrated under reduced pressure to afford the title compound (450 mg, 79% yield) as a yellow solid. $^1H$ NMR (400 MHz, chloroform-d) δ 7.42-7.35 (br, 1H), 7.30-7.20 (br, 1H), 7.04-6.93 (m, 1H), 3.91 (br s, 1H), 3.30-3.15 (m, 1H), 3.12-3.02 (m, 2H), 3.05-2.92 (m, 3H), 2.91-2.74 (m, 1H), 2.37-2.22 (m, 1H), 1.90-1.75 (m, 2H).

Example 1. Synthesis of Compound No. 1-22

Step 1: N-(2-(3-bromobenzyl)pyrrolidin-3-yl)ethanesulfonamide hydrochloride_cis Racemic

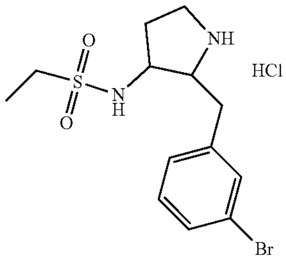 [SMILES: CCS(=O)(=O)NC1CCNC1Cc1cccc(Br)c1 ; Cl]

To a solution of tert-butyl 2-(3-bromobenzyl)-3-(ethylsulfonamido)pyrrolidine-1-carboxylate, intermediate 3 (1.4 g, 3.13 mmol) in 1,4-Dioxane (10 mL) and Methanol (5 mL) was added 4 M HCl in dioxane (7.8 mL, 31.3 mmol) and the mixture was stirred at RT for 18 h. The reaction was concentrated in vacuo to afford the title compound (990 mg, 77% yield) as an off-white solid. LCMS (method C) (ESI+): m/z 347 $(M+H)^+$, RT: 1.83 min Step 2: N-(2-(3-bromobenzyl)-1-(2-hydroxy-2-methylpropanoyl)pyrrolidin-3-yl) ethanesulfonamide_cis Racemic

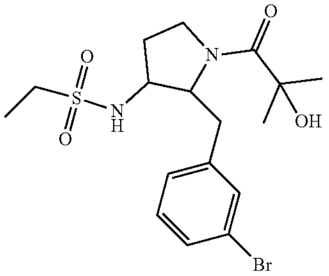 [SMILES: CCS(=O)(=O)NC1CCN(C(=O)C(C)(C)O)C1Cc1cccc(Br)c1]

To a solution of N-(2-(3-bromobenzyl)pyrrolidin-3-yl) ethanesulfonamide hydrochloride (990 mg, 2.6 mmol) in THE (31 mL) was added 2-hydroxy-2-methyl-propanoic acid (537 mg 5.2 mmol) followed by HOBt monohydrate (697 mg, 5.2 mmol), 1-(3-dimethylaminopropyl)-3-ethylcarbodiimide hydrochloride (989 mg, 5.2 mmol) and DIPEA (1.34 mL, 7.74 mmol). The reaction was stirred at RT for 18 h. The reaction mixture was extracted with EtOAc, washed with 10% citric acid, water, sat. brine, the organic layer separated, dried over $MgSO_4$, filtered and concentrated in vacuo. The residue was purified by flash column chromatography [gradient 0%-100% Ethyl acetate:MeOH (9:1)/isohexane] and the resulting gum triturated in EtOAc:isohexane (1:4) to afford the title compound (915 mg, 820% yield) as a white solid. LCMS (method C) (ESI+): m/z 433 $(M+H)^+$, RT: 1.81 min Step 3: N-(1-(2-hydroxy-2-methylpropanoyl)-2-(3-(phenylethynyl)benzyl)-pyrrolidin-3-yl)ethanesulfonamide_cis Racemic

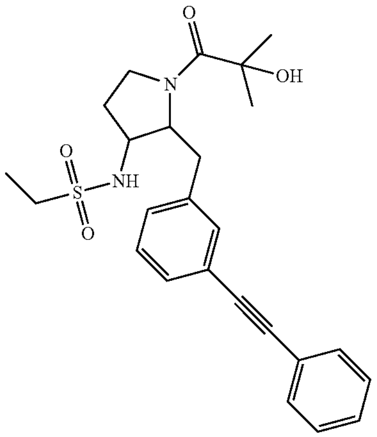 [SMILES: CCS(=O)(=O)NC1CCN(C(=O)C(C)(C)O)C1Cc1cccc(C#Cc2ccccc2)c1]

A solution of N-(2-(3-bromobenzyl)-1-(2-hydroxy-2-methylpropanoyl)pyrrolidin-3-yl)ethanesulfonamide (50 mg, 0.12 mmol), Bis(acetonitrile)dichloropalladium(II) (1.5 mg, 0.01 mmol), cesium carbonate (113 mg, 0.35 mmol), 2-Dicyclohexylphosphino-2',4',6'triisopropylbiphenyl (8.5 mg, 0.02 mmol) in MeCN (2 mL) was stirred at room temperature under an inert atmosphere for 30 min. Phenylacetylene (15 mg, 0.15 mmol) was added and the reaction mixture was heated at 90° C. for 18 h. The reaction was extracted into EtOAc, washed with water, the organic layer separated and concentrated in vacuo. The residue was purified by flash column chromatography eluting with 0-100% EtOAc/isohexane and further purified by reverse phase HPLC (Phenomenex Gemini column, 100×30 mm, 5 μm, 30 mL/min, gradient of 40% to 70% (over 8.7 min) then 100% hold (1 min), solvents: Aqueous=Water with 0.2% of 28% Ammonia solution, Organic=Acetonitrile) to afford the title compound (26 mg, 50% yield) as a white solid.

Example 2. Synthesis of Compound No. 1-21

N-(2-(3-(cyclopropylethynyl)benzyl)-1-(2-hydroxy-2-methylpropanoyl)pyrrolidin-3-yl)ethanesulfonamide_cis Racemic

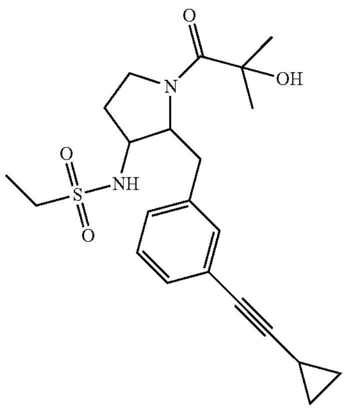 [SMILES: CCS(=O)(=O)NC1CCN(C(=O)C(C)(C)O)C1Cc1cccc(C#CC2CC2)c1]

A solution of N-(2-(3-bromobenzyl)-1-(2-hydroxy-2-methylpropanoyl)pyrrolidin-3-yl)ethanesulfonamide (100 mg, 0.23 mmol), cesium carbonate (226 mg, 0.69 mmol), 2-Dicyclohexylphosphino-2',4',6'triisopropylbiphenyl (17 mg, 0.03 mmol) in MeCN (2 mL) was stirred at room temperature under an inert atmosphere for 30 min. To this was added cyclopropylacetylene (20 mg, 0.30 mmol) and the reaction mixture was heated at 90° C. for 18 h. The reaction was extracted into EtOAc, washed with water, the organic layer separated and concentrated in vacuo. The residue was purified by flash column chromatography eluting with 0-100% EtOAc/isohexane and further purified by reverse phase HPLC (C18-HS cartridge, 12 mL/min, gradient of 10% methanol in aqueous to 100%, solvents: Aqueous=Water with 0.1% of 28% Ammonia solution, Organic=Methanol) to afford the title compound (24 mg, 25% yield) as a yellow solid.

Example 3. Synthesis of Compound No. 1-20

Step 1: tert-butyl 3-amino-2-(3-(cyclopropylethynyl)-2-fluorobenzyl)pyrrolidine-1-carboxylate_cis Racemic

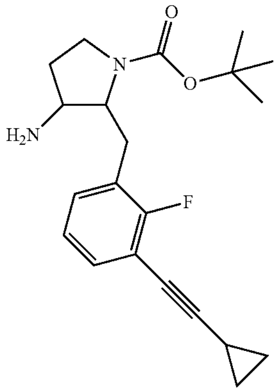 [SMILES: CC(C)(C)OC(=O)N1CCC(N)C1Cc1cccc(C#CC2CC2)c1F]

To a microwave vial was added tert-butyl 3-amino-2-(3-bromo-2-fluorobenzyl)pyrrolidine-1-carboxylate_cis racemic, intermediate 4 (500 mg, 1.34 mmol), Bis(acetonitrile) dichloropalladium(II) (17 mg, 0.07 mmol), cesium carbonate (1.31 g, 4.0 mmol), 2-Dicyclohexylphosphino-2',4',6'triisopropylbiphenyl (99 mg, 0.20 mmol), cyclopropylacetylene (119 mg, 1.74 mmol) and MeCN (9.0 mL). The reaction mixture was sealed and stirred at 90° C. for 18 h. The reaction mixture was diluted with EtOAc. Brine and 1M aq. NaOH were added, the organic and aqueous layers separated and the aqueous layer re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane, then gradient 0% to 100% MeOH in DCM] to afford the title compound (350 mg, 73% yield) as a brown oil. LCMS (method C) (ESI+): m/z 359 $(M+H)^+$, RT: 2.24 min Step 2: tert-butyl 2-(3-(cyclopropylethynyl)-2-fluorobenzyl)-3-(ethylsulfonamido)-pyrrolidine-1-carboxylate_cis Racemic

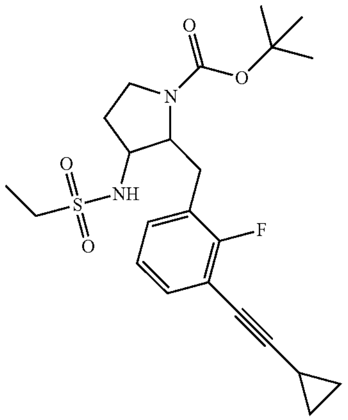 [SMILES: CCS(=O)(=O)NC1CCN(C(=O)OC(C)(C)C)C1Cc1cccc(C#CC2CC2)c1F]

To a solution of tert-butyl 3-amino-2-(3-(cyclopropylethynyl)-2-fluorobenzyl)pyrrolidine-1-carboxylate (170 mg, 0.47 mmol) and $Et_3N$ (93 uL, 0.66 mmol) in dichloromethane (10 mL) was added ethanesulfonyl chloride (73 mg, 0.57 mmol) and the reaction stirred at RT for 1.5 h. The crude reaction was extracted into EtOAc, washed with water, brine, dried over magnesium sulfate, and the organic layer was concentrated in vacuo. The residue was purified by flash column chromatography [gradient 0% to 100% Ethyl Acetate in Iso-hexane], to afford the title compound (160 mg, 75% yield) as a yellow oil. LCMS (method A) (ESI+): m/z 395 $(M-56)^+$, RT: 1.57 min Step 3: N-(2-(3-(cyclopropylethynyl)-2-fluorobenzyl)pyrrolidin-3-yl)ethanesulfonamide hydrochloride_cis_racemic

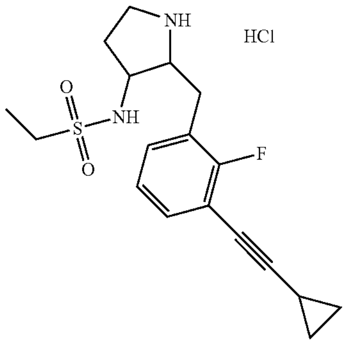 [SMILES: CCS(=O)(=O)NC1CCNC1Cc1cccc(C#CC2CC2)c1F ; Cl]

To a solution of tert-butyl 2-(3-(cyclopropylethynyl)-2-fluorobenzyl)-3-(ethylsulfonamido)pyrrolidine-1-carboxylate (160 mg, 0.36 mmol) in 1,4-Dioxane (3 mL) was added 4 M HCl in dioxane (2 mL, 8 mmol). The reaction mixture was stirred at room temperature for 2 hours and concentrated in vacuo to afford the title compound (133 mg, 970% yield) as a beige solid. LCMS (method A) (ESI+): m/z 351 $(M+H)^+$, RT: 1.30 min Step 4: N-(2-(3-(cyclopropylethynyl)-2-fluorobenzyl)-1-isobutyrylpyrrolidin-3-yl)ethanesulfonamide_cis Racemic

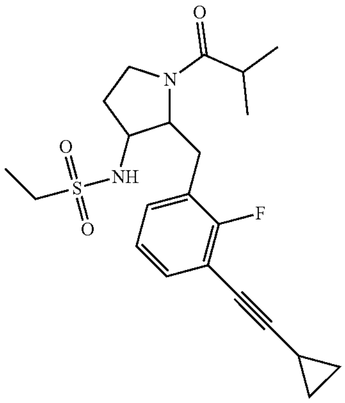 [SMILES: CCS(=O)(=O)NC1CCN(C(=O)C(C)C)C1Cc1cccc(C#CC2CC2)c1F]

To a solution of N-(2-(3-(cyclopropylethynyl)-2-fluorobenzyl)pyrrolidin-3-yl) ethanesulfonamide hydrochloride (44 mg, 0.11 mmol) and $Et_3N$ (30 μL, 0.25 mmol) in dichloromethane (3 mL) was added isobutyryl chloride (15 mg, 0.14 mmol) and the reaction stirred for 18 h. The reaction mixture was diluted with EtOAc and washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% Ethyl Acetate in Iso-hexane] and further purified by reverse phase column chromatography (C18-HS cartridge, 12 mL/min, gradient of 10% methanol in aqueous to 100%, solvents: Aqueous=Water with 0.1% of 28% Ammonia solution, Organic=Methanol) to afford the title compound (19.8 mg, 41% yield) as a white solid.

Example 4. Synthesis of Compound No. 1-19

N-(1-(cyclobutanecarbonyl)-2-(3-(cyclopropylethynyl)-2-fluorobenzyl)pyrrolidin-3-yl)ethanesulfonamide_cis Racemic

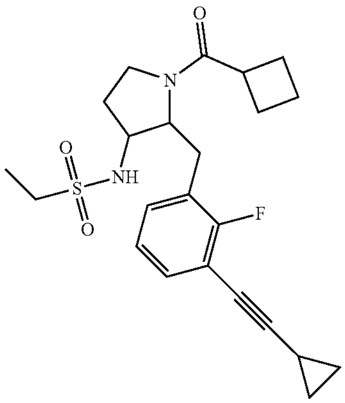 [SMILES: CCS(=O)(=O)NC1CCN(C(=O)C2CCC2)C1Cc1cccc(C#CC2CC2)c1F]

To a solution of N-(2-(3-(cyclopropylethynyl)-2-fluorobenzyl)pyrrolidin-3-yl)ethanesulfonamide hydrochloride (44 mg, 0.11 mmol) and cyclobutane carbonyl chloride (16 mg, 0.14 mmol) in dichloromethane (3 mL) was added $Et_3N$ (30 μL, 0.25 mmol) and the reaction stirred for 18 h. The reaction mixture was diluted with EtOAc and washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% EtOAc in Iso-hexane] and further purified by reverse phase column chromatography (C18-HS cartridge, 12 mL/min, gradient of 10% methanol in aqueous to 100%, solvents: Aqueous=Water with 0.1% of 28% Ammonia solution, Organic=Methanol) to afford the title compound (16 mg, 33% yield) as a white solid.

Example 5. Synthesis of Compound No. 1-18

N-(1-(azetidine-1-carbonyl)-2-(3-(cyclopropylethynyl)-2-fluorobenzyl)pyrrolidin-3-yl)ethanesulfonamide_cis Racemic

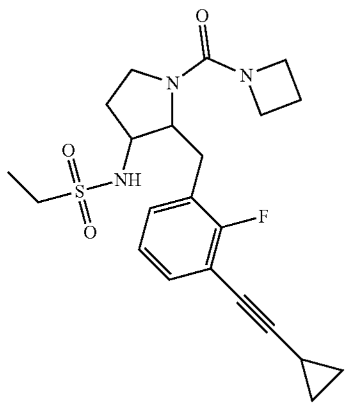 [SMILES: CCS(=O)(=O)NC1CCN(C(=O)N2CCC2)C1Cc1cccc(C#CC2CC2)c1F]

To a solution of N-(2-(3-(cyclopropylethynyl)-2-fluorobenzyl)pyrrolidin-3-yl)ethanesulfonamide hydrochloride (44 mg, 0.11 mmol) and azetidine-1-carbonyl chloride (16 mg, 0.14 mmol) in MeCN (3 mL) was added $Et_3N$ (30 μL, 0.25 mmol) and the reaction stirred for 18 h. The reaction mixture was diluted with EtOAc and washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% EtOAc in Iso-hexane] and further purified by reverse phase column chromatography (C18-HS cartridge, 12 mL/min, gradient of 10% methanol in aqueous to 100%, solvents: Aqueous=Water with 0.1% of 28% Ammonia solution, Organic=Methanol) to afford the title compound (20 mg, 41% yield) as a white solid.

Examples 6 and 7. Synthesis of Compound Nos. 1-15 and 1-16

N-(1-(azetidine-1-carbonyl)-2-(3-(cyclopropylethynyl)-2-fluorobenzyl)pyrrolidin-3-yl)ethanesulfonamide_cis racemic (Example 5) resolved on the Sepiatec SFC Prep100 system using a Lux A1 column and isocratic conditions of $CO_2$:(IPA+0.2% $NH_3$) 60:40.

Isomer 1: 99% e.e. retention time=2.09 mins. N-((2S,3S)-1-(azetidine-1-carbonyl)-2-(3-(cyclopropylethynyl)-2-fluorobenzyl)pyrrolidin-3-yl)ethanesulfonamide (Example 6)

Isomer 2: 99% e.e. retention time=2.22 mins. N-((2R,3R)-1-(azetidine-1-carbonyl)-2-(3-(cyclopropylethynyl)-2-fluorobenzyl)pyrrolidin-3-yl)ethanesulfonamide (Example 7)

Example 8. Synthesis of Compound No. 1-17

Step 1: tert-butyl 2-((6-bromopyridin-2-yl)methyl)-3-oxopyrrolidine-1-carboxylate

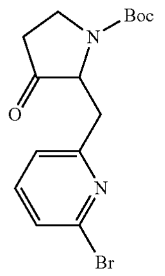 [SMILES: CC(C)(C)OC(=O)N1CCC(=O)C1Cc1cccc(Br)n1]

Tert-butyl 3-oxopyrrolidine-1-carboxylate (50 g, 270 mmol) was dissolved in Toluene (500 mL) at room temperature. Pyrrolidine (55.4 mL, 676 mmol) was added at 0° C. and the reaction mixture stirred at room temperature for 16 h. The reaction mixture was concentrated in vacuo to afford a brown sticky residue. The obtained residue was re-dissolved in Acetonitrile (500 mL). 2-bromo-6-(bromomethyl)pyridine (40.4 g, 162 mmol) and tetrabutylammonium iodide (19.9 g, 54 mmol) were added at 0° C. and reaction mixture was stirred at 80° C. for 5 h. The reaction mixture was concentrated under vacuum to afford crude compound which was purified by reverse phase gradient flash column chromatography (reverse phase, C18 silica), product was eluted at 0% to 72% ACN in water to afford crude product, which was further purified by normal phase gradient flash column chromatography (Normal phase, Silica gel), product eluted at 0% to 1% EtOAc in Hexane to afford the title compound (25 g, 26% yield) as yellow solid. LCMS (method E) m/z 299 (ES+, M-56) at 1.20 min.

Step 2: tert-butyl 2-((6-(cyclopropylethynyl)pyridin-2-yl)methyl)-3-oxopyrrolidine-1-carboxylate

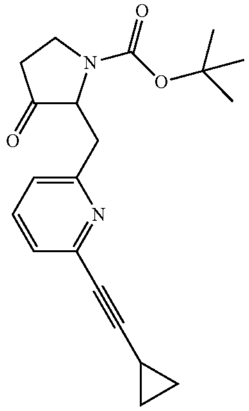 [SMILES: CC(C)(C)OC(=O)N1CCC(=O)C1Cc1cccc(C#CC2CC2)n1]

To a 20 mL microwave vial was added tert-butyl 2-((6-bromopyridin-2-yl)methyl)-3-oxopyrrolidine-1-carboxylate (500 mg, 1.41 mmol), Bis(acetonitrile)dichloropalladium(II) (18 mg, 0.07 mmol), cesium carbonate (1.38 g, 4.22 mmol), 2-Dicyclohexylphosphino-2',4',6'triisopropylbiphenyl (104 mg, 0.21 mmol), cyclopropylacetylene (125 mg, 1.83 mmol) and MeCN (9.0 mL). The reaction mixture was sealed and stirred at 90° C. for 18 h. The reaction mixture was diluted with EtOAc, washed with brine, 1M aq. NaOH, the organic and aqueous layers were separated. The aqueous layer was re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane, then gradient 0% to 100% MeOH in DCM] to afford the title compound (252 mg, 53% yield) as an orange oil. LCMS (method C) (ESI+): m/z 341 $(M+H)^+$, RT: 2.29 min Step 3: tert-butyl 3-amino-2-((6-(cyclopropylethynyl)pyridin-2-yl)methyl)-pyrrolidine-1-carboxylate_cis Racemic

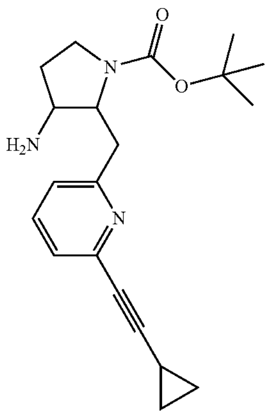 [SMILES: CC(C)(C)OC(=O)N1CCC(N)C1Cc1cccc(C#CC2CC2)n1]

A solution of tert-butyl 2-((6-(cyclopropylethynyl)pyridin-2-yl)methyl)-3-oxopyrrolidine-1-carboxylate (252 mg, 0.74 mmol) in Methanol (5.0 mL) was degassed by bubbling air through the solution for 10 min. Ammonium formate (373 mg, 5.92 mmol) and Chloro[N-[4-(dimethylamino)phenyl]-2-pyridinecarboxamidato](pentamethylcyclopentadienyl)-iridium(III) (22 mg, 0.04 mmol) were added and the reaction mixture was refluxed for 2 hours. The residue was purified by flash column chromatography [gradient 0% to 100% Ethyl Acetate in Iso-hexane, then gradient 0% to 100% MeOH in DCM] to afford the title compound (131 mg, 52%) as a brown oil. LCMS (method A) (ESI+): m/z 342 $(M+H)^+$, RT: 1.30 min Step 4: tert-butyl 2-((6-(cyclopropylethynyl)pyridin-2-yl)methyl)-3-(ethylsulfonamido)pyrrolidine-1-carboxylate_cis Racemic

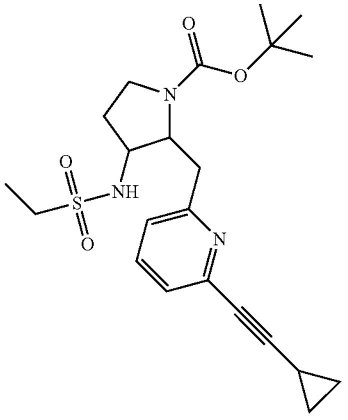 [SMILES: CCS(=O)(=O)NC1CCN(C(=O)OC(C)(C)C)C1Cc1cccc(C#CC2CC2)n1]

To a solution of tert-butyl 3-amino-2-((6-(cyclopropylethynyl)pyridin-2-yl)methyl)pyrrolidine-1-carboxylate (131 mg, 0.38 mmol) and 1,4-Diazabicyclo-[2.2.2]octane (50 µL, 0.54 mmol) in MeCN (4.0 mL) was added ethanesulfonyl chloride (59 mg, 0.46 mmol). The reaction mixture was stirred at room temperature for 18 h. The reaction mixture was diluted with EtOAc and washed with $NaHCO_3$ sat. aq. solution and brine, dried over hydrophobic frit and evaporated in vacuo. The residue was purified by flash column chromatography [gradient 0% to 100% Ethyl Acetate in Iso-hexane, then gradient 0% to 100% MeOH in dichloromethane] to afford the title compound (100 mg, 60% yield). LCMS (method A) (ESI+): m/z 434 $(M+H)^+$, RT: 1.50 min.

Step 5: N-(2-((6-(cyclopropylethynyl)pyridin-2-yl)methyl)pyrrolidin-3-yl)-ethanesulfonamide dihydrochloride_cis Racemic

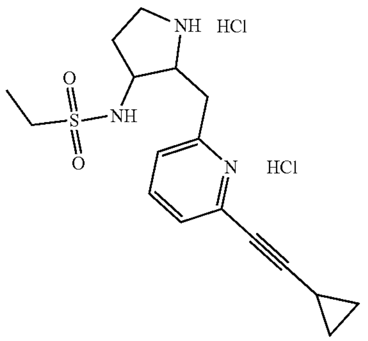 [SMILES: CCS(=O)(=O)NC1CCNC1Cc1cccc(C#CC2CC2)n1 ; Cl ; Cl]

To a flask with tert-butyl 2-((6-(cyclopropylethynyl)pyridin-2-yl)methyl)-3-(ethylsulfonamido)pyrrolidine-1-carboxylate (100 mg, 0.23 mmol) was added 4 M HCl in dioxane (3.0 mL, 12 mmol). The reaction mixture was stirred at room temperature for 2 h. The reaction mixture was evaporated in vacuo to afford the title compound (115 mg, 100%) as a brown oil. LCMS (method A) (ESI+): m/z 334 $(M+H)^+$, RT: 1.05 min.

Step 6: N-(1-(azetidine-1-carbonyl)-2-((6-(cyclopropylethynyl)pyridin-2-yl)methyl)pyrrolidin-3-yl)ethanesulfonamide_cis Racemic

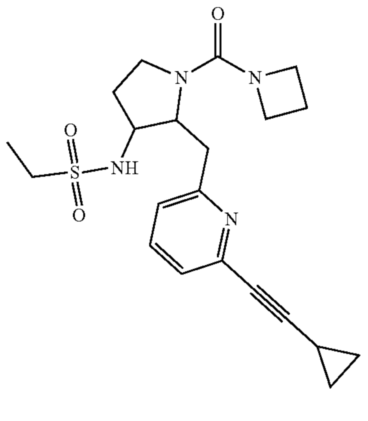 [SMILES: CCS(=O)(=O)NC1CCN(C(=O)N2CCC2)C1Cc1cccc(C#CC2CC2)n1]

To a solution of N-(2-((6-(cyclopropylethynyl)pyridin-2-yl)methyl)pyrrolidin-3-yl) ethanesulfonamide dihydrochloride (115 mg, 0.28 mmol) and $Et_3N$ (80 μL, 0.57 mmol) in dichloromethane (3.0 mL) was added Azetidine-1-carbonyl chloride (41 mg, 0.34 mmol). The reaction mixture was stirred at room temperature for 24 h, diluted with EtOAc, washed with water and brine, and evaporated in vacuo. The residue was purified by flash column chromatography [gradient 0% to 100% MeOH-Ethyl Acetate (1:9 v/v) in Iso-hexane] and further purified by reverse phase column chromatography (C18-HS cartridge, 12 mL/min, gradient of 10% methanol in aqueous to 100%, solvents: Aqueous=Water with 0.1% of 28% Ammonia solution, Organic=Methanol) to afford the title compound (5.3 mg, 4.5% yield) as an orange gum.

Example 9. Synthesis of Compound No. 1-14

Step 1: N-(2-(3-bromobenzyl)pyrrolidin-3-yl)ethanesulfonamide hydrochloride_cis Racemic

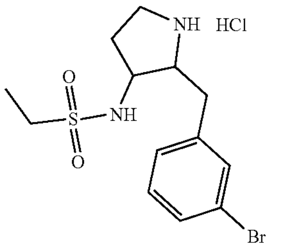 [SMILES: CCS(=O)(=O)NC1CCNC1Cc1cccc(Br)c1 ; Cl]

To a solution of tert-butyl 2-(3-bromobenzyl)-3-(ethylsulfonamido)pyrrolidine-1-carboxylate_cis racemic, intermediate 3 (1.86 g, 4.16 mmol) in Methanol (5.0 mL) was added 4 M HCl in dioxane (20 mL, 80 mmol). The reaction mixture was stirred at room temperature for 2 h and evaporated in vacuo to afford the title compound (1.56 g, 98% yield) as an off-white solid. LCMS (method A) (ESI+): m/z 347 $(M+H)^+$, RT: 1.13 min Step 2: N-(2-(3-bromobenzyl)-1-isobutyrylpyrrolidin-3-yl)ethanesulfonamide_cis Racemic

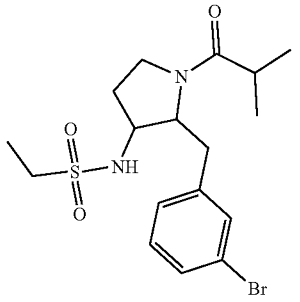 [SMILES: CCS(=O)(=O)NC1CCN(C(=O)C(C)C)C1Cc1cccc(Br)c1]

To a solution of N-(2-(3-bromobenzyl)pyrrolidin-3-yl) ethanesulfonamide hydrochloride_cis racemic (1.0 g, 2.61 mmol) and $Et_3N$ (0.73 mL, 5.21 mmol) in dichloromethane (13 mL) was added isobutyryl chloride (312 mg, 2.87 mmol). The reaction mixture was stirred at room temperature for 2 h, diluted with EtOAc, washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% Ethyl Acetate in Iso-hexane] to afford the title compound (960 mg, 88% yield) as a brown solid. LCMS (method A) (ESI+): m/z 417 $(M+H)^+$, RT: 1.22 min Step 3: N-(2-(3-(cyclopropylethynyl)benzyl)-1-isobutyrylpyrrolidin-3-yl) ethanesulfonamide_cis Racemic

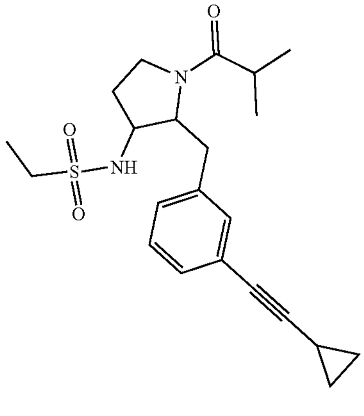 [SMILES: CCS(=O)(=O)NC1CCN(C(=O)C(C)C)C1Cc1cccc(C#CC2CC2)c1]

To a microwave vial was added N-(2-(3-bromobenzyl)-1-isobutyrylpyrrolidin-3-yl) ethanesulfonamide (75 mg, 0.18 mmol), Bis(acetonitrile)dichloropalladium(II) (2.3 mg, 0.01 mmol), cesium carbonate (176 mg, 0.54 mmol), 2-Dicyclohexylphosphino-2',4',6' triisopropylbiphenyl (13 mg, 0.03 mmol), cyclopropylacetylene (16 mg, 0.23 mmol) and MeCN (2 mL). The reaction mixture was sealed and stirred at 90° C. for 18 hours. The reaction mixture was diluted with EtOAc, washed with brine, 1M aq. NaOH, the organic and aqueous layers were separated. The aqueous layer was re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane] and further purified by reverse phase column chromatography (C18-HS cartridge 30 g, 25 mL/min, gradient of 10% methanol in aqueous to 100%, solvents: Aqueous=Water with 0.1% of 28% Ammonia solution, Organic=Methanol) to afford the title compound (25.3 mg, 35% yield) as a white solid.

Example 10. Synthesis of Compound No. 1-13

N-(2-(3-(cyclopentylethynyl)benzyl)-1-isobutyrylpyrrolidin-3-yl)ethanesulfonamide_cis Racemic

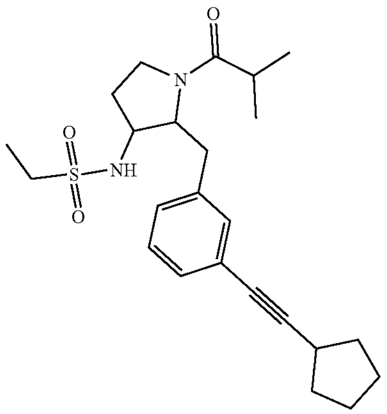 [SMILES: CCS(=O)(=O)NC1CCN(C(=O)C(C)C)C1Cc1cccc(C#CC2CCCC2)c1]

To a 20 mL microwave vial was added N-(2-(3-bromobenzyl)-1-isobutyrylpyrrolidin-3-yl)ethanesulfonamide (75 mg, 0.18 mmol), Bis(acetonitrile)dichloropalladium(II) (2.3 mg, 0.01 mmol), cesium carbonate (176 mg, 0.54 mmol), 2-Dicyclohexylphosphino-2',4',6' triisopropylbiphenyl (13 mg, 0.03 mmol), cyclopentylacetylene (22 mg, 0.23 mmol) and MeCN (2 mL). The reaction mixture was sealed and stirred at 90° C. for 18 h. The reaction mixture was diluted with EtOAc, washed with brine, 1M aq. NaOH, the organic and aqueous layers were separated. The aqueous layer was re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane] and further purified by reverse phase column chromatography (C18-HS cartridge 30 g, 25 mL/min, gradient of 10% methanol in aqueous to 100%, solvents: Aqueous=Water with 0.1% of 28% Ammonia solution, Organic=Methanol) to afford the title compound (29.7 mg, 38% yield) as a white solid.

Example 11. Synthesis of Compound No. 1-12

N-(2-(3-(3,3-dimethylbut-1-yn-1-yl)benzyl)-1-isobutyrylpyrrolidin-3-yl) ethane-sulfonamide_cis Racemic

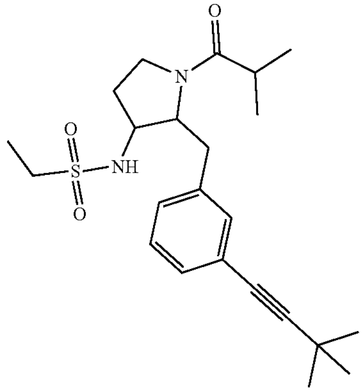 [SMILES: CCS(=O)(=O)NC1CCN(C(=O)C(C)C)C1Cc1cccc(C#CC(C)(C)C)c1]

To a 5 mL microwave vial was added N-(2-(3-bromobenzyl)-1-isobutyrylpyrrolidin-3-yl)ethanesulfonamide (75 mg, 0.18 mmol), bis(acetonitrile)dichloropalladium(II) (2.3 mg, 0.01 mmol), cesium carbonate (176 mg, 0.54 mmol), 2-dicyclohexylphosphino-2',4',6' triisopropylbiphenyl (13 mg, 0.03 mmol), tert-butylacetylene (19 mg, 0.23 mmol) and MeCN (2 mL). The reaction mixture was sealed and stirred at 90° C. for 18 h. The reaction mixture was diluted with EtOAc, filtered over hydrophobic frit and evaporated in vacuo. The residue was purified by flash column chromatography [gradient 10% to 100% Ethyl Acetate in Iso-hexane] and further purified by reverse phase column chromatography (C18-HS cartridge 30 g, 25 mL/min, gradient of 10% methanol in aqueous to 100%, solvents: Aqueous=Water with 0.1% of 28% Ammonia solution, Organic=Methanol) to afford the title compound (17.6 mg, 23% yield).

Example 12. Synthesis of Compound No. 1-11

N-(2-(2-fluoro-3-(3-methoxyprop-1-yn-1-yl)benzyl)-1-isobutyrylpyrrolidin-3-yl)ethanesulfonamide_cis Racemic

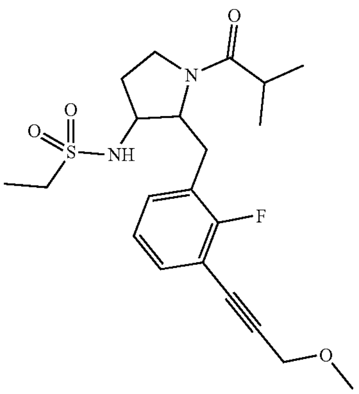 [SMILES: CCS(=O)(=O)NC1CCN(C(=O)C(C)C)C1Cc1cccc(C#CCOC)c1F]

To a 5 mL microwave vial was added N-(2-(3-bromobenzyl)-1-isobutyrylpyrrolidin-3-yl)ethanesulfonamide (75 mg, 0.18 mmol), bis(acetonitrile)dichloropalladium(II) (2.3 mg, 0.01 mmol), cesium carbonate (176 mg, 0.54 mmol), 2-dicyclohexylphosphino-2',4',6' triisopropylbiphenyl (13 mg, 0.03 mmol), methyl propargyl ether (20 μL, 0.23 mmol) and MeCN (2 mL). The reaction mixture was sealed and stirred at 90° C. for 18 h. The reaction mixture was diluted with EtOAc, washed with brine and 1M aq. NaOH, the organic and aqueous layers were separated. The aqueous layer was re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane] and further purified by reverse phase column chromatography (C18-HS cartridge 30 g, 25 mL/min, gradient of 10% methanol in aqueous to 100%, solvents: Aqueous=Water with 0.1% of 28% Ammonia solution, Organic=Methanol) to afford the title compound (6.1 mg, 8% yield).

Example 13. Synthesis of Compound No. 1-10

N-(1-isobutyryl-2-(3-(oxetan-3-ylethynyl)benzyl)pyrrolidin-3-yl)ethanesulfonamide cis Racemic

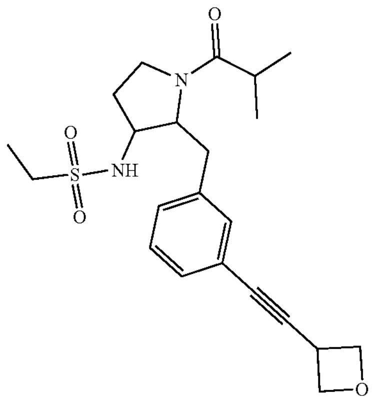 [SMILES: CCS(=O)(=O)NC1CCN(C(=O)C(C)C)C1Cc1cccc(C#CC2COC2)c1]

To a 5 mL microwave vial was added N-(2-(3-bromobenzyl)-1-isobutyrylpyrrolidin-3-yl)ethanesulfonamide (80 mg, 0.19 mmol), bis(acetonitrile)dichloropalladium(II) (2.5 mg, 0.01 mmol), cesium carbonate (188 mg, 0.58 mmol), 2-dicyclohexylphosphino-2',4',6' triisopropylbiphenyl (14 mg, 0.03 mmol), 3-ethynyloxetane (20 mg, 0.25 mmol) and MeCN (2 mL). The reaction mixture was sealed and stirred at 90° C. for 18 h. The reaction mixture was diluted with EtOAc, washed with brine, 1M aq. NaOH, the organic and aqueous layers were separated. The aqueous layer was re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane, then gradient 0% to 10% MeOH in dichloromethane] and further purified by reverse phase column chromatography (C18-HS cartridge 30 g, 25 mL/min, gradient of 10% methanol in aqueous to 100%, solvents: Aqueous=Water with 0.1% of 28% Ammonia solution, Organic=Methanol) to afford the title compound (28.8 mg, 36% yield).

Example 14. Synthesis of Compound No. 1-9

N-(1-isobutyryl-2-(3-((3-methyloxetan-3-yl)ethynyl)benzyl)pyrrolidin-3-yl)ethane-sulfonamide_cis Racemic

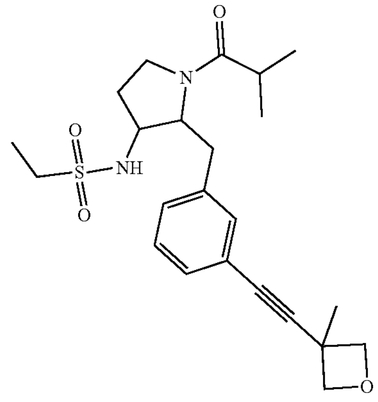 [SMILES: CCS(=O)(=O)NC1CCN(C(=O)C(C)C)C1Cc1cccc(C#CC2(C)COC2)c1]

To a 5 mL microwave vial was added N-(2-(3-bromobenzyl)-1-isobutyrylpyrrolidin-3-yl) ethanesulfonamide (75 mg, 0.18 mmol), bis(acetonitrile)dichloropalladium(II) (2 mg, 0.01 mmol), cesium carbonate (176 mg, 0.54 mmol), 2-dicyclohexylphosphino-2',4',6' triisopropylbiphenyl (13 mg, 0.00 mmol), 3-ethynyl-3-methyloxetane (22 mg, 0.23 mmol) and MeCN (2 mL). The reaction mixture was sealed and stirred at 90° C. for 18 h. The reaction mixture was diluted with EtOAc, washed with brine, 1M aq. NaOH, the organic and aqueous layers were separated. The aqueous layer was re-extracted with EtOAc. The combined organic extract was dried over $MgSO_4$, passed over hydrophobic frit and evaporated in vacuo. The residue was purified by flash column chromatography [gradient 10% to 100% Ethyl Acetate in Iso-hexane, then gradient 0% to 10% MeOH in DCM] and further purified by reverse phase column chromatography (C18-HS cartridge 30 g, 25 mL/min, gradient of 10% methanol in aqueous to 100%, solvents: Aqueous=Water with 0.1% of 28% Ammonia solution, Organic=Methanol) to afford the title compound (34.5 mg, 44% yield).

Example 15. Synthesis of Compound No. 1-8

Step 1: N-((2S,3S)-1-(azetidine-1-carbonyl)-2-(3-bromo-2-fluorobenzyl)pyrrolidin-3-yl)methanesulfonamide

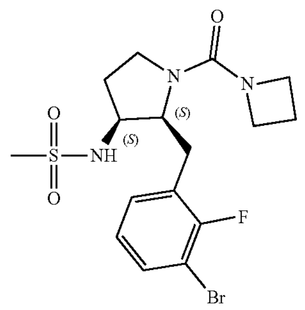

To a solution of N-((2S,3S)-2-(3-bromo-2-fluorobenzyl) pyrrolidin-3-yl)methanesulfonamide, intermediate 6 (450 mg, 1.25 mmol) in tetrahydrofuran (10 mL) was added diisopropylethylamine (1.09 mL, 6.26 mmol), triphosgene (111 mg, 0.38 mmol) at 0° C. After stirring for 1 h, the mixture was concentrated under reduced pressure to give the yellow solid. To the solid in THE (2.0 mL) was added diisopropylethylamine (1.05 mL, 6.04 mmol) and azetidine hydrochloride (400.97 uL, 3.63 mmol). The mixture was stirred at 25° C. for 12 h, poured into the HCl solution (1N, 2.0 mL) and extracted into EtOAc. The organic layer was separated, washed with saturated aqueous $NaHCO_3$ solution (3.0 mL), brine (5.0 mL), the organic layer separated, dried over $Mg_2SO_4$ and concentrated under reduced pressure. The residue was purified by column chromatography ($SiO_2$, Petroleum ether/Ethyl acetate=5/1 to 1/1) to afford the title compound (310 mg, 50% yield) as a yellow solid. $^1$H NMR (400 MHz, chloroform-d) 1.90-2.05 (m, 1H), 2.13-2.30 (m, 3H), 2.82 (s, 3H), 2.86-3.04 (m, 2H), 3.22-3.32 (m, 1H), 3.33-3.43 (m, 11H), 3.75-3.90 (m, 2H), 3.95-4.05 (m, 2H), 4.45-4.60 (m, 1H), 4.67-4.80 (m, 1H), 6.95-7.15 (m, 1H), 7.29-7.36 (m, 1H), 7.39-7.46 (m, 1H).

Step 2: N-((2S,3S)-1-(azetidine-1-carbonyl)-2-(2-fluoro-3-((1-methylcyclopropyl)-ethynyl)benzyl) pyrrolidin-3-yl)methanesulfonamide

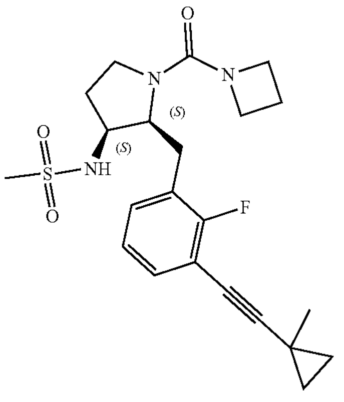

To a solution of N-((2S,3S)-1-(azetidine-1-carbonyl)-2-(3-bromo-2-fluorobenzyl)pyrrolidin-3-yl)methanesulfonamide (30 mg, 69.0 μmol) and 1-ethynyl-1-methyl-cyclopropane (7.0 mg, 90 μmol) in acetonitrile (0.5 mL) was added $Cs_2CO_3$ (68.0 mg, 207 μmol), 2-di-tert-butylphosphino-2,4,6-triisopropylbiphenyl (5.0 mg, 10.0 μmol) and palladium diacetonitrile dichloride (896 ug, 3.45 μmol). The mixture was heated to 90° C. and stirred for 12 h. The mixture was poured into the water (2.0 mL) and extracted with ethyl acetate (3x5.0 mL). The organic layer was washed with brine (5.0 mL), and dried over $Mg_2SO_4$, concentrated under reduced pressure to afford the crude product. The residue was purified by prep-HPLC (neutral condition: column: Waters Xbridge BEH C18 100*30 mm*10 μm; mobile phase: [water (10 mM $NH_4HCO_3$)-ACN]; B %: 300%-600%, 8 min) to afford the title compound (25 mg, 83% yield) as a white solid.

Example 16. Synthesis of Compound No. 1-7

N-((2S,3S)-1-(azetidine-1-carbonyl)-2-(3-(cyclobutylethynyl)-2-fluorobenzyl)-pyrrolidin-3-yl) methanesulfonamide

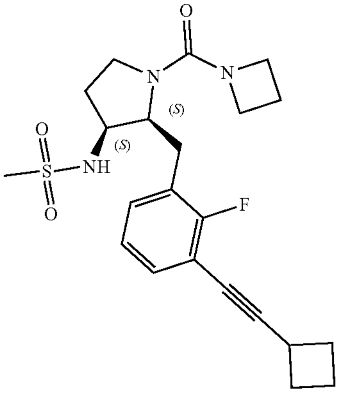

To a solution of N-((2S,3S)-1-(azetidine-1-carbonyl)-2-(3-bromo-2-fluorobenzyl)pyrrolidin-3-yl)methanesulfonamide (55 mg, 127 μmol) and ethynylcyclobutane (15 mg, 190 μmol) in acetonitrile (0.5 mL) was added $Cs_2CO_3$ (124 mg, 380 μmol), palladium diacetonitrile dichloride (1.6 mg, 6.33 μmol). The mixture was stirred at 100° C. for 12 h, poured into water (1.0 mL) and extracted with ethyl acetate (3x3 mL). The organic layer was washed with brine (5.0 mL), dried over $Mg_2SO_4$, filtered and concentrated under reduced pressure to afford the crude product. The residue was purified by prep-HPLC (neutral condition: column: Waters Xbridge BEH C18 100*30 mm*10 μm; mobile phase: [water (10 mM NH4HCO3)-ACN]; B %: 32%-62%, 10 min) to afford the title compound (20 mg, 36% yield) as an off-white solid.

Example 17. Synthesis of Compound No. 1-6

Step 1: N-((2S,3S)-2-(3-bromo-2-fluorobenzyl)pyrrolidin-3-yl)methanesulfonamide hydrochloride

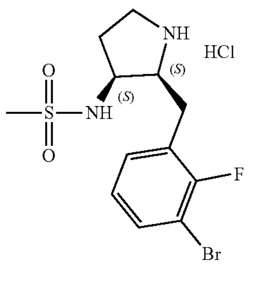

A solution of tert-butyl (2S,3S)-3-amino-2-(3-bromo-fluorobenzyl)pyrrolidine-1-carboxylate_isomer 1, intermediate 5, (740 mg, 1.64 mmol) in HCl/dioxane (4 M, 9.50 mL) at 25° C. was stirred at 25° C. for 12 h. The reaction mixture was concentrated under reduced pressure to afford the title compound (630 mg, 99% yield) which was used without further purification. LCMS (method G): (ESI+): m/z 351 $(M+H)^+$, RT: 0.58 min Step 2: (2S,3S)-2-(3-bromo-2-fluorobenzyl)-N-ethyl-3-(methylsulfonamido)-pyrrolidine-1-carboxamide

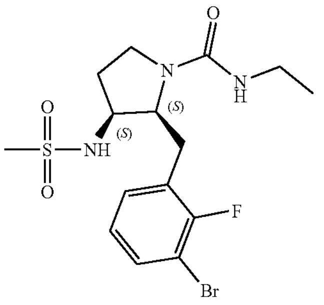

To a solution of N-((2S,3S)-2-(3-bromo-2-fluorobenzyl) pyrrolidin-3-yl)methanesulfonamide hydrochloride (200 mg, 569 μmol) in dichloromethane (5.0 mL) was added triethylamine (238 uL, 1.71 mmol), isocyanatoethane (54 uL, 683 μmol) at 0° C. The mixture was stirred at 25° C. for 12 h, poured into the water (10 mL) and extracted with dichloromethane (3×5.0 mL). The organic layer was washed with brine (5.0 mL), dried over $Mg_2SO_4$ and concentrated under reduced pressure to afford the title compound (80 mg, 33% yield) as a white solid which was used without further purification. LCMS (method H): (ESI+): m/z 422 $(M+H)^+$, RT: 0.62 min Step 3: (2S,3S)—N-ethyl-2-(2-fluoro-3-((1-methylcyclopropyl)ethynyl)benzyl)-3-(methylsulfonamido) pyrrolidine-1-carboxamide

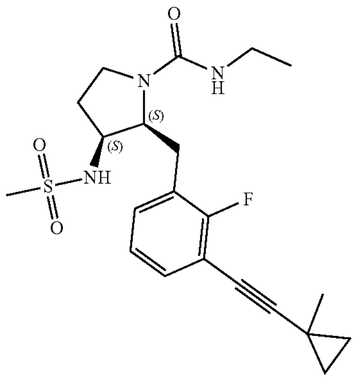

To a solution of (2S,3S)-2-(3-bromo-2-fluorobenzyl)-N-ethyl-3-(methylsulfonamido) pyrrolidine-1-carboxamide (60 mg, 142 μmol) and 1-ethynyl-1-methyl-cyclopropane (15 mg, 185 μmol) in acetonitrile (2.0 mL) was added $Cs_2CO_3$ (139 mg, 426 μmol), 2-di-tert-butylphosphino-2,4,6-triisopropylbiphenyl (10 mg, 21 μmol) and palladium diacetonitrile dichloride (1.8 mg 7.1 μmol). The mixture was heated to 90° C. for 12 h, poured into the water (2.0 mL) and extracted with ethyl acetate (3×5.0 mL). The organic layer was washed with brine (5.0 mL), dried over $MgSO_4$, concentrated under reduced pressure to afford the crude product. The residue was purified by prep-HPLC (neutral condition) to afford the title compound (33 mg, 55% yield) as a white solid.

Example 18 and 19. Synthesis of Compound Nos. 1-4 and 1-5

Step 1: tert-butyl 2-(3-bromo-2-fluorobenzyl)-3-oxopiperidine-1-carboxylate

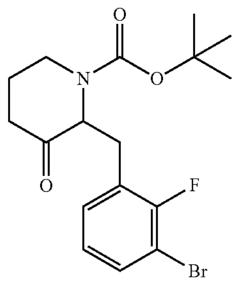 [SMILES: CC(C)(C)OC(=O)N1CCCC(=O)C1Cc1cccc(Br)c1F]

tert-Butyl 3-oxopiperidine-1-carboxylate (50 g, 251 mmol) was dissolved in toluene (500 mL) at room temperature. Pyrrolidine (52 mL, 628 mmol) was added at 0° C. and reaction mixture was stirred at 120° C. for 5 h. The reaction mixture was concentrated in vacuo to afford an orange liquid. The residue was re-dissolved in Acetonitrile (500 mL), 1-bromo-3-(bromomethyl)-2-fluorobenzene (40 g, 151 mmol) and tetrabutylammonium iodide (18.5 g, 50 mmol) were added at 0° C. and the reaction mixture was stirred at 80° C. for 8 h. The mixture was diluted with water (500 mL) and dichloromethane (200 mL). The aqueous solution was further extracted with dichloromethane (2×200 mL). The organic layers were combined and dried ($Na_2SO_4$), the solvent was removed in vacuo to afford crude compound which was purified by normal phase gradient column chromatography (Normal phase, Silica gel), product eluted at 0% to 8% EtOAc in Hexane to afford the title compound (35.5 g, 37% yield) as yellow solid. LCMS (method E): (ESI+): m/z 286 $(M-100)^+$, RT: 2.49 min Step 2: tert-butyl 3-amino-2-(3-bromo-2-fluorobenzyl)piperidine-1-carboxylate_cis Racemic

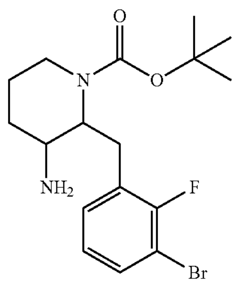 [SMILES: CC(C)(C)OC(=O)N1CCCC(N)C1Cc1cccc(Br)c1F]

tert-Butyl 2-(3-bromo-2-fluorobenzyl)-3-oxopiperidine-1-carboxylate (33.3 g, 86.5 mmol) was dissolved in methanol (600 mL). Ammonium acetate (200 g, 2.59 mol) was added and the reaction mixture was stirred at room temperature for 5 h. Sodium triacetoxyborohydride (37 g 173 mmol) was added at 0° C. and reaction mixture was stirred at room temperature for 5 h and then at 70° C. for 2 h. The reaction mixture was concentrated in vacuo, the residue was then diluted with saturated aqueous $NaHCO_3$ (600 mL) and EtOAc (300 mL). The aqueous layer was further extracted with EtOAc (3×100 mL), the organic layers were combined and dried ($Na_2SO_4$). The solvent was removed in vacuo and the crude product purified by normal phase gradient column chromatography (normal phase, Silicagel), product eluted at 0% to 3% MeOH in dichloromethane to afford the title compound (14.4 g, 43% yield) as yellow solid. LCMS (method E): (ESI+): m/z 331 $(M-56)^+$, RT: 1.58 min Step 3: tert-butyl 2-(3-bromo-2-fluorobenzyl)-3-(methylsulfonamido)piperidine-1-carboxylate_cis Racemic

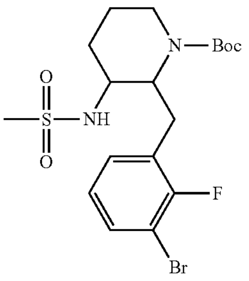 [SMILES: CC(C)(C)OC(=O)N1CCCC(NS(C)(=O)=O)C1Cc1cccc(Br)c1F]

To a solution of tert-butyl 3-amino-2-(3-bromo-2-fluorobenzyl)piperidine-1-carboxylate (1.0 g, 2.58 mmol) in dichloromethane (15 mL) was added methanesulfonyl chloride (220 uL, 2.84 mmol) and triethylamine (899 uL, 6.46 mmol). The mixture was stirred at 20° C. for 12 h, quenched by addition ice water (10 mL) at 0° C. and then extracted with dichloromethane (20 mL) three times. The combined organic layers were washed with saturated sodium chloride solution (10 mL), dried over sodium sulfate, filtered and concentrated under reduced pressure to give a residue. The crude product was triturated with methyl tert-butyl ether (5 mL) at 20° C. for 1 h to afford the title compound (800 mg, 67% yield) as a white solid. LCMS (method H): (ESI+): m/z 365 $(M-100)^+$, RT: 0.77 min Step 4: tert-butyl 2-(2-fluoro-3-((1-methylcyclopropyl)ethynyl)benzyl)-3-(methylsulfonamido)piperidine-1-carboxylate_cis Racemic

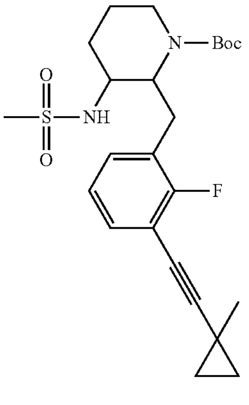

A mixture of tert-butyl 2-(3-bromo-2-fluorobenzyl)-3-(methylsulfonamido)piperidine-1-carboxylate (300 mg, 0.64 mmol), 1-ethynyl-1-methyl-cyclopropane (67.15 mg, 0.84 mmoL) $Pd(CH_3CN)_2Cl_2$ (8.0 mg, 32 µmol), cesium carbonate (630 mg, 1.93 mmol) in acetonitrile (4.0 mL) was degassed and purged with $N_2$ for three times and stirred at 90° C. for 12 h under $N_2$ atmosphere. The reaction mixture was diluted with $H_2O$ (10 mL) and extracted with ethyl acetate (10 mL) three times. The combined organic layers were washed with saturated sodium chloride solution (10 mL) three times, dried over sodium sulfate, filtered and concentrated under reduced pressure to afford a residue. The residue was purified by prep-TLC ($SiO_2$, petroleum ether/ethyl acetate=3/1) to afford the title compound (210 mg, 67% yield) as a white solid. LCMS (method H): (ESI+): m/z 365 $(M+H-100)^+$, RT: 0.85 min Step 5: N-(2-(2-fluoro-3-((1-methylcyclopropyl)ethynyl)benzyl)piperidin-3-yl) methanesulfonamide hydrochloride_cis Racemic

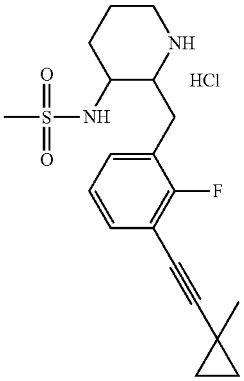

A solution of tert-butyl 2-(2-fluoro-3-((1-methylcyclopropyl)ethynyl)benzyl)-3-(methylsulfonamido)piperidine-1-carboxylate (200 mg, 0.43 mmol) in hydrochloric acid/dioxane (3.0 mL, 4 M) was stirred at 20° C. for 1 h under $N_2$ atmosphere. The reaction mixture was concentrated under reduced pressure to afford the title compound (140 mg, 71% yield) as a white solid which was used without further purification. LCMS (method H): (ESI+): m/z 365 $(M+H)^+$, RT: 0.65 min Step 6: N-((2S,3S)-2-(2-fluoro-3-((1-methylcyclopropyl)ethynyl)benzyl)-1-((R)-oxetane-2-carbonyl)piperidin-3-yl)methanesulfonamide (Isomer 1) and N-((2R,3R)-2-(2-fluoro-3-((1-methylcyclopropyl)ethynyl)benzyl)-1-((R)-oxetane-2-carbonyl)piperidin-3-yl)methanesulfonamide (Isomer 2)

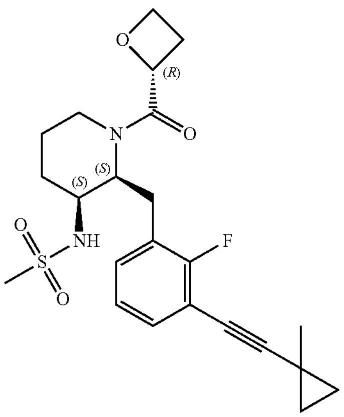

+

-continued

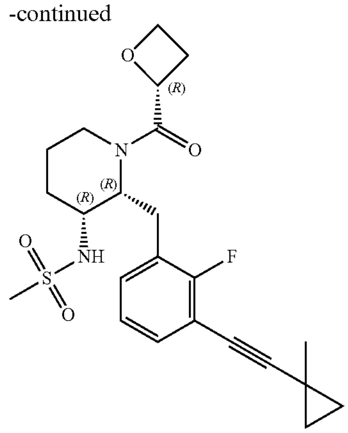

To a mixture of N-(2-(2-fluoro-3-((1-methylcyclopropyl)ethynyl)benzyl)piperidin-3-yl)methanesulfonamide hydrochloride (120 mg, 0.33 mmol) and (2R)-oxetane-2-carboxylic acid (37 mg, 0.36 mmol) in DMF (3.0 mL) was added diisopropylethylamine (172 μL, 0.99 mmol) and HATU (163 mg, 0.43 mmol). The mixture was stirred at 25° C. for 8 h. The solution was poured into water and extracted with ethyl acetate (10 mL) twice. The collected organic layers were combined and concentrated under reduced pressure. The residue was purified by prep-HPLC (basic condition) to afford the title compounds (32 mg, 22% yield, isomer 1) as a white solid and (30 mg, 20% yield, isomer 2) as a white solid.

Example 20. Synthesis of Compound No. 1-3

Step 1: tert-butyl (2S,3S)-3-amino-2-(3-bromobenzyl)pyrrolidine-1-carboxylate_isomer 1

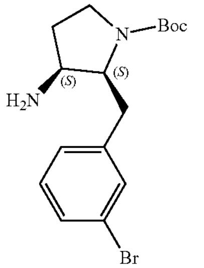

tert-Butyl 3-amino-2-(3-bromobenzyl)pyrrolidine-1-carbolate_cis racemic (intermediate 1) was resolved by SFC Prep using a Chiralpak IC-3 column and isocratic conditions of $CO_2$:(EtOH+0.05% DEA) 50:50. Isomer 1: 99% e.e. retention time=1.05 mins. tert-butyl (2S,3S)-3-amino-2-(3-bromobenzyl)pyrrolidine-1-carboxylate_isomer 1. Isomer 2: 99% e.e. retention time=1.13 mins. tert-butyl (2R,3R)-3-amino-2-(3-bromobenzyl)pyrrolidine-1-carboxylate_isomer 2.

Step 2: tert-butyl (2S,3S)-2-(3-bromobenzyl)-3-(methylsulfonamido)pyrrolidine-1-carboxylate

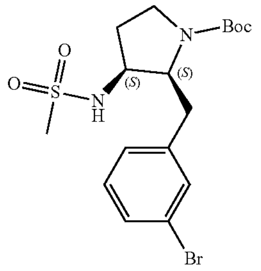

A mixture of tert-butyl (2S,3S)-3-amino-2-(3-bromobenzyl)pyrrolidine-1-carboxylate_isomer 1 (11 g, 31 mmol), triethylamine (4.31 mL, 30.96 mmol) in dichloromethane (150 mL), methylsulfonyl chloride (2.40 mL, 30.96 mmol) was added at 0° C. and then the mixture was stirred at 20° C. for 12 h under $N_2$ atmosphere. The reaction mixture was concentrated and partitioned between water (300 mL) and ethyl acetate (300 mL). The organic phase was separated, washed with ethyl acetate (3×200 mL), dried over $Na_2SO_4$, filtered and concentrated under reduced pressure. The residue was purified by column chromatography ($SiO_2$, Petroleum ether/Ethyl acetate=1/1) to afford the title compound (14 g, 98% yield) as a white solid. $^1H$ NMR (400 MHz, $CDCl_3$-d) δ ppm 7.35-7.25 (m, 2H), 7.15-7.05 (m, 2H), 4.62-4.40 (m, 1H), 4.10-4.28 (m, 1H), 3.98-3.70 (m, 1H), 3.45-3.20 (m, 2H), 2.85-2.75 (m, 1H), 2.75-2.25 (m, 4H), 2.32-2.10 (m, 1H), 1.25-0.94 (m, 9H).

Step 3: N-((2S,3S)-2-(3-bromobenzyl)pyrrolidin-3-yl)methanesulfonamide hydrochloride

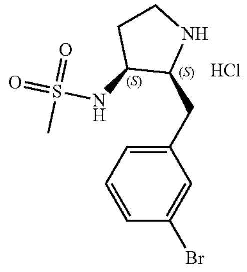

A solution of tert-butyl (2S,3S)-2-(3-bromobenzyl)-3-(methylsulfonamido)pyrrolidine-1-carboxylate (14 g, 35 mmol) in HCl/dioxane (100 mL) was stirred at 20° C. for 16 h. The reaction mixture was concentrated under reduced pressure to give a residue. The crude product was triturated with EtOAc (50 mL) at 20° C. for 30 min to afford the title compound (9.8 g, 85% yield) as a white solid. $^1H$ NMR (400 MHz, MeOD-d4) δ ppm 7.57 (s, 1H), 7.50-7.40 (m, 1H), 7.38-7.20 (m, 2H), 4.38-4.20 (m, 1H), 3.85-3.78 (m, 1H), 3.55-3.40 (m, 1H), 3.35-3.25 (m, 2H), 3.03 (s, 3H), 2.85-2.75 (m, 1H), 2.65-2.35 (m, 1H), 2.32-2.10 (m, 1H).

Step 4: N-((2S,3S)-2-(3-bromobenzyl)-1-((R)-oxetane-2-carbonyl)pyrrolidin-3-yl)methanesulfonamide

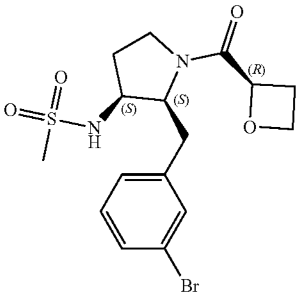

To a mixture of N-((2S,3S)-2-(3-bromobenzyl)pyrrolidin-3-yl)methanesulfonamide (200 mg, 0.60 mmol) and (2R)-oxetane-2-carboxylic acid (67 mg, 0.66 mmol) in DMF (2.0 mL) was added HATU (297 mg, 780 mmol) and diisopropylethylamine (312 μL, 1.80 mmol) in one portion at 25° C. under $N_2$. The mixture was stirred at 25° C. for 12 h. The residue was poured into ice-water (20 mL), the aqueous phase was extracted with ethyl acetate (3×10 mL). The combined organic phase was dried with anhydrous $Na_2SO_4$, filtered and concentrated in vacuo. The residue was purified by prep-TLC ($SiO_2$, PE:EA=0:1) to afford the title compound (73 mg, 27% yield) as colorless oil. LCMS (method H): (ESI+): m/z 417 $(M+H)^+$, RT: 0.58 min Step 5: N-((2S,3S)-2-(3-((1-methylcyclopropyl)ethynyl)benzyl)-1-((R)-oxetane-2-carbonyl)pyrrolidin-3-yl)methanesulfonamide

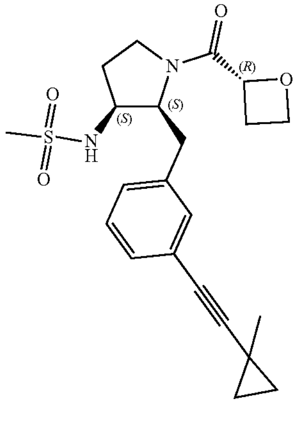

To a mixture of N-((2S,3S)-2-(3-bromobenzyl)pyrrolidin-3-yl)methanesulfonamide (35 mg, 84 μmol) and 1-ethynyl-1-methyl-cyclopropane (9.0 mg, 109 μmol) in acetonitrile (1.0 mL) was added 2-di-tert-butylphosphino-2,4,6-triisopropylbiphenyl (6.0 mg, 13 μmol), $Cs_2CO_3$ (82 mg, 252 μmol) and palladium diacetonitrile dichloride (1.0 mg, 4.2 μmol) at 25° C. under $N_2$. The mixture was stirred at 25° C. for 3 min, then heated to 90° C. and stirred for 12 h. The mixture was cooled to 25° C., the residue poured into ice-water (20 mL) and the aqueous phase extracted with ethyl acetate (3×10 mL). The combined organic phase was dried with anhydrous $Na_2SO_4$, filtered and concentrated in vacuum. The residue was purified by prep-HPLC (neutral condition: column: Waters Xbridge BEH C18 100*30 mm*10 μm; mobile phase: [water (10 mM $NH_4HCO_3$)-ACN]; B %: 25%-55%, 8 min) to afford the title compound (15 mg, 21% yield) as a white solid.

Example 21. Synthesis of Compound No. 1-2

Step 1: N-((2S,3S)-2-(3-bromo-2-fluorobenzyl)-1-((R)-oxetane-2-carbonyl)-pyrrolidin-3-yl)methanesulfonamide

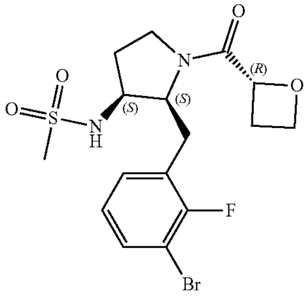

To a solution of N-((2S,3S)-2-(3-bromo-2-fluorobenzyl)pyrrolidin-3-yl)methanesulfonamide (intermediate 6) (1.0 g, 2.85 mmol) in DMF (10 mL) was added diisopropylethylamine (1.49 mL, 8.54 mmol), (2R)-oxetane-2-carboxylic acid (436 mg, 4.27 mmol) and HATU (1.62 g, 4.27 mmol). The mixture was stirred under $N_2$ at 25° C. for 12 h. The reaction mixture was partitioned between $H_2O$ (10 mL) and EtOAc (30 mL). The organic phase was separated, washed with brine (20 mL), dried over $MgSO_4$, filtered and concentrated under reduced pressure to give a residue. The residue was purified by prep-HPLC (Basic condition: column: Waters Xbridge Prep OBD C18 150*40 mm*10 μm; mobile phase: [water (0.05% NH3H2O+10 mM NH4HCO3)-ACN]; B %: 15%-45%, 8 min) to afford the title compound (300 mg, 24% yield) as a white solid. LCMS (method H): (ESI+): m/z 435 $(M+H)^+$, RT: 0.65 min Step 2: N-((2S,3S)-2-(2-fluoro-3-((1-(trifluoromethyl)cyclopropyl)ethynyl)benzyl)-1-((R)-oxetane-2-carbonyl)pyrrolidin-3-yl)methanesulfonamide

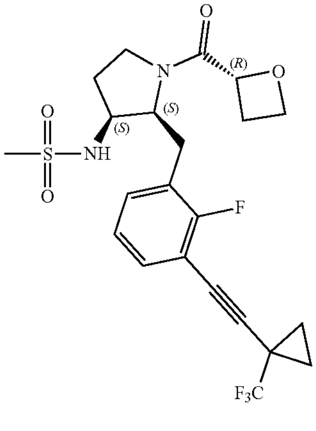

To a mixture of N-((2S,3S)-2-(3-bromo-2-fluorobenzyl)-1-((R)-oxetane-2-carbonyl)pyrrolidin-3-yl)methanesulfonamide (30 mg, 69 μmol) and 1-ethynyl-1-(trifluoromethyl) cyclopropane (12 mg, 90 μmol) in acetonitrile (1.0 mL) was added 2-di-tert-butylphosphino-2,4,6-triisopropylbiphenyl (5.0 mg, 10 μmol), $Cs_2CO_3$ (67 mg, 207 μmol) and palladium diacetonitrile dichloride (894 μg, 3.5 μmol) in one portion at 25° C. under $N_2$. The mixture was stirred at 25° C. for 3 min, then heated to 90° C. and stirred for 12 h. The mixture was cooled to 25° C., the residue poured into ice-water (5.0 mL) and the aqueous phase was extracted with ethyl acetate (3×5.0 mL). The combined organic phase was dried with anhydrous $Na_2SO_4$, filtered and concentrated in vacuum. The residue was purified by prep-HPLC (neutral condition: column: Phenomenex Gemini-NX C18 75*30 mm*3 μm; mobile phase: [water (10 mM $NH_4HCO_3$)-ACN]; B %: 20%-45%, 12 min) to afford the title compound (15 mg, 45% yield) as a white solid.

Example 22. Synthesis of Compound No. 1-1

N-((2S,3S)-2-(2-fluoro-3-((1-methylcyclopropyl)ethynyl)benzyl)-1-((R)-oxetane-2-carbonyl)pyrrolidin-3-yl)methanesulfonamide

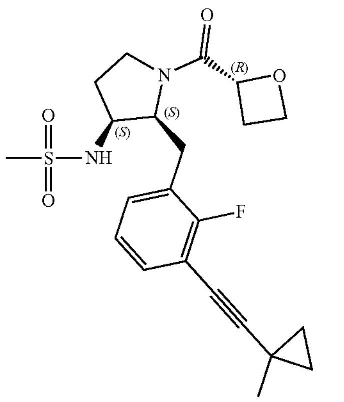

To a mixture of N-((2S,3S)-2-(3-bromo-2-fluorobenzyl)-1-((R)-oxetane-2-carbonyl)pyrrolidin-3-yl)methanesulfonamide (35 mg, 80 μmol) and 1-ethynyl-1-methyl-cyclopropane (8.0 mg, 104 μmol) in acetonitrile (1.0 mL) was added palladium diacetonitrile dichloride (1.0 mg, 4.0 μmol), 2-di-tert-butylphosphino-2,4,6-triisopropylbiphenyl (6.0 mg, 12 μmol) and $Cs_2CO_3$ (79 mg, 241 μmol) in one portion at 25° C. under $N_2$. The mixture was stirred at 25° C. for 3 min, then heated to 90° C. and stirred for 12 h. The residue was poured into ice-water (10 mL) and the aqueous phase was extracted with ethyl acetate (3×5.0 mL). The combined organic phase was dried with anhydrous $Na_2SO_4$, filtered and concentrated in vacuo. The residue was purified by prep-HPLC (neutral condition: column: Waters Xbridge BEH C18 100*30 mm*10 μm; mobile phase: [water (10 mM $NH_4HCO_3$)-ACN]; B %: 30%-60%, 10 min) to afford the title compound (12 mg, 34% yield) as a white solid.

Example 23. Characterization of Exemplary Compounds Prepared in Examples 1-15

Exemplary Compounds prepared according to Examples 1-15 are characterized by NMR and LCMS. Characterization data are shown in the table below.

| Compound No. | Characterization Data |
|---|---|
| 1-22 | 1H NMR (400 MHz, DMSO-d6) δ 7.61-7.22 (m, 10H), 5.08 (s, 1H), 4.35 (q, 1H), 3.92-3.65 (m, 3H), 3.04-2.82 (m, 3H), 2.72-2.59 (m, 1H), 2.16-1.99 (m, 1H), 1.88 (p, 1H), 1.26 (s, 3H), 1.25 (s, 3H), 1.11 (t, 3H)<br>LCMS (method B): m/z 455 $(M + H)^+$ (ES+), at 3.97 min |
| 1-21 | 1H NMR (400 MHz, DMSO-d6) δ 7.42 (d, 1H), 7.35-7.23 (m, 2H), 7.20-7.08 (m, 2H), 5.07 (s, 1H), 4.30 (q, 1H), 3.89-3.60 (m, 3H), 3.02-2.68 (m, 3H), 2.59 (dd, 1H), 2.04 (q, 1H), 1.86 (q, 1H), 1.52 (tt, 1H), 1.23 (s, 6H), 1.08 (t, 3H), 0.97-0.82 (m, 2H), 0.70 (dq, 2H).<br>LCMS (method D): m/z 419 $(M + H)^+$ (ES+), at 3.78 min |
| 1-20 | 1H NMR (400 MHz, DMSO-d6) δ 7.08-6.89 (m, 2H), 6.84 (t, 1H), 6.69 (t, 1H), 4.28-3.78 (m, 1H), 3.58 (ddt, 1H), 3.33-3.15 (m, 2H), 2.94-2.59 (m, 3H), 2.21-2.07 (m, 1H), 1.97-1.68 (m, 2H), 1.54-1.25 (m, 2H), 0.98 (td, 3H), 0.67-0.62 (m, 2H), 0.58-0.42 (m, 6H), 0.02 (d, 2H).<br>LCMS (method B): m/z 421 $(M + H)^+$ (ES+), at 3.73 min |
| 1-19 | 1H NMR (400 MHz, DMSO-d6) δ 7.34-7.13 (m, 2H), 7.08 (t, 1H), 6.97 (t, 1H), 4.48-3.97 (m, 1H), 3.78 (ddt, 1H), 3.56-3.35 (m, 1H), 3.28-2.84 (m, 4H), 2.45 (d, 1H), 2.35-2.22 (m, 1H), 2.13 (dd, 1H), 2.06-1.73 (m, 5H), 1.67-1.51 (m, 2H), 1.22 (q, 3H), 1.02 (ddt, 1H), 0.96-0.85 (m, 2H), 0.79-0.66 (m, 2H).<br>LCMS (method B): m/z 433 $(M + H)^+$ (ES+), at 3.95 min |
| 1-18 | 1H NMR (400 MHz, DMSO-d6) δ 7.51 (s, 1H), 7.24 (ddt, 2H), 7.03 (t, 1H), 4.32 (ddd, 1H), 3.71 (q, 3H), 3.54 (q, 2H), 3.30 (d, 2H), 3.18-2.81 (m, 4H), 2.20-1.89 (m, 4H), 1.58 (tt, 1H), 1.21 (t, 3H), 0.98-0.87 (m, 2H), 0.79-0.69 (m, 2H).<br>LCMS (method B): m/z 434 $(M + H)^+$ (ES+), at 3.52 min |
| 1-16 | LCMS (method D): m/z 434 $(M + H)^+$ (ES+), at 3.97 min |
| 1-15 | LCMS (method D): m/z 434 $(M + H)^+$ (ES+), at 3.97 min |
| 1-17 | 1H NMR (400 MHz, DMSO-d6) δ 7.67-7.53 (m, 2H), 7.24 (dd, 1H), 7.16 (dd, 1H), 4.38-4.24 (m, 1H), 3.80 (q, 3H), 3.63 (q, 2H), 3.28-3.21 (m, 1H), 3.18-3.07 (m, 2H), 3.06-2.88 (m, 2H), 2.73 (dd, 1H), 2.14-1.98 (m, 3H), 1.83-1.68 (m, 1H), 1.56 (tt, 1H), 1.17 (t, 3H), 0.96-0.85 (m, 2H), 0.82-0.69 (m, 2H).<br>LCMS (method B): m/z 417 $(M + H)^+$ (ES+), at 3.00 min |
| 1-14 | 1H NMR (400 MHz, DMSO-d6) δ 7.56 (s, 1H), 7.32-7.01 (m, 4H), 4.15-4.01 (m, 1H), 3.80 (ddt, 1H), 3.55-3.38 (m, 1H), 3.21-3.04 (m, 3H), 3.01-2.80 (m, 2H), 2.62-2.55 (m, 1H), 2.20-2.03 (m, 1H), 2.01-1.79 (m, 1H), 1.53 (tdt, 1H), 1.18 (dt, 3H), 0.92-0.29 (m, 6H), 0.91-0.84 (m, 2H), 0.72-0.67 (m, 2H).<br>LCMS (method B): m/z 403 $(M + H)^+$ (ES+), at 3.71 min |
| 1-13 | 1H NMR (400 MHz, DMSO-d6) δ 7.56 (s, 1H), 7.31-7.05 (m, 4H), 4.32-4.03 (m, 1H), 3.80 (ddt, 1H), 3.46 (ddd, 2H), 3.22-3.06 (m, 1H), 3.01-2.78 (m, 3H), 2.65-2.55 (m, 1H), 2.42 (dd, 1H), 2.20-2.03 (m, 1H), 2.03-1.81 (m, 3H), 1.78-1.49 (m, 6H), 1.18 (dt, 3H), 0.98-0.24 (m, 6H).<br>LCMS (method B): m/z 431 $(M + H)^+$ (ES+), at 4.43 min |
| 1-12 | 1H NMR (400 MHz, DMSO-d6) δ 7.53 (s, 1H), 7.32-7.00 (m, 4H), 4.18 (dd, 1H), 3.80 (ddd, 1H), 3.55-3.38 (m, 2H), 3.22-3.05 (m, 1H), 3.04-2.85 (m, 2H), 2.71-2.55 (m, 1H), 2.47-2.30 (m, 1H), 2.21-2.03 (m, 1H), 1.90 (dt, 1H), 1.28 (d, 9H), 1.19 (dt, 3H), 0.98-0.28 (m, 6H). |

-continued

| Compound No. | Characterization Data |
|---|---|
| | LCMS (method B): m/z 419 $(M + H)^+$ (ES+), at 4.30 min |
| 1-11 | 1H NMR (400 MHz, DMSO-d6) δ 7.57 (d, 1H), 7.36-7.09 (m, 4H), 4.30 (d, 2H), 4.15-3.71 (m, 2H), 3.51-3.38 (m, 2H), 3.31 (d, 3H), 3.20-3.05 (m, 1H), 3.01-2.82 (m, 2H), 2.70-2.53 (m, 1H), 2.21-1.99 (m, 1H), 1.90 (dt, 1H), 1.64 (p, 1H), 1.16 (dt, 3H), 0.95-0.19 (m, 6H). LCMS (method B): m/z 407 $(M + H)^+$ (ES+), at 3.09 min |
| 1-10 | 1H NMR (400 MHz, DMSO-d6) δ 7.56 (d, 1H), 7.35-7.07 (m, 4H), 4.79 (ddd, 2H), 4.59 (ddd, 2H), 4.33-4.02 (m, 2H), 3.90-3.72 (m, 1H), 3.55-3.40 (m, 1H), 3.10 (dd, 1H), 3.03-2.81 (m, 2H), 2.65-2.53 (m, 1H), 2.43 (dd, 1H), 2.20-2.03 (m, 1H), 2.01-1.83 (m, 1H), 1.66 (p, 1H), 1.17 (dt, 3H), 1.00-0.21 (m, 6H). LCMS (method B): m/z 419 $(M + H)^+$ (ES+), at 2.94 min |
| 1-9 | $^1$H NMR (400 MHz, DMSO-$d_6$) δ 7.72-7.42 (m, 1H), 7.37-7.06 (m, 4H), 4.73 (t, 2H), 4.43 (d, 2H), 4.34-4.01 (m, 1H), 3.82 (s, 1H), 3.55-3.39 (m, 2H), 3.22-3.07 (m, 1H), 3.06-2.83 (m, 2H), 2.71-2.53 (m, 1H), 2.23-2.04 (m, 1H), 2.00-1.83 (m, 1H), 1.74-1.65 (m, 1H), 1.63 (d, 3H), 1.19 (dt, 3H), 0.99-0.16 (m, 6H). LCMS (method B): m/z 433 $(M + H)^+$ (ES+), at 3.24 min |
| 1-8 | $^1$H NMR (400 MHz, methanol-d4) δ 7.21 (t, 2H), 7.05-6.98 (m, 1H), 4.62 (s, 1H), 4.53-4.44 (m, 1H), 3.95-3.80 (m, 3H), 3.74 (q, 2H), 3.50-3.40 (m, 1H), 3.30-3.20 (m, 1H), 2.98 (s, 3H), 2.95-2.90 (m, 1H), 2.75-2.60 (m, 1H), 2.34-2.24 (m, 1H), 2.15-2.08 (m, 2H), 2.08-1.97 (m, 1H), 1.34 (s, 3H), 0.98-0.93 (m, 2H), 0.75-0.70 (m, 2H). LCMS (method F): m/z 434 $(M + H)^+$ (ES+), at 2.39 min |
| 1-7 | $^1$H NMR (400 MHz, methanol-$d_4$) δ 7.26-7.20 (m, 2H), 7.05-6.99 (m, 1H), 4.69-4.50 (br, 1H), 4.54-4.46 (m, 1H), 3.89 (q, 3H), 3.80-3.65 (m, 2H), 3.50-3.40 (m, 1H), 3.26(s, 1H), 2.98 (s, 3H), 2.97-2.92 (m, 1H), 2.74-2.67 (m, 1H), 2.41-2.32 (m, 2H), 2.29-2.10 (m, 1H), 2.23-2.16 (m, 2H), 2.16-2.10 (m, 2H), 2.09-1.91 (m, 3H). LCMS (method F): m/z 434 $(M + H)^+$ (ES+), at 2.43 min |
| 1-6 | $^1$H NMR (400 MHz, Acetonitrile-$d_3$) δ 7.22 (ddt, 2H), 7.01 (t, 1H), 5.54 (d, 1H), 4.51 (s, 1H), 4.28 (ddd, 1H), 3.91 (dd, 1H), 3.38-3.25 (m, 2H), 3.04-2.96 (m, 1H), 2.93 (s, 3H), 2.90-2.76 (m, 1H), 2.63-2.52 (m, 1H), 2.25 (dtd, 1H), 2.05-2.00 (m, 1H), 1.35 (s, 3H), 1.03-0.95 (m, 2H), 0.86 (t, 3H), 0.80-0.72 (m, 2H). LCMS (method I): m/z 422 $(M + H)^+$ (ES+), at 2.78 min |
| 1-5 | $^1$H NMR (400 MHz, DMSO-d6) δ ppm 7.49-7.43 (m, 1H), 7.30-7.13 (m, 2H), 7.11-6.95 (m, 1H), 5.12-4.93 (m, 1H), 4.42-4.35 (m, 1H), 4.34-4.29 (m, 1H), 4.26-4.14 (m, 1H), 3.70-3.18 (m, 1H), 3.16-3.03 (m, 1H), 3.02-2.95 (m, 4H), 2.95-2.79 (m, 2H), 2.69-2.58 (m, 1H), 2.34-2.23 (m, 1H), 1.76-1.63 (m, 3H), 1.48 (br s, 1H), 1.33-1.30 (m, 3H), 0.97-0.92 (m, 2H), 0.78-0.73 (m, 2H). LCMS (method F): m/z 449 $(M + H)^+$ (ES+), at 2.30 min |
| 1-4 | $^1$H NMR (400 MHz, DMSO-d6) δ ppm 7.47 (dd, 1H), 7.31-7.13 (m, 2H), 7.10-6.97 (m, 1H), 5.11 (dd, 1H), 4.95-4.47 (m, 1H), 4.42-4.33 (m, 1H), 4.27-4.17 (m, 1H), 4.16-3.90 (m, 1H), 3.48-3.36 (m, 1H), 3.26-3.11 (m, 1H), 2.98 (s, 4H), 2.94-2.80 (m, 1H), 2.69-2.61 (m, 1H), 2.34-2.09 (m, 1H), 1.78-1.63 (m, 3H), 1.45 (br s, 1H), 1.32 (s, 3H), 0.98-0.93 (m, 2H), 0.79-0.72 (m, 2H). LCMS (method F): m/z 449 $(M + H)^+$ (ES+), at 2.36 min |

-continued

| Compound No. | Characterization Data |
|---|---|
| 1-3 | $^1$H NMR (400 MHz, DMSO-$d_6$) δ 7.53 (s, 1H), 7.36-7.05 (m, 4H), 5.21 (dd, 1H), 4.52 (ddd, 1H), 4.40-4.28 (m, 2H), 4.24 (q, 1H), 3.91-3.72 (m, 2H), 3.24 (q, 1H), 2.83 (d, 4H), 2.70-2.58 (m, 2H), 2.09 (dd, 1H), 1.90-1.80 (m, 1H), 1.31 (d, 3H), 0.92 (dq, 2H), 0.73 (p, 2H). LCMS (method F): m/z 417 $(M + H)^+$ (ES+), at 2.22 min |
| 1-2 | $^1$H NMR (400 MHz, Acetonitrile-$d_3$) δ 7.32 (t, 2H), 7.10 (dt, 1H), 5.61 (d, 1H), 5.15 (dd, 1H), 4.69-4.48 (m, 1H), 4.45-4.23 (m, 1H), 4.06-3.61 (m, 1H), 3.48-3.28 (m, 2H), 3.13-2.98 (m, 1H), 2.95 (d, 3H), 2.81 (dddd, 1H), 2.68-2.41 (m, 2H), 2.37-2.24 (m, 1H), 2.14-2.02 (m, 1H), 1.47 (dt, 2H), 1.36 (dt, 2H). LCMS (method F): m/z 489 $(M + H)^+$ (ES+), at 2.29 min |
| 1-1 | $^1$H NMR (400 MHz, Acetonitrile-$d_3$) δ 7.35-7.14 (m, 2H), 7.05 (dt, 1H), 5.62 (dd, 1H), 5.15 (dd, 1H), 4.72-4.23 (m, 3H), 4.05-3.79 (m, 1H), 3.48-3.28 (m, 2H), 3.04 (dd, 1H), 2.94 (d, 3H), 2.87-2.70 (m, 1H), 2.68-2.36 (m, 2H), 2.28-2.04 (m, 1H), 1.36 (d, 3H), 0.98 (d, 2H), 0.78 (dd, 2H). LCMS (method F): m/z 435 $(M + H)^+$ (ES+), at 2.22 min |

Example 17. Orexin Type 2 Receptor Agonist Activity of Exemplary Compounds

Stable cell line generation. Obtainment of cells stably expressing either human orexin type 2 or human orexin type 1 receptor: to obtain a stable cell line the Orexin receptor cDNA was inserted into pcDNA3.1(+) plasmid vector and clones identified by G418 drug resistance selection. Clones demonstrating functional activity Orexin A were selected and taken into continuous culture. A single clone for OX2R-CHO and OX1R-CHO were grown in bulk and frozen to generate a cell bank for routine screening.

Measurement of orexin type 2 receptor agonist activity. Chinese hamster ovary (CHO) cells expressing human orexin type 2 receptor (hOX2R) or human orexin type 2 receptor (hOX1R) were seeded in each well of 384 well black clear bottom plates (BD Flacon) at 10,000 cells per well and cultured for 24 hr in an Ham's F12 (Gibco) medium containing 10% fetal calf serum (Sigma Aldrich) under the conditions of 37° C., 5% $CO_2$. After removal of the medium, 50 μl of assay buffer 1 (0.1% bovine serum albumin (Sigma Aldrich), 20 mM HEPES (Molecular Dimensions), 250 mM probenecid (Sigma Aldrich), 1× Calcium 5 dye (Molecular Devices) in Hank's balanced salt solution (Invitrogen)) was added, and the cells were incubated for 60 min under the conditions of 37° C., 5% $CO_2$. A test compound was dissolved in dimethyl sulfoxide (Sigma Aldrich) to 10 mM, and then diluted with assay buffer 2 (20 mM HEPES, Hank's balanced salt solution, 0.1% bovine serum albumin). For the reaction, a test compound solution (10 μl) was added using Fluorescent Imaging Plate Reader TETRA (FLIPR TETRA: manufactured by Molecular Devices), a fluorescence value (excitation wavelength 488 nm, measurement wavelength 570 nm) of each well was measured every one second for 2 min, and the agonist activity was determined using the area of the fluorescence value as an indicator of intracellular $Ca^{2+}$ concentration. The agonist activity of the test compound was calculated assuming that the fluorescence value of the well added with only the dilution buffer was 0% and the fluorescence value of the well added with 10 nM human orexin A (Tocris) buffer was 100%. The agonist activity values $EC_{50}$ and $E_{max}$ of each compound are shown in Table 1 below. As used herein, $E_{max}$ indicates the value at 10 μM concentration when orexin A is converted to a full agonist (maximum value of agonist activity: 100%).

Values of hOx2 $pEC_{50}$ in Table A are presented in ranges, in which "+"<7.0, 7.0≤"+" <8.0, 8.0≤"+++"<9.0, and 9.0≤"++++"<10.0.

Values of hOx2 $E_{max}$ in Table A are presented in ranges, in which 40≤"F"<50, 50≤"E" <60, 60≤"D"<70, 70≤"C"<80, 80≤"B"<90, and 90≤"A".

TABLE 1

| Compound No. | hOx2 $pEC_{50}$ | hOx2 $E_{max}$ |
|---|---|---|
| 1-1 | ++ | A |
| 1-2 | ++ | A |
| 1-3 | ++ | A |
| 1-4 | + | D |
| 1-5 | ++ | A |
| 1-6 | ++ | A |
| 1-7 | ++ | A |
| 1-8 | +++ | A |
| 1-9 | + | A |
| 1-10 | + | C |
| 1-11 | + | C |
| 1-12 | + | A |
| 1-13 | + | A |
| 1-14 | + | A |
| 1-15 | + | C |
| 1-16 | +++ | A |
| 1-17 | + | B |
| 1-18 | ++ | A |
| 1-19 | ++ | A |
| 1-20 | ++ | A |
| 1-21 | + | B |
| 1-22 | + | A |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I):

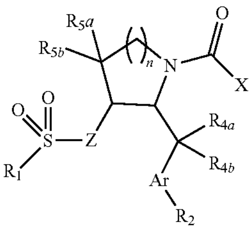

(I)

or a pharmaceutically acceptable salt thereof, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is oxo, halogen, —CN, —OH, —O($C_1$-$C_6$ alkyl), —$NH_2$, —NH($C_1$-$C_6$ alkyl), or —N($C_1$-$C_6$ alkyl)$_2$;

Z is —O— or —$NR_Z$—;

$R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —O($C_1$-$C_6$ alkyl), —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_3$-$C_7$ cycloalkyl, or 3- to 7-membered heterocycloalkyl;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_2$ is $C_2$-$C_6$ alkynyl optionally substituted with one or more Res;

each $R_{2S}$ independently is oxo, halogen, —CN, —OH, —O($C_1$-$C_6$ alkyl), —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ cycloalkyl, or 3- to 7-membered heterocycloalkyl is optionally substituted with one or more $R_{2SS}$;

each $R_{2SS}$ independently is oxo, halogen, —CN, —OH, —$NH_2$, $C_1$-$C_6$ alkyl, $C_2$-$C_6$ alkenyl, or $C_2$-$C_6$ alkynyl, or $C_1$-$C_6$ haloalkyl;

$R_{4a}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{4b}$ is H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

$R_{5a}$ and $R_{5b}$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_{5S}$; or $R_{5a}$ and $R_{5a}$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_{5S}$;

each $R_{5S}$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl; and n is 0, 1, 2, or 3.

2. The compound of claim 1, wherein:

X is —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_3$-$C_7$ cycloalkyl, or 3- to 7-membered heterocycloalkyl is optionally substituted with one or more $R_{X1}$;

each $R_{X1}$ independently is halogen, —OH, or —O($C_1$-$C_6$ alkyl);

Z is —NH—;

$R_1$ is —NH($C_1$-$C_6$ alkyl), —N($C_1$-$C_6$ alkyl)$_2$, $C_1$-$C_6$ alkyl, or 3- to 7-membered heterocycloalkyl, wherein the —NH($C_1$-$C_6$ alkyl), —N($C_1$-$C_6$ alkyl)$_2$, $C_1$-$C_6$ alkyl, or 3- to 7-membered heterocycloalkyl is optionally substituted with one or more $R_{1S}$;

each $R_{1S}$ independently is halogen;

Ar is $C_6$-$C_{10}$ aryl or 5- to 10-membered heteroaryl, wherein the $C_6$-$C_{10}$ aryl or 5- to 10-membered heteroaryl is optionally substituted with one or more $R_A$;

each $R_A$ independently is halogen or —O($C_1$-$C_6$ alkyl);

$R_2$ is $C_2$-$C_6$ alkynyl optionally substituted with one or more $R_{2S}$;

each $R_{2S}$ independently is —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl, wherein the —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl is optionally substituted with one or more $R_{2SS}$;

each $R_{2SS}$ independently is halogen, $C_1$-$C_6$ alkyl, or $C_1$-$C_6$ haloalkyl;

$R_{4a}$ is H;

$R_{4b}$ is H;

$R_{5a}$ and $R_{5b}$ each independently are H or halogen; or $R_{5a}$ and $R_{5a}$, together with the atom they attach to, form $C_3$-$C_7$ cycloalkyl; and n is 1 or 2.

3. The compound of claim 1, wherein X is —O($C_1$-$C_6$ alkyl) optionally substituted with one or more $R_{X1}$.

4. The compound of claim 1, wherein X is —NH($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is optionally substituted with one or more $R_{X1}$.

5. The compound of claim 1, wherein X is $C_1$-$C_6$ alkyl optionally substituted with one or more $R_{X1}$.

6. The compound of claim 1, wherein X is $C_3$-$C_7$ cycloalkyl or 3- to 7-membered heterocycloalkyl, wherein the cycloalkyl or heterocycloalkyl is optionally substituted with one or more $R_{X1}$.

7. The compound of claim 1, wherein X is oxetanyl or azetidinyl, wherein the oxetanyl or azetidinyl is optionally substituted with one or more $R_{X1}$.

8. The compound of claim 1, wherein Z is —NH—.

9. The compound of claim 1, wherein $R_1$ is $C_1$-$C_6$ alkyl, —$NH_2$, —NH($C_1$-$C_6$ alkyl), or —N($C_1$-$C_6$ alkyl)$_2$, wherein the $C_1$-$C_6$ alkyl, —NH($C_1$-$C_6$ alkyl) or —N($C_1$-$C_6$ alkyl)$_2$ is optionally substituted with one or more $R_{1S}$.

10. The compound of claim 1, wherein $R_1$ is $CH_3$ or $CH_2CH_3$.

11. The compound of claim 1, wherein Ar is phenyl or pyridinyl, wherein the phenyl or pyridinyl is optionally substituted with one or more $R_A$, wherein at least one $R_A$ is halogen, —CN, —OH, —O($C_1$-$C_6$ alkyl), —$NH_2$, —NH ($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

12. The compound of claim 1, wherein $R_2$ is ethynyl optionally substituted with one or more $R_{2S}$.

13. The compound of claim 1, wherein at least one $R_{2S}$ is —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl, wherein the —O($C_1$-$C_6$ alkyl), $C_1$-$C_6$ alkyl, $C_6$-$C_{10}$ aryl, $C_3$-$C_7$ cycloalkyl, or 3- to 7-membered heterocycloalkyl is optionally substituted with one or more $R_{2SS}$.

14. The compound of claim 1, wherein at least one Res is $C_3$-$C_7$ cycloalkyl optionally substituted with one or more $R_{2SS}$.

15. The compound of claim 1, wherein at least one Res is 3- to 7-membered heterocycloalkyl optionally substituted with one or more $R_{2SS}$.

16. The compound of claim 1, wherein the compound is selected from

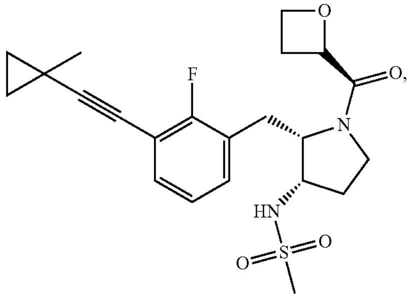

-continued
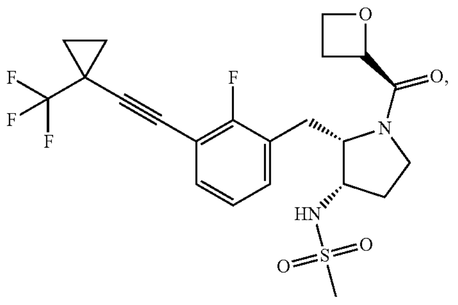
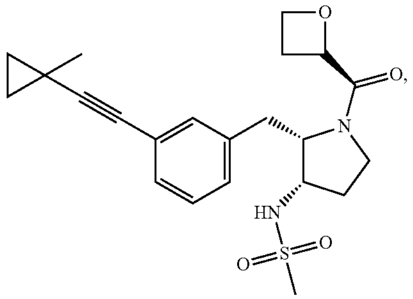
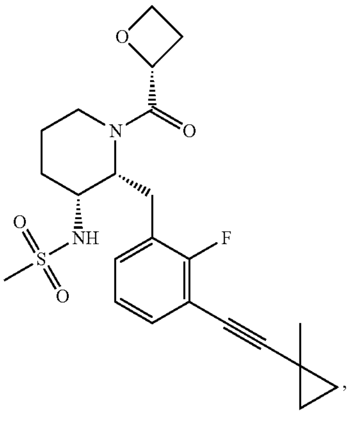
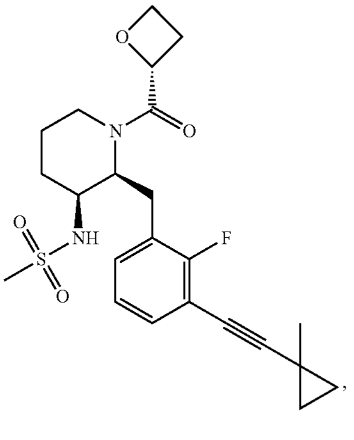
-continued
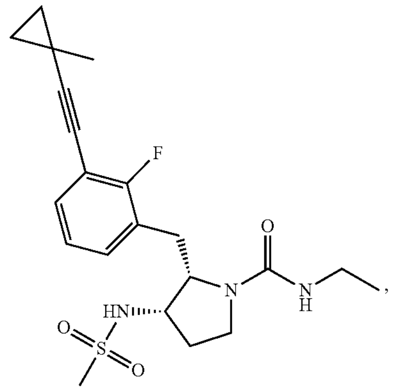
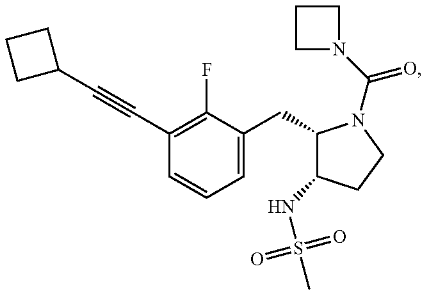
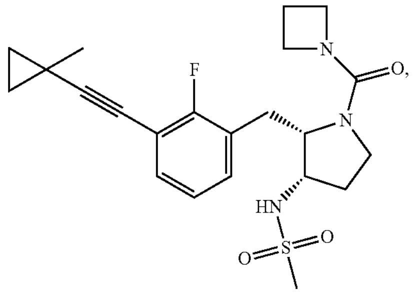
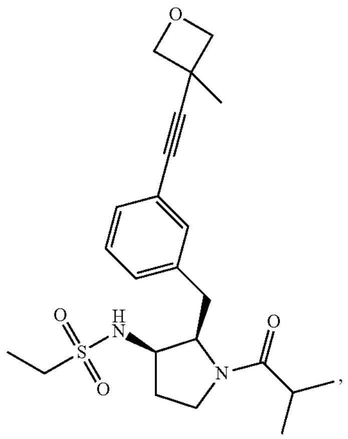

-continued
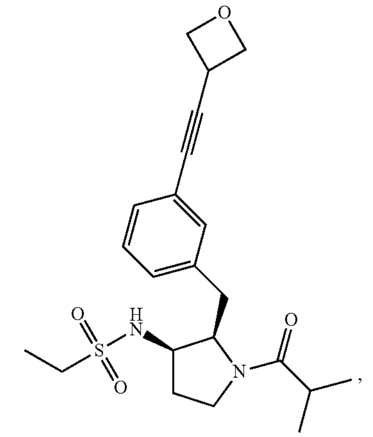
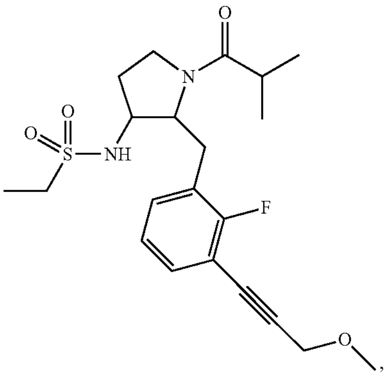
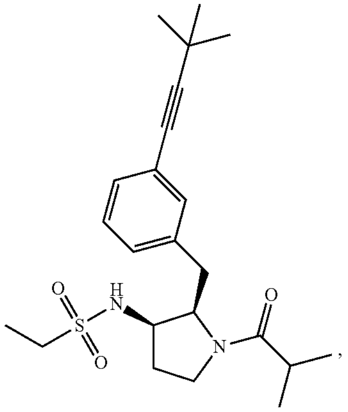
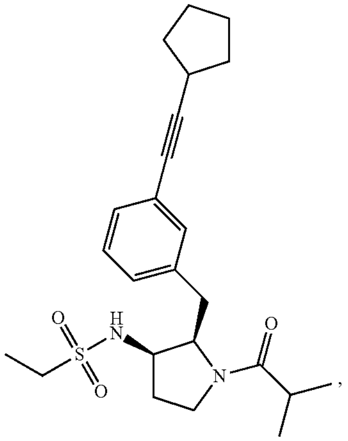
-continued
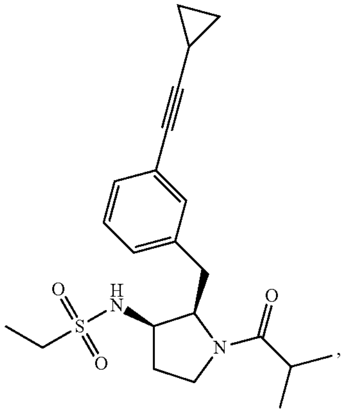
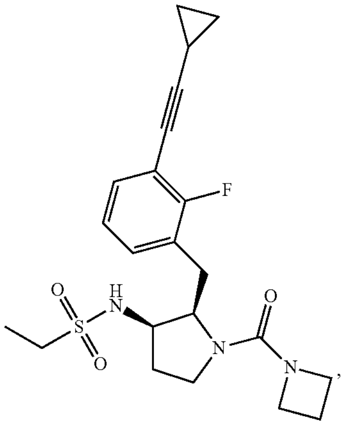
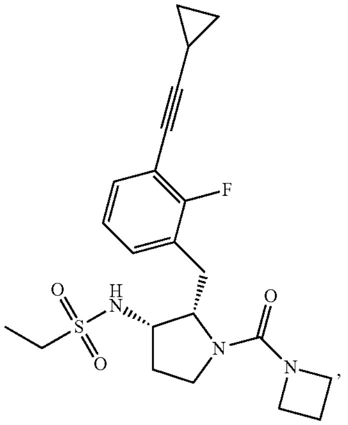
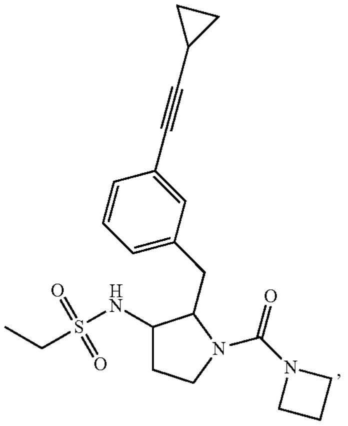

-continued
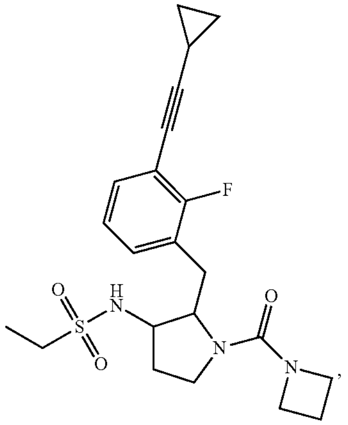
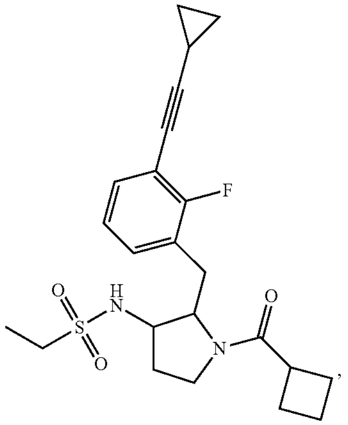
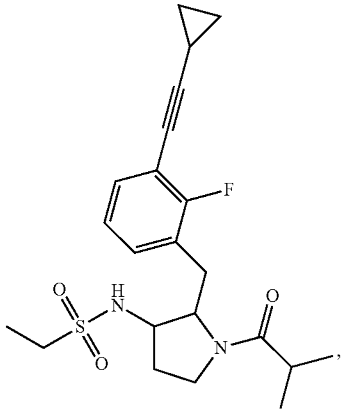
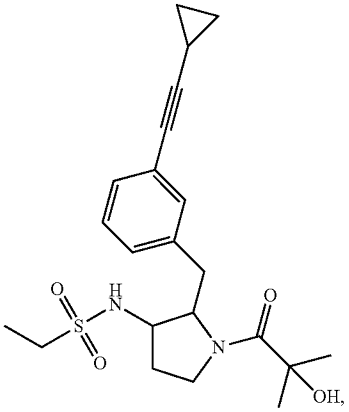
-continued
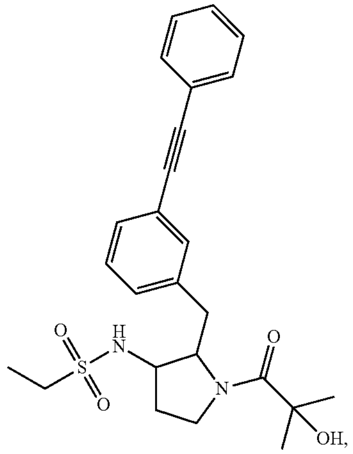
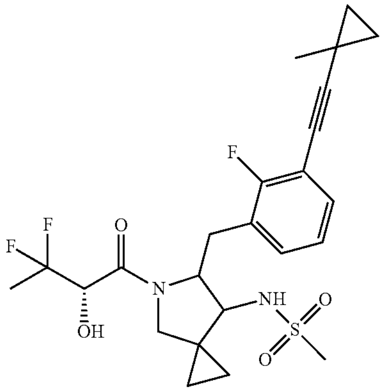
,
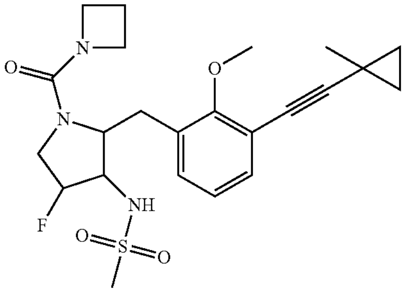
,
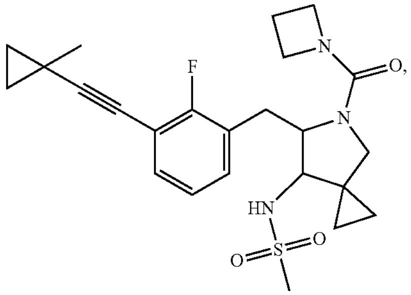
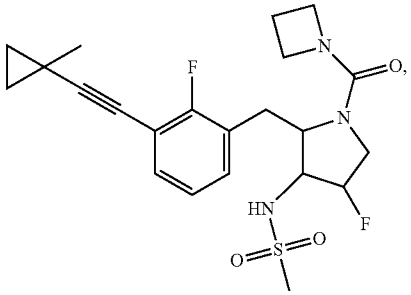

-continued
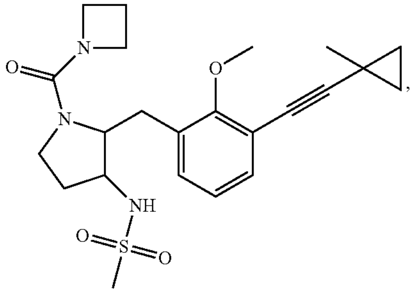
,
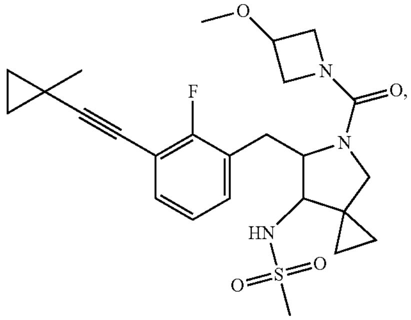
,
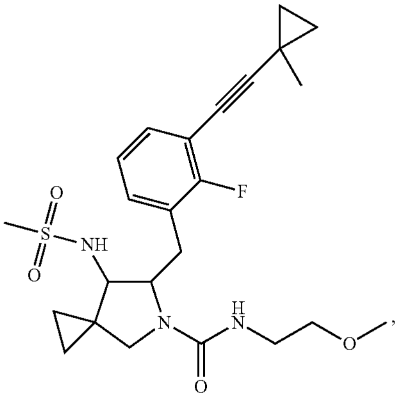
,
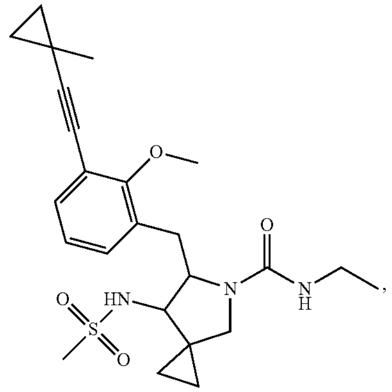
,
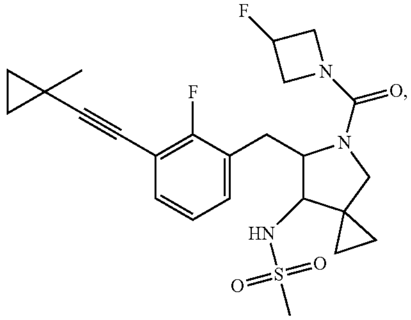
,
-continued
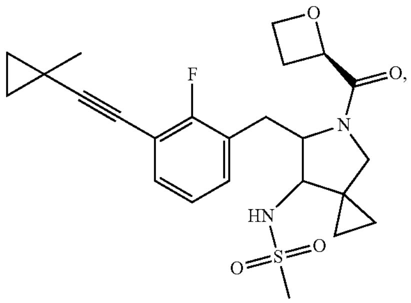
,
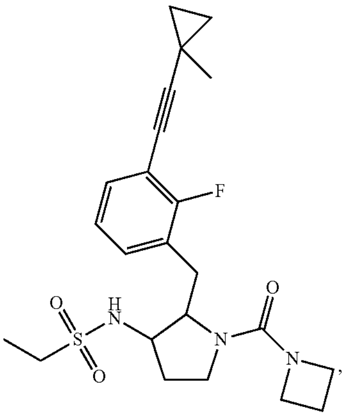
,
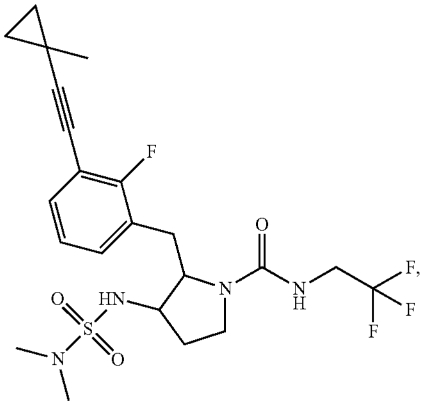
,
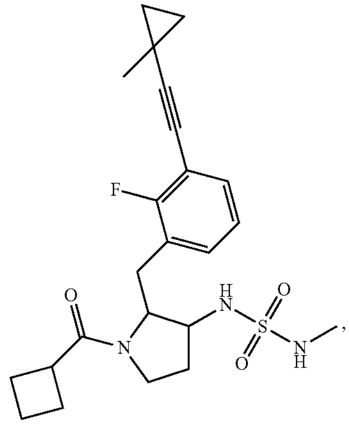
, -continued
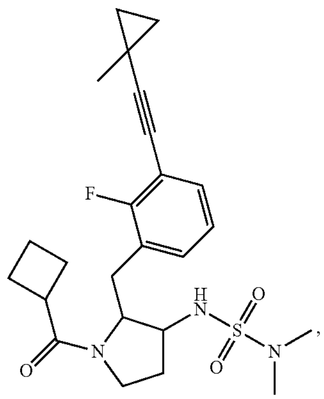
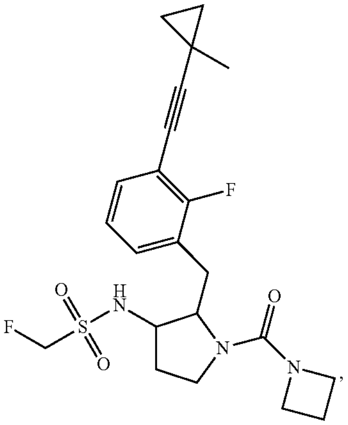
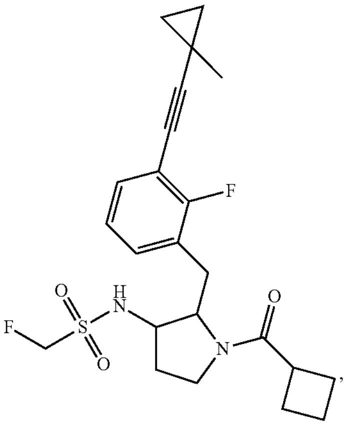
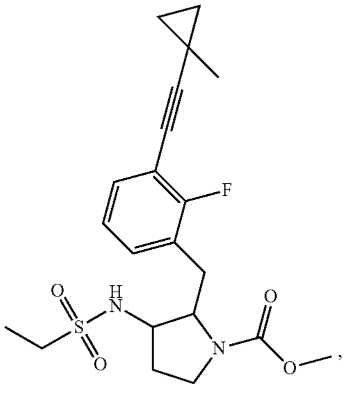
-continued
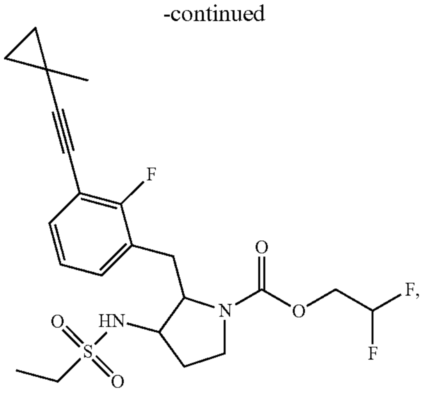
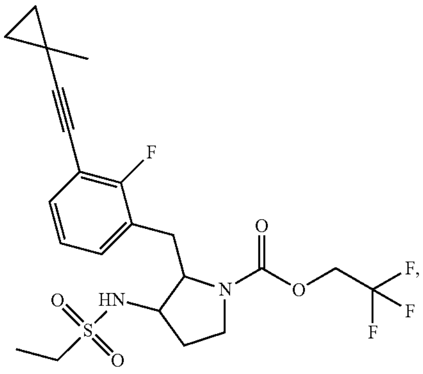
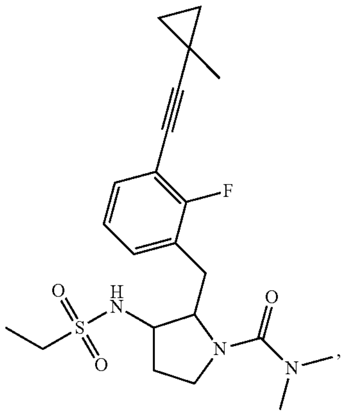
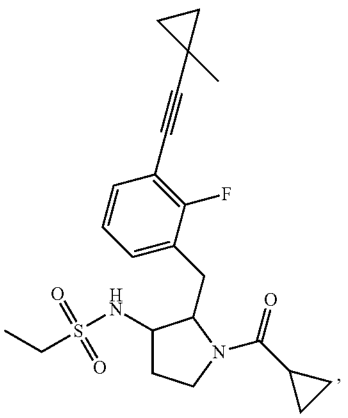

-continued

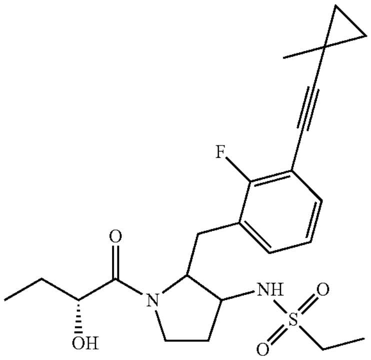
,

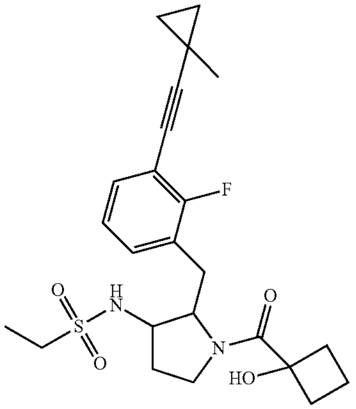
,

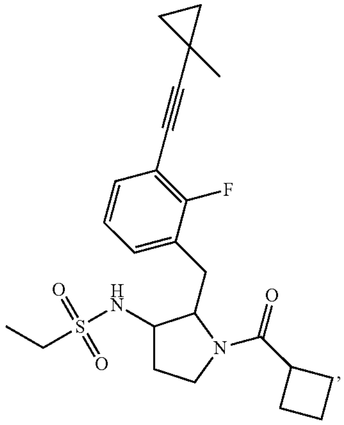
,

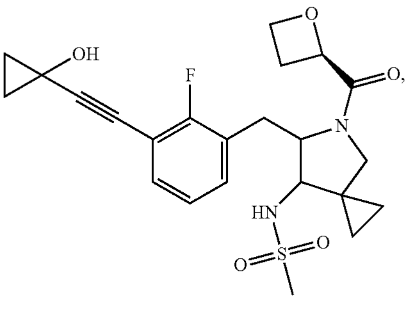
,

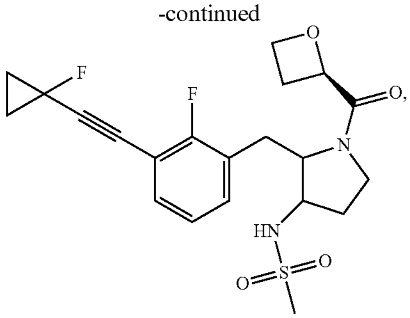
,

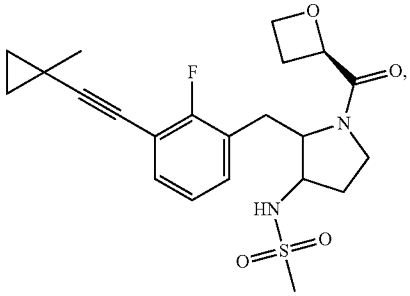
,

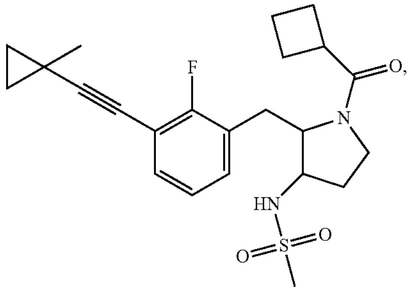
,

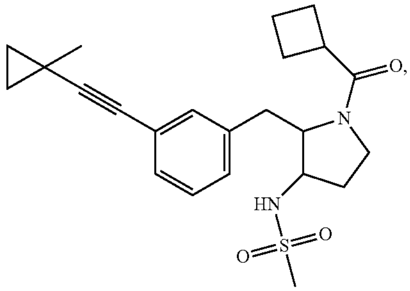
, and

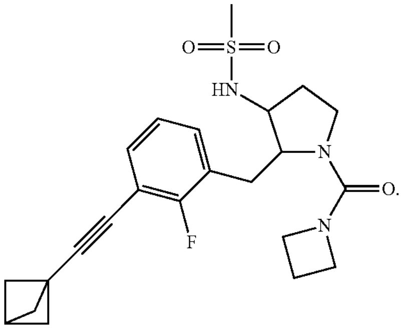
.

17. A pharmaceutical composition comprising the compound of claim 1, or a pharmaceutically acceptable salt thereof, and a pharmaceutically acceptable diluent or carrier.

18. A method of treating or preventing a disease or disorder in a subject in need thereof, comprising administering to the subject the compound of claim 1, or a pharmaceutically acceptable salt thereof, wherein the disease or disorder is associated with an implicated orexin-2 receptor.

19. The method of claim 18, wherein the disease or disorder is a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia.

20. The method of claim 18, wherein the disease or disorder is narcolepsy, idiopathic hypersomnia, sleep apnea, or insomnia.

* * * * *